US012807914B2

(12) United States Patent
Ferrie et al.

(10) Patent No.: US 12,807,914 B2
(45) Date of Patent: Nov. 24, 2026

(54) FIXED BED BIOREACTOR FOR CELL CULTURE AND HARVESTING AND RELATED METHODS

(71) Applicant: CORNING INCORPORATED, Corning, NY (US)

(72) Inventors: Ann MeeJin Ferrie, Salem, NH (US); Vasiliy Nikolaevich Goral, Painted Post, NY (US); Lori Eileen Romeo, Elmira Heights, NY (US)

(73) Assignee: CORNING INCORPORATED, Corning, NY (US)

(*) Notice: Subject to any disclaimer, the term of this patent is extended or adjusted under 35 U.S.C. 154(b) by 468 days.

(21) Appl. No.: 18/289,446

(22) PCT Filed: May 2, 2022

(86) PCT No.: PCT/US2022/027249

§ 371 (c)(1),
(2) Date: Nov. 3, 2023

(87) PCT Pub. No.: WO2022/235553

PCT Pub. Date: Nov. 10, 2022

(65) Prior Publication Data

US 2024/0254421 A1 Aug. 1, 2024

Related U.S. Application Data

(60) Provisional application No. 63/183,386, filed on May 3, 2021.

(51) Int. Cl.
*C12M 1/12* (2006.01)
*C12M 1/26* (2006.01)

(52) U.S. Cl.
CPC ............ *C12M 25/18* (2013.01); *C12M 25/02* (2013.01); *C12M 25/14* (2013.01); *C12M 33/12* (2013.01)

(58) Field of Classification Search
CPC ...... C12M 25/18; C12M 25/02; C12M 25/14; C12M 33/00; C12M 33/12
See application file for complete search history.

(56) References Cited

U.S. PATENT DOCUMENTS

| | | |
|---|---|---|
| 1,143,460 A | 6/1915 | Stull |
| 3,853,712 A | 12/1974 | House et al. |

(Continued)

FOREIGN PATENT DOCUMENTS

| | | |
|---|---|---|
| CN | 200940147 Y | 8/2007 |
| CN | 101605460 A | 12/2009 |

(Continued)

OTHER PUBLICATIONS

Baylon et al; "Past, Present and Future of Surgical Meshes: A Review"; Membranes 2017, 47, 17; 23 Pages doi: 10.3390/membranes7030047.

(Continued)

*Primary Examiner* — Michael L Hobbs
(74) *Attorney, Agent, or Firm* — F. Brock Riggs

(57) ABSTRACT

A fixed-bed bioreactor system (300) is provided that includes a vessel with a media inlet (310), a media outlet (312), and an interior cavity disposed between and in fluid communication with the media inlet and media outlet; a cell culture substrate disposed in the interior cavity between the media inlet and the media outlet in a packed-bed configuration, the cell culture substrate having a plurality of porous disks (308) in a stacked arrangement; and a harvesting volume (2010,2020) to hold a fluid, the harvesting volume being in fluid communication with the interior cavity, wherein each of the plurality of porous disks comprises a surface configured to culture cells thereon. The harvesting volume can be inside or outside of the vessel.

18 Claims, 29 Drawing Sheets

(56) References Cited

U.S. PATENT DOCUMENTS

| | | | |
|---|---|---|---|
| 4,201,845 | A | 5/1980 | Feder et al. |
| 4,755,281 | A | 7/1988 | Penick |
| 4,833,083 | A | 5/1989 | Saxena |
| 4,994,388 | A | 2/1991 | Hillegas et al. |
| 5,012,503 | A | 4/1991 | Nambu et al. |
| 5,079,168 | A | 1/1992 | Amiot |
| 5,266,476 | A | 11/1993 | Sussman et al. |
| 5,501,971 | A | 3/1996 | Freedman et al. |
| 5,510,262 | A | 4/1996 | Stephanopoulos et al. |
| 5,759,830 | A | 6/1998 | Vacanti et al. |
| 5,840,777 | A | 11/1998 | Eagles et al. |
| 5,998,184 | A | 12/1999 | Shi |
| 6,054,142 | A | 4/2000 | Li et al. |
| 6,130,080 | A | 10/2000 | Fuller |
| 6,150,159 | A | 11/2000 | Fry |
| 6,284,284 | B1 | 9/2001 | Naughton |
| 6,334,968 | B1 | 1/2002 | Shapiro et al. |
| 6,875,605 | B1 | 4/2005 | Ma |
| 6,995,013 | B2 | 2/2006 | Connelly et al. |
| 7,122,371 | B1 | 10/2006 | Ma |
| 7,449,331 | B2 | 11/2008 | Whitley |
| 7,524,513 | B2 | 4/2009 | Hai-Quan et al. |
| 7,674,837 | B2 | 3/2010 | Gaserod et al. |
| 7,700,747 | B2 | 4/2010 | Sato |
| 7,968,050 | B2 | 6/2011 | Vogt et al. |
| 8,137,959 | B2 | 3/2012 | Castillo Fernandez |
| 8,198,087 | B2 | 6/2012 | Bayon et al. |
| 8,507,263 | B2 | 8/2013 | Asnaghi et al. |
| 8,597,939 | B2 | 12/2013 | Castillo Fernandez |
| 8,653,319 | B2 | 2/2014 | Amery et al. |
| 8,721,963 | B2 | 5/2014 | Matthews et al. |
| 8,951,574 | B2 | 2/2015 | Gehri et al. |
| 8,951,784 | B2 | 2/2015 | Gould et al. |
| 9,089,117 | B2 | 7/2015 | Grande et al. |
| 9,175,259 | B2 | 11/2015 | Nankervis |
| 9,198,997 | B2 | 12/2015 | Myntti et al. |
| 9,217,129 | B2 | 12/2015 | Moretti et al. |
| 9,220,810 | B2 | 12/2015 | Ma et al. |
| 9,228,579 | B2 | 1/2016 | Stobbe |
| 9,273,278 | B2 | 3/2016 | Lee et al. |
| 9,617,506 | B2 | 4/2017 | Jones et al. |
| 9,657,266 | B2 | 5/2017 | Kasuto et al. |
| 9,677,038 | B2 | 6/2017 | Stobbe |
| 9,694,037 | B2 | 7/2017 | Nataraj et al. |
| 9,766,228 | B2 | 9/2017 | Puschmann et al. |
| 10,077,420 | B2 | 9/2018 | Blahut |
| 10,494,421 | B2 | 12/2019 | Castillo |
| 11,111,470 | B2 | 9/2021 | Ferrie et al. |
| 11,118,151 | B2 * | 9/2021 | Ferrie .................... C12M 23/44 |
| 11,401,493 | B2 | 8/2022 | Ferrie et al. |
| 11,434,460 | B2 | 9/2022 | Ferrie et al. |
| 11,795,426 | B2 * | 10/2023 | Ferrie .................... C12M 25/18 |
| 2002/0155594 | A1 | 10/2002 | Hsieh et al. |
| 2004/0152149 | A1 | 8/2004 | Reid et al. |
| 2004/0211747 | A1 | 10/2004 | Whitley |
| 2005/0014774 | A1 | 1/2005 | Storer et al. |
| 2008/0057561 | A1 | 3/2008 | Takahashi et al. |
| 2008/0206735 | A1 | 8/2008 | Asgari |
| 2009/0076530 | A1 | 3/2009 | Fukutomi et al. |
| 2009/0196901 | A1 | 8/2009 | Guilak et al. |
| 2009/0239298 | A1 | 9/2009 | Gerecht et al. |
| 2009/0263601 | A1 | 10/2009 | Renn |
| 2010/0196963 | A1 | 8/2010 | Naughton et al. |
| 2010/0203638 | A1 | 8/2010 | Adachi et al. |
| 2010/0216229 | A1 | 8/2010 | Kenney et al. |
| 2011/0040226 | A1 | 2/2011 | Amery et al. |
| 2011/0212493 | A1 | 9/2011 | Hirschel et al. |
| 2011/0236256 | A1 | 9/2011 | Matthews et al. |
| 2011/0236932 | A1 | 9/2011 | Stobbe |
| 2011/0250679 | A1 | 10/2011 | Chang |
| 2011/0263021 | A1 * | 10/2011 | Stobbe ................ F04B 43/0736<br>435/243 |
| 2011/0275056 | A1 | 11/2011 | Antwiler |
| 2012/0129257 | A1 | 5/2012 | Yu et al. |
| 2012/0253071 | A1 | 10/2012 | Rau et al. |
| 2013/0116571 | A1 | 5/2013 | Cox et al. |
| 2013/0171710 | A1 | 7/2013 | Prebble |
| 2014/0030805 | A1 | 1/2014 | Kasuto et al. |
| 2014/0193901 | A1 | 7/2014 | Lee et al. |
| 2014/0227769 | A1 | 8/2014 | Strobbe |
| 2014/0243995 | A1 | 8/2014 | Kolewe et al. |
| 2015/0299634 | A1 | 10/2015 | Drugmand et al. |
| 2015/0322399 | A1 | 11/2015 | Purushothaman et al. |
| 2016/0145567 | A1 | 5/2016 | Henry et al. |
| 2016/0281045 | A1 | 9/2016 | Mccall et al. |
| 2016/0304832 | A1 | 10/2016 | Hariri et al. |
| 2017/0166859 | A1 | 6/2017 | Wang et al. |
| 2017/0321178 | A1 * | 11/2017 | Ling ...................... C12M 25/14 |
| 2018/0016547 | A1 | 1/2018 | Hagihara et al. |
| 2018/0044622 | A1 | 2/2018 | Poon et al. |
| 2018/0187139 | A1 | 7/2018 | Patel |
| 2018/0187141 | A1 | 7/2018 | Cox et al. |
| 2018/0195048 | A1 | 7/2018 | Rao |
| 2018/0273891 | A1 | 9/2018 | Tanabe et al. |
| 2018/0282678 | A1 | 10/2018 | Castillo et al. |
| 2019/0062683 | A1 | 2/2019 | Nankervis et al. |
| 2019/0134271 | A1 | 5/2019 | Seo et al. |
| 2019/0275519 | A1 | 9/2019 | Castillo et al. |
| 2019/0382709 | A1 | 12/2019 | Vang et al. |
| 2020/0157493 | A1 | 5/2020 | Ginn et al. |
| 2020/0248121 | A1 | 8/2020 | Ferrie et al. |
| 2020/0248122 | A1 | 8/2020 | Ferrie et al. |
| 2020/0248123 | A1 | 8/2020 | Ferrie et al. |
| 2020/0248124 | A1 | 8/2020 | Ferrie et al. |
| 2020/0255783 | A1 | 8/2020 | Ferrie et al. |

FOREIGN PATENT DOCUMENTS

| | | | |
|---|---|---|---|
| CN | 102250390 | A | 11/2011 |
| CN | 103113627 | A | 5/2013 |
| CN | 105492595 | A | 4/2016 |
| CN | 108315258 | A | 7/2018 |
| DE | 3536349 | A1 | 4/1987 |
| EP | 0044624 | A1 | 1/1982 |
| EP | 0300666 | A1 | 1/1989 |
| EP | 0967273 | A1 | 12/1999 |
| EP | 1245670 | A2 | 10/2002 |
| EP | 2154241 | A2 | 2/2010 |
| EP | 2553860 | A1 | 2/2013 |
| EP | 2566950 | A1 | 3/2013 |
| EP | 3452575 | A1 | 3/2019 |
| JP | 62-171672 | A | 7/1987 |
| JP | 05-179381 | A | 7/1993 |
| JP | 2001-120255 | A | 5/2001 |
| JP | 2008-054521 | A | 3/2008 |
| JP | 2013-063283 | A | 4/2013 |
| JP | 2016-136868 | A | 8/2016 |
| JP | 2019-126341 | A | 8/2019 |
| WO | 88/00235 | A1 | 1/1988 |
| WO | 98/50522 | A1 | 11/1998 |
| WO | 00/05257 | A1 | 2/2000 |
| WO | 01/03750 | A1 | 1/2001 |
| WO | 2005/014774 | A1 | 2/2005 |
| WO | 2005/023323 | A1 | 3/2005 |
| WO | 2006/088029 | A1 | 8/2006 |
| WO | 2011/123805 | A1 | 10/2011 |
| WO | 2011/139957 | A1 | 11/2011 |
| WO | 2012/140519 | A2 | 10/2012 |
| WO | 2014/093444 | A1 | 6/2014 |
| WO | 2014/133805 | A1 | 9/2014 |
| WO | 2014/209856 | A1 | 12/2014 |
| WO | 2014/209865 | A1 | 12/2014 |
| WO | 2015/005349 | A1 | 1/2015 |
| WO | 2016/200888 | A1 | 12/2016 |
| WO | 2017/193075 | A1 | 11/2017 |
| WO | 2017/204563 | A1 | 11/2017 |
| WO | 2018/021367 | A1 | 2/2018 |
| WO | 2018/051415 | A1 | 3/2018 |
| WO | 2018/187808 | A1 | 10/2018 |
| WO | 2019/090211 | A1 | 5/2019 |
| WO | 2019/104069 | A1 | 5/2019 |
| WO | 2019/175442 | A1 | 9/2019 |

(56) References Cited

FOREIGN PATENT DOCUMENTS

| | | | |
|---|---|---|---|
| WO | 2019/206902 | A1 | 10/2019 |
| WO | 2020/163329 | A1 | 8/2020 |
| WO | 2021/091683 | A1 | 5/2021 |

OTHER PUBLICATIONS

Cereijido, M., "Polarized monolayers formed by epithelial cells on a permeable and translucent support", The Journal of Cell Biology, 1978, vol. 77, No. 3, pp. 853-880.
Emmerling et al; "Rational Plasmid Design and Bioprocess Optimization to Enhance Recombinant Adeno-Associated Virus {Aav) Productivity in Mammalian Cells"; Biotechnol. J. 2016, 11,(2) 290297.
Hoch et al; "Chemical Tailoring of Gelatin to Adjust Its Chemical and Physical Properties rOR Functional Bioprinting"; J. Mater. Chem. B, 2013, 1,230; pp. 5675-5685.
House et al; "Method for Bulk Culture of Animal Cells on Plastic Film"; Expreimental Cell Research 71 (1972) pp. 293-296.
International Search Report and Written Opinion of the International Searching Authority; PCT/US20/056240; Mailed Feb. 4, 2021; 10 Pages; European Patent Office.
International Search Report and Written Opinion of the International Searching Authority; PCT/US2021/059851; mailed on Mar. 14, 2022, 12 pages; European Patent Office.
International Search Report and Written Opinion of the International Searching Authority; PCT/US2022/027249; mailed on Aug. 22, 2022, 11 pages; European Patent Office.
Knight; "Multisurface Glass Roller Bodle for Growth of Animal Cells in Culture"; Applied Environmental Microbiology, vol. 33, No. 3, 1977, pp. 666-669.
Kuo, S. M., et al., "Plasma-modified Nylon Meshes as Supports for Cell Culturing", Artificial Cells, Blood Substitutes, and Biotechnology, vol. 25, No. 6, 1997, pp. 551-562.
Lesch et al.; "Process Development of Adenoviral Vector Production in Fixed Bed Bioreactor: From Bench to Commercial Scale"; Human Gene Therapy, vol. 26, No. 8, (2015).
Moczulska et al; "Biological Characterization of Woven Fabric Using Two- and Three-Dimensional Cell Cultures"; Journal of Biomedical Materials Research A; Apr. 2012 vol. 100A, Issue 4, pp. 882-893 DOI: 10.1002/jbm.a.34023.
Moroni et al; "3D Fiber-Deposited Scaffolds for Tissue Engineering: Influence of Pores Geometry and Architecture on Dynamic Mechanical Properties"; Biomaterials 27 (2006) 974985.
Rainger et al; "A Novel System for Investigating the Ability of Smooth Muscle Cells and Fibroblasts to Regulate Adhesion of Flowing Leukocytes to Endothelial Cells"; Journal of Immimmunological Methods; 255 (2001) 73-82.
Rodenhizer et al; "Development of Tracer: Tissue Roll for Analysis of Cellular Environment and Response"; Biofabrication, 8 (045008) 18 Pages.
Simon et al; "Polymer-Based Mesh as Supports for Multi-Layered 3D Cell Culture and Assays"; Biomaterials; 35(1); 2014; pp. 259-268 doi: 10.1016/j.biomaterials.2013.09.049.
Simon, K. A., et al., "Disulfide-Based Diblock Copolymer Worm Gels: A Wholly-Synthetic Thermoreversible 3D Matrix for Sheet-Based Cultures", Biomacromolecules, vol. 16, No. 12, 2015, pp. 3952-3958.
Thuenauer, R., et al., "Microfluidic approaches for epithelial cell layer culture and characterisation", The Analyst, vol. 139, No. 13, 2014, pp. 3206-3218.

* cited by examiner

| Runs | Ascent FBR surface area | % GFP+ cells | Bulk VG/cm$^2$ |
|---|---|---|---|
| Run 1 | 0.2 m$^2$ | 90 | 1.74E+10 |
| Run 2 | 0.2 m$^2$ | 93 | 3.00E+10 |
| Run 3 | 0.2 m$^2$ | 89 | 2.16E+10 |
| | **Average** | **91** | **2.30E+10** |
| Run 4 | 0.7 m$^2$ | 94 | 3.19E+10 |
| Run 5 | 0.7 m$^2$ | 87 | 2.98E+10 |
| Run 6 | 0.7 m$^2$ | 89 | 1.86E+10 |
| Run 7 | 0.7 m$^2$ | 91 | 2.38E+10 |
| | **Average** | **90** | **2.60E+10** |
| Run 9 | 2.5 m$^2$ | 89 | 1.61E+10 |
| Run 10 | 2.5 m$^2$ | 95 | 2.70E+10 |
| Run 11 | 2.5 m$^2$ | 90 | 1.44E+10 |
| Run 12 | 2.5 m$^2$ | 90 | 1.23E+10 |
| | **Average** | **91** | **1.75E+10** |

FIG. 21

AAV2-GFP VG/cm²

| | Exp 1 | Exp2 | Exp3 | Average | % of Embodiment A |
|---|---|---|---|---|---|
| Embodiment A | 2.02E+10 | 1.43E+10 | 1.23E+10 | 1.56E+10 | 100 |
| Other FBR 2.65 m2 | 6.29E+08 | 7.66E+08 | 6.40E+08 | 6.78E+08 | 4.3 |
| T75 flask control | 1.55E+10 | 1.72E+10 | 1.42E+10 | 1.56E+10 | 100 |

FIG. 22

AAV2-GFP VG/vessel

| | Exp 1 | Exp2 | Exp3 | Average | % of Embodiment A |
|---|---|---|---|---|---|
| Embodiment A | 4.91E+14 | 3.47E+14 | 3.00E+14 | 3.79E+14 | 100 |
| Other FBR 2.65 m2 | 1.67E+13 | 2.03E+13 | 1.70E+13 | 1.80E+13 | 4.7 |
| T75 flask control | 1.16E+12 | 1.29E+12 | 1.07E+12 | 1.17E+12 | 0.3 |

FIG. 23

VG/cm2: 1.09E+10
VG/vessel: 2.6E+14

VG/cm2: 1.23E+10
VG/vessel: 2.94E+14

FIXED BED BIOREACTOR FOR CELL CULTURE AND HARVESTING AND RELATED METHODS

CROSS-REFERENCE TO RELATED APPLICATIONS

This is a national stage application under 35 U.S.C. § 371 of International Application No. PCT/US2022/027249, filed May 2, 2022, which claims the benefit of priority under 35 U.S.C. § 119 of U.S. Provisional Application Ser. No. 63/183,386 filed on May 3, 2021, the content of which are relied upon and incorporated herein by reference in their entirety.

FIELD OF THE DISCLOSURE

This disclosure generally relates to apparatuses, systems, and methods for culturing cells. In particular, the present disclosure relates to cell culturing substrates, fixed-bed bioreactor vessels and systems incorporating such substrates, and methods of culturing cells using such substrates and bioreactors.

BACKGROUND

In the bioprocessing industry, large scale cultivation of cells is performed for purposes of the production of hormones, enzymes, antibodies, vaccines and cell therapies. A significant portion of the cells used in bioprocessing are anchorage dependent, meaning the cells need a surface to adhere to for growth and functioning. Traditionally, the culturing of adherent cells is performed on two-dimensional (2D) cell-adherent surfaces incorporated in one of a number of vessel formats, such as T-flasks, petri dishes, cell factories, cell stack vessels, roller bottles, and HYPERStack® vessels. These approaches can have significant drawbacks, including the difficulty in achieving cellular density high enough to make it feasible for large scale production of therapies or cells.

Alternative methods have been suggested to increase volumetric density of cultured cells. These include microcarrier cultures performed in stir tanks. In this approach, cells that are attached to the surface of microcarriers are subject to constant shear stress, resulting in a significant impact on proliferation and culture performance. Another example of a high-density cell culture system is a hollow fiber bioreactor, in which cells may form large three-dimensional aggregates as they proliferate in the interspatial fiber space. However, the cells growth and performance are significantly inhibited by the lack nutrients. To mitigate this problem, these bioreactors are made small and are not suitable for large scale manufacturing Another example of a high-density culture system for anchorage dependent cells is a packed bed bioreactor system. For example, packed bed bioreactor systems that contain a packed bed of support or matrix systems to entrap the cells have been previously disclosed U.S. Pat. Nos. 4,833,083; 5,501,971; and 5,510,262. Packed bed matrices usually are made of porous particles as substrates or non-woven microfibers of polymer. Such bioreactors function as recirculation flow-through bioreactors. One of the significant issues with such bioreactors is the non-uniformity of cell distribution inside the packed bed. For example, the packed bed functions as depth filter with cells predominantly trapped at the inlet regions, resulting in a gradient of cell distribution during the inoculation step. In addition, due to random fiber packaging, flow resistance and cell trapping efficiency of cross sections of the packed bed are not uniform. For example, medium flows fast though the regions with low cell packing density and flows slowly through the regions where resistance is higher due to higher number of entrapped cells. This creates a channeling effect where nutrients and oxygen are delivered more efficiently to regions with lower volumetric cells densities and regions with higher cell densities are being maintained in suboptimal culture conditions. Another significant drawback of packed bed systems disclosed in a prior art is the inability to efficiently harvest intact viable cells at the end of culture process. U.S. Pat. No. 9,273,278 discloses a bioreactor design to improve the efficiency of cell recovery from the packed bed during cells harvesting step. It is based on loosening the packed bed matrix and agitation or stirring of packed bed particles to allow porous matrices to collide and thus detach the cells. However, this approach is laborious and may cause significant cells damage, thus reducing overall cell viability.

Roller bottles have several advantages such as ease of handling, and ability to monitor cells on the attachment surface. However, from a production standpoint, the main disadvantage is the low surface area to volume ratio while the roller bottle configuration occupies a large area of manufacturing floor space. Various approaches have been used to increase the surface area available for adherent cells in a roller bottle format. Some solutions have been implemented in commercially available products, but there remains room for improvement to increase roller bottle productivity even further. Traditionally, a roller bottle is produced as a single structure by a blow-molding process. Such manufacturing simplicity enables economic viability of roller bottles in bioprocessing industry. Some roller bottle modifications to increase the available surface area for cell culturing can be achieved without changing manufacturing process, however only marginal increase of modified roller bottle surface area is obtained. Other modifications of the roller bottle design add significant complexity to manufacturing processes making it economically unviable in the bioprocessing industry. It is desirable therefore to provide roller bottle with increased surface area and bioprocessing productivity, while using the same blow-molding process for its manufacturing.

While manufacturing of viral vectors for early-phase clinical trials is possible with existing platforms, there is a need for a platform that can produce high-quality product in greater numbers in order to reach late-stage commercial manufacturing scale.

There is a need for cell culture matrices, packed-bed bioreactor vessels and bioreactor systems, and methods that enable culturing of cells in a high-density format, with uniform cell distribution, easily attainable and increased harvesting yields, and harvesting of viable cells. In addition, there is a need for such matrices, vessels, systems, and methods that enable a scalable solution capable of adjustable production levels to accommodate the needs of various use cases at different scales, such as from research to process development to manufacturing scale.

SUMMARY

According to an embodiment of this disclosure, a fixed-bed bioreactor system is provided. The bioreactor system includes a vessel having a media inlet, a media outlet, and an interior cavity disposed between and in fluid communication with the media inlet and media outlet. The bioreactor system further includes a cell culture substrate disposed in the interior cavity between the media inlet and the media outlet in a packed-bed configuration, where the cell culture substrate includes a plurality of porous disks in a stacked arrangement. Each of the plurality of porous disks have a surface to culture cells thereon. The interior cavity includes a cell culture section and a spacer section, with the cell culture substrate defining the cell culture section and the spacer section being disposed between the cell culture section and the media outlet.

Aspects of one or more embodiments further include a spacer disposed in the interior cavity between the cell culture substrate and the media outlet and defining the spacer section therebetween. The spacer spaces the cell culture substrate a distance from the media outlet and confines the cell culture substrate to the cell culture section of the interior cavity. The spacer can include a plurality of spacer members extending in a direction parallel to a length of the spacer section. As a further aspect of some embodiments, a packed-bed retainer can be disposed between the cell culture substrate and the spacer, with the packed-bed retainer providing structural support to a top of the cell culture substrate. The packed-bed retainer can be porous, substantially rigid, and extend across a substantial portion of a width of the interior cavity In further aspects of one or more embodiments, each disk of the plurality of porous disks has a first side, a second side opposite the first side, a disk thickness separating the first side and the second side, and a plurality of openings formed in the disk and passing through the disk thickness. The plurality of openings are arranged to allow flow of at least one of cell culture media, cells, or cell by-products through the cell culture substrate.

The system can further include an inlet distribution plate disposed between the media inlet and the cell culture section. The inlet distribution plate can distribute fluid entering the interior cavity from the media inlet across an area of the cell culture substrate. The system can further include an outlet distribution plate disposed between the spacer section and the media outlet.

As an aspect of one or more embodiments, the bioreactor system above further includes a packed-bed retainer disposed between the cell culture substrate and the spacer section, the packed-bed retainer being configured to provide structural support to a top of the cell culture substrate. The packed-bed retainer can be porous, substantially rigid, and extend across a substantial portion of a width of the interior cavity. The system can further include a spacer disposed in the interior cavity between the packed-bed retainer and the media outlet and defining the spacer section therebetween. The spacer spaces the cell culture substrate a distance from the media outlet and to confine the cell culture substrate to the cell culture section of the interior cavity. The packed-bed retainer can be, for example, a rigid grid structure.

As an additional aspect of one or more embodiments, the spacer has an adjustable length and is adjustable to maintain a variety of predetermined distances between the cell culture section and the media outlet, whereby the number of porous disks in the cell culture substrate that can be accommodated in the cell culture section can vary.

In a further aspect of one or more embodiments, the system includes a plurality of removable spacers of different lengths, each of the plurality of removable spacers being able to be placed in the spacer section to maintain a predetermined distance between the cell culture section and the media outlet that is different from a distance maintained by each other spacer, whereby the number of porous disks in the cell culture substrate that can be accommodated in the cell culture section can vary based on a length of the spacer disposed in the spacer section.

In an aspect of some embodiments, the system further includes a least one porous spacer disk disposed between the cell culture substrate and the media inlet. The at least one porous spacer disk can include a spacer disk pore diameter and each of the plurality of porous disks can have a disk pore diameter such that the spacer disk pore diameter is greater than the disk pore diameter. The at least one porous spacer disk can include a first disk having a first spacer disk pore diameter and a second disk having a second spacer disk pore diameter, wherein the first spacer disk pore diameter is different than the second spacer disk pore diameter.

As an aspect of some embodiments, the plurality of porous disks includes a plurality of layers of woven mesh. Each of the plurality of layers of woven mesh has a defined, substantially uniform array of pores. Each layer of the plurality of layers of woven mesh includes a plurality of interwoven fibers, the plurality of interwoven fibers comprising a first group of fibers running in parallel to each other in a first direction, and a second group of fibers running parallel to each other in a second direction. The first direction can be substantially perpendicular to the second direction. In some embodiments, the plurality of interwoven fibers of mesh consists of the first group of fibers and the second group of fibers.

As an aspect of one or more embodiments, the media inlet is configured to supply at least one of cells and cell culture media to the interior cavity before or during cell culture, and the media outlet is configured to withdraw at least one of cells, cell culture media, and cell by-products from the interior cavity during or after cell culture. The media outlet is configured to supply pressurized fluid to the spacer section during a harvesting operation, and the media inlet is configured to withdraw at least one of cells, cell culture media, and cell by-products from the interior cavity during the harvesting operation. The bioreactor system is configured to fill the interior cavity with the pressurized fluid via the media outlet to force out at least one of cells, cell culture media, and cell by-products through the media inlet.

Aspects of one or more embodiments include the plurality of porous disks being from 50 to 1000 porous disks, or being from 100 to 500 porous disks. The plurality of porous disks can culture cells to an average density of about $1.00\times10^7$ to about $2.00\times10^7$ cells per disk. Each disk of the plurality of porous disks can have fibers defining pores therebetween, where the fibers have a diameter from about 50 μm to about 1000 μm, and the pores having a diameter from about 100 μm to about 1000 μm.

BRIEF DESCRIPTION OF THE DRAWINGS

FIG. 21 shows the consistent AAV2-GFP vector yield/$cm^2$ across multiple example runs and bioreactor sizes, according to one or more embodiments.

FIG. 22 shows an example of the AAV2-GFP VG yield/$cm^2$ of an Embodiment A according to this disclosure as compared to other platforms.

FIG. 23 shows an example of the AAV2-GFP VG yield/vessel of an Embodiment A according to this disclosure as compared to other platforms.

DETAILED DESCRIPTION

Figure 1A:
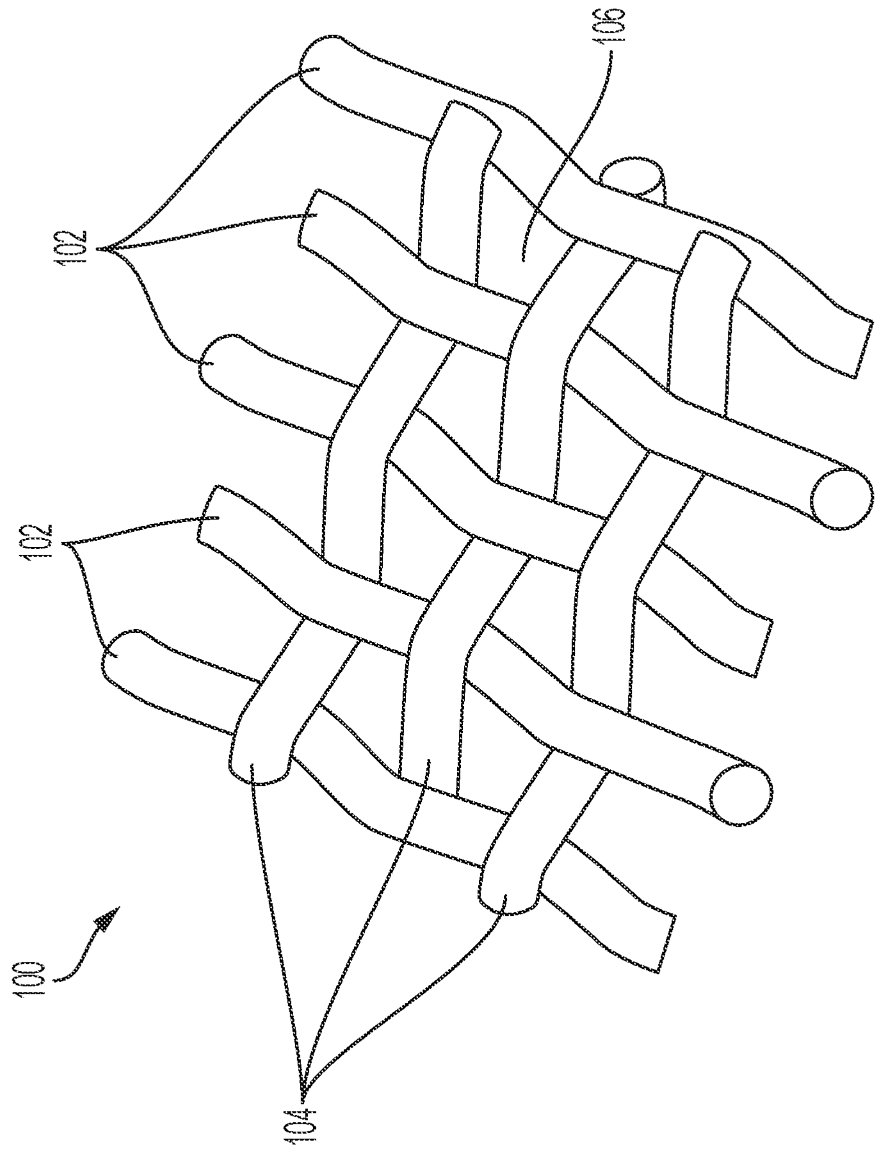
FIG. 1A shows a perspective view of a three-dimensional model of a cell culture substrate, according to one or more embodiments of this disclosure.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

Embodiments of this disclosure are directed to a cell culture substrate, as well as cell culture or bioreactor systems incorporating such a substrate, and methods of culturing cells using such a substrate. Embodiments also include bioreactor vessels capable of performing cell seeding, culture, transfection, and/or harvesting using a cell culture substrate within the vessels, and capable of operating a different production scales.

In conventional large-scale cell culture bioreactors, different types of packed bed bioreactors have been used. Usually these packed beds contain porous matrices to retain adherent or suspension cells, and to support growth and proliferation. Packed-bed matrices provide high surface area to volume ratios, so cell density can be higher than in the other systems. The packed bed often functions as a depth filter, where cells are physically trapped or entangled in fibers of the matrix. However, because of linear flow of the cell inoculum through the packed bed, cells are subject to heterogeneous distribution inside the packed-bed. Thus, for example, there are higher cell densities at the inlet region of the bioreactor and significantly lower cell densities at the outlet part of the bioreactor. This non-uniform distribution of the cells inside of the packed-bed significantly hinders scalability of such bioreactors in bioprocess manufacturing.

Another problem encountered in packed bed bioreactors disclosed in prior art is the channeling effect. Due to random nature of packed nonwoven fibers, the local fiber density at any given cross section of the packed bed is not uniform. Medium flows quickly in the regions with low fiber density (high bed permeability) and much slower in the regions of high fiber density (lower bed permeability). Non-uniform media perfusion across the packed bed creates channeling effect. It manifests itself in development of significant nutrient and metabolite gradients that negatively impact overall cell culture and bioreactor performance. Cells located in the regions of low media perfusion will starve and very often die from the lack of nutrients or metabolite poisoning. Cell harvesting is yet another problem encountered when bioreactors packed with non-woven fibrous scaffolds are used. Due to packed-bed functions as depth filter cells that are released at the end of cell culture process are entrapped inside the packed bed, and cell recovery is very low. This significantly limits utilization of such bioreactors in bioprocesses where live cells are the products.

The present disclosure includes embodiments of a cell growth matrices and/or packed-bed systems for anchorage dependent cells that enable easy and effective scale-up to any practical production scale for cells or cell derived products (e.g., proteins, antibodies, viral particles). In one embodiment, a matrix is provided with a structurally defined surface area for adherent cells to attach and proliferate that has good mechanical strength and forms a highly uniform multiplicity of interconnected fluidic networks when assembled in a packed bed or other bioreactor. In particular embodiments, mechanically stable, non-degradable woven meshes can be used to support adherent cell production. Uniform cell seeding of such a matrix is achievable, as well as efficient harvesting of cells or other products of the bioreactor. In addition, the embodiments of this disclosure support cell culturing to achieve confluent monolayer or multilayer of adherent cells on disclosed matrix, and can avoid formation of 3D cellular aggregates with limited nutrient diffusion and increased metabolite concentrations. The structurally defined matrix of one or more embodiments enables complete cell recovery and consistent cell harvesting from the packed bed of bioreactor. In another embodiment of the present disclosure, a method of cell culturing is provided using bioreactors with the matrix for bioprocessing production of therapeutic proteins, antibodies, viral vaccines, or viral vectors.

As used herein, "structurally defined" means that a component has a non-random, ordered structure, following a defined structural design.

In one or more embodiments, a cell culture matrix is provided that supports attachment and proliferation of anchorage dependent cells in a high volumetric density format. The matrix can be assembled and used in a bioreactor system, such as a perfused back bed bioreactor, and provide uniform cell distribution during the inoculation step, while preventing formation of large and/or uncontrollable cell aggregates inside the matrix or packed bed. Thus, the matrix eliminates diffusional limitations during operation of the bioreactor. In addition, the matrix enables easy and efficient cell harvest from the bioreactor.

The matrix can be formed with a substrate material having a thin or sheet-like construction having first and second sides separated by a relatively small thickness. In other words, the thickness of the sheet-like substrate is small relative to the width and/or length of the first and second sides of the substrate. In addition, a plurality of holes or openings are formed through the thickness of the substrate. The substrate material between the openings is of a size and geometry that allows cells to adhere to the surface of the substrate material as if it were a two-dimensional (2D) surface, while also allowing adequate fluid flow around the substrate material and through the openings. In some embodiments, the substrate is a polymer-based material, and can be formed as a molded polymer sheet; a polymer sheet with openings punched through the thickness; a number of filaments that are fused into a mesh-like layer; or a plurality of filaments that are woven into a mesh layer. The physical structure of the matrix has a high surface-to-volume ratio for culturing anchorage dependent cells. According to various embodiments, the matrix can be arranged or packed in a bioreactor in certain ways to obtain uniform cell seeding, uniform media perfusion, and efficient cell harvest.

Embodiments of this disclosure can achieve viral vector platforms of a practical size that can produce viral genomes on the scale of about $10^{15}$ to about $10^{18}$ or more viral genomes per batch. For example, in some embodiments, the viral genome yield can be about $10^{15}$ to about $10^{16}$ viral genomes or batch, or about $10^{16}$ to about 1019 viral genomes per batch, or about $10^{16}$-$10^{18}$ viral genomes per batch, or about $10^{17}$ to about 1019 viral genomes per batch, or about $10^{18}$ to about $10^{19}$ viral genomes per batch, or about 1018 or more viral genomes per batch. A "batch" can mean a single cell culture run of a single bioreactor vessel. Because of the scalability of the embodiments herein, a bioreactor vessel and the contained cell culture substrate can be appropriately scaled to achieve these yields. This scalability is aided by the structurally defined nature of the cell culture substrate, which provides uniform cell seeding and culturing, uniform media flow, and/or uniform harvesting. In some embodiments, a batch can include multiple bioreactor vessels used in a coordinate cell culture operation.

In addition, the embodiments disclosed herein enable not only cell attachment and growth to a cell culture substrate, but also the viable harvest of cultured cells. The inability to harvest viable cells is a significant drawback in current platforms, and it leads to difficulty in building and sustaining a sufficient number of cells for production capacity. According to an aspect of embodiments of this disclosure, it is possible to harvest viable cells from the cell culture substrate, including between 80% to 100% viable, or about 85% to about 99% viable, or about 90% to about 99% viable. For example, of the cells that are harvested, at least 80% are viable, at least 85% are viable, at least 90% are viable, at least 91% are viable, at least 92% are viable, at least 93% are viable, at least 94% are viable, at least 95% are viable, at least 96% are viable, at least 97% are viable, at least 98% are viable, or at least 99% are viable. Cells may be released from the cell culture substrate using, for example, trypsin, TrypLE, or Accutase.

Figure 1B:
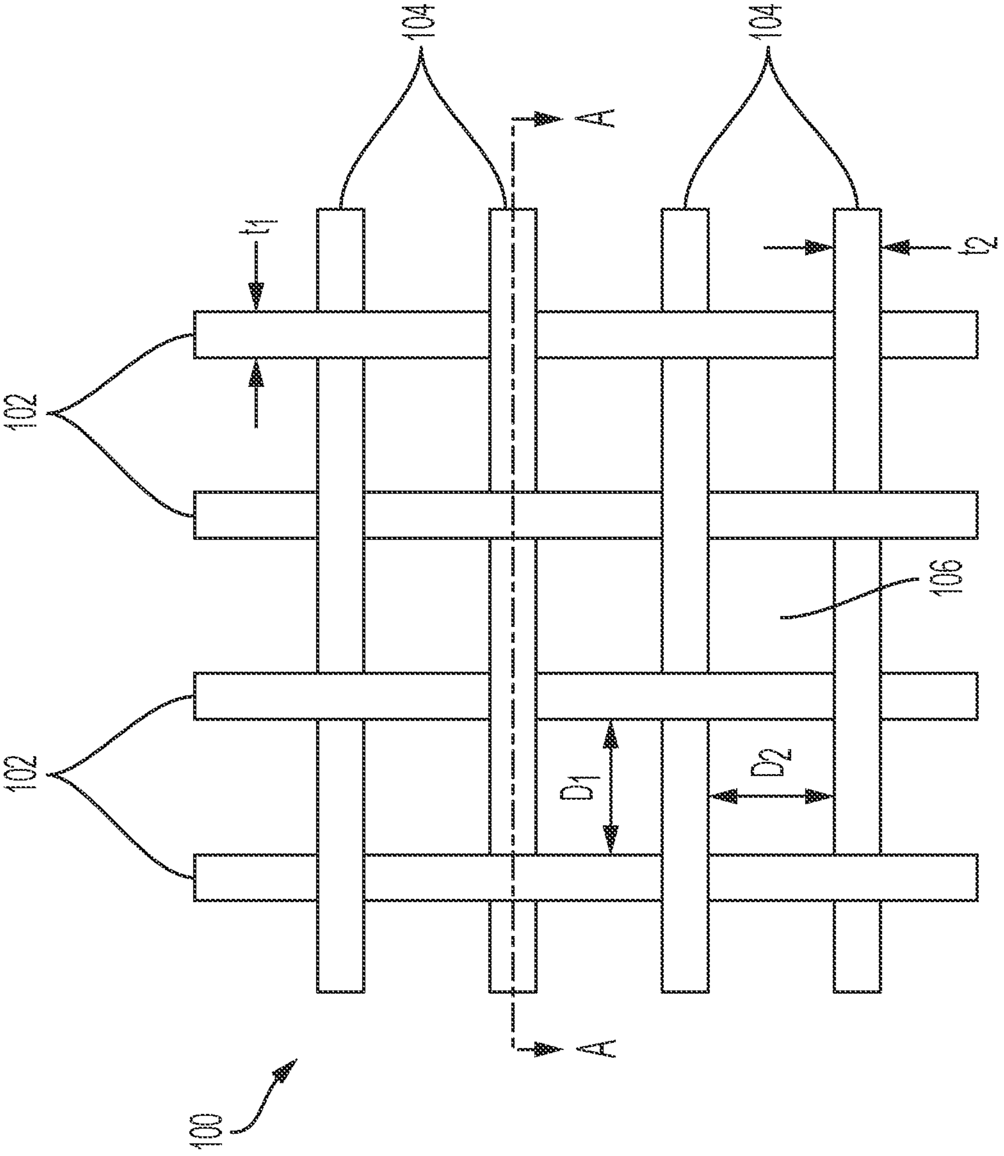
FIG. 1B is a two-dimensional plan view of the substrate of FIG. 1A.
Figure 1C:
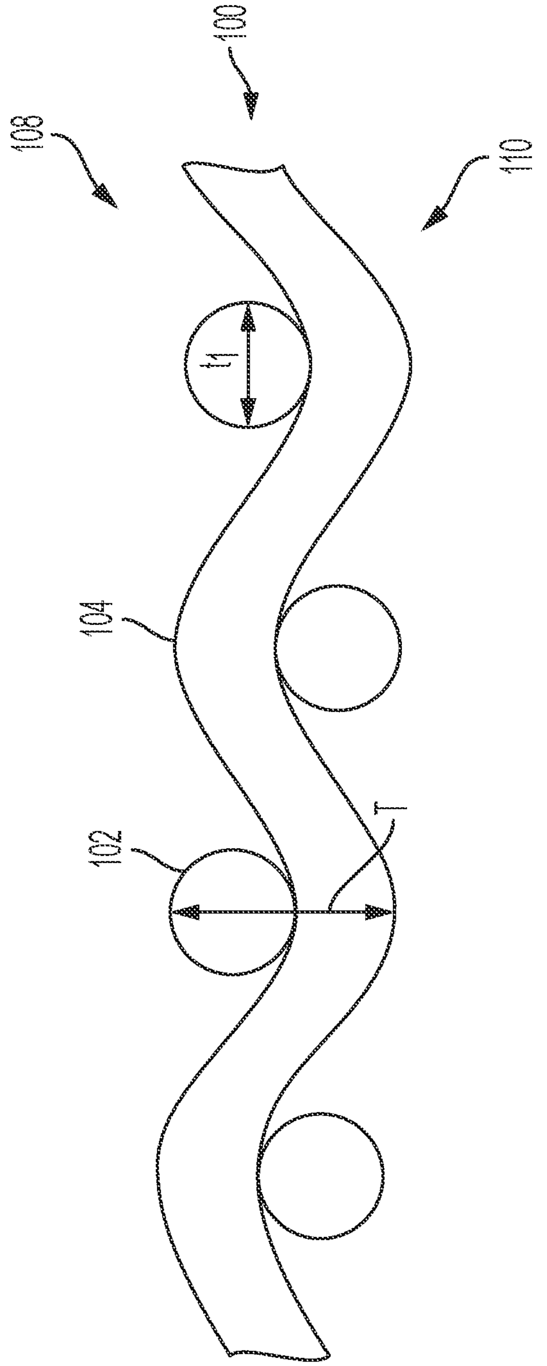
FIG. 1C is a cross-section view along line A-A of the substrate in FIG. 1B.

FIGS. 1A and 1B show a three-dimensional (3D) perspective view and a two-dimensional (2D) plan view, respectively, of a cell culture substrate 100, according to an example of one or more embodiments of this disclosure. The cell culture substrate 100 is a woven mesh layer made of a first plurality of fibers 102 running in a first direction and a second plurality of fibers 104 running in a second direction. The woven fibers of the substrate 100 form a plurality of openings 106. The size and shape of the openings can vary based on the type of weave (e.g., number, shape and size of filaments; angle between intersecting filaments, etc.). An opening can be defined by a certain width or diameter, as shown by the first diameter $D_1$ and second diameter $D_2$ in FIG. 1B. A woven mesh may be considered, on a macro-scale, a two-dimensional sheet or layer. However, a close inspection of a woven mesh reveals a three-dimensional structure due to the rising and falling of intersecting fibers of the mesh. Thus, as shown in FIG. 1C, a thickness T of the woven mesh 100 may be thicker than the thickness of a single fiber. As used herein, the thickness T is the maximum thickness between a first side 108 and a second side 110 of the woven mesh.

In FIG. 1B, the openings 106 have a diameter $D_1$, defined as a distance between opposite fibers 102, and a diameter $D_2$, defined as a distance between opposite fibers 104. $D_1$ and $D_2$ can be equal or unequal, depending on the weave geometry. Where $D_1$ and $D_2$ are unequal, the larger can be referred to as the major diameter, and the smaller as the minor diameter. In some embodiments, the diameter of an opening may refer to the widest part of the opening. Unless otherwise specified, the opening diameter, as used herein, will refer to a distance between parallel fibers on opposite sides of an opening.

A given fiber of the plurality of fibers 102 has a thickness $t_1$, and a given fiber of the plurality of fibers 104 has a thickness $t_2$. In the case of fibers of round cross-section, as shown in FIG. 1A, or other three-dimensional cross-sections, the thicknesses $t_1$ and $t_2$ are the maximum diameters or thicknesses of the fiber cross-section. According to some embodiments, the plurality of fibers 102 all have the same thickness $t_1$, and the plurality of fiber 104 all have the same thickness $t_2$. In addition, $t_1$ and $t_2$ may be equal. However, in one or more embodiments, $t_1$ and $t_2$ are not equal. In addition, each of the plurality of fibers 102 and plurality of fibers 104 may contain fibers of two or more different thicknesses (e.g., $t_{1a}$, $t_{1b}$, etc., and $t_{2a}$, $t_{2b}$, etc.). Due to three-dimensional nature of woven mesh, as shown in FIGS. 1A-1C, the effective surface area of the fibers available for cell attachment and proliferation exceeds the surface area for attachment on an equivalent planar 2D surface having the same substrate dimensions on a macro-scale.

The woven mesh can be comprised of monofilament or multifilament polymer fibers. In one or more embodiments, a monofilament fiber may have a diameter in a range of about 50 μm to about 1000 μm. On a microscale level, due to the scale of the fiber compared to the cells (e.g., the fiber diameters being larger than the cells), the surface of monofilament fiber is presented as regular 2D surface for adherent cells to attach and proliferate. Such fibers are woven into a mesh that has a defined pattern and a certain amount of structural rigidity. Fibers can be woven into a mesh with openings ranging from about 100 μm×100 μm to about 1000 μm×1000 μm. These ranges of the filament diameters and opening diameters are examples of some embodiments, but are not intended to limit the possible feature sizes of the mesh according to all embodiments.

The substrate mesh can be fabricated from monofilament or multifilament fibers of polymeric materials compatible in cell culture applications, including, for example, polystyrene, polyethylene terephthalate, polycarbonate, polyvinylpyrrolidone, polybutadiene, polyvinylchloride, polyethylene oxide, polypyrroles, and polypropylene oxide. Mesh substrates may have a different structure patterns or weaves, including, for example knitted, warp-knitted, or woven (plain weave, twilled weave, Dutch weave, five needle weave).

Figure 2A:
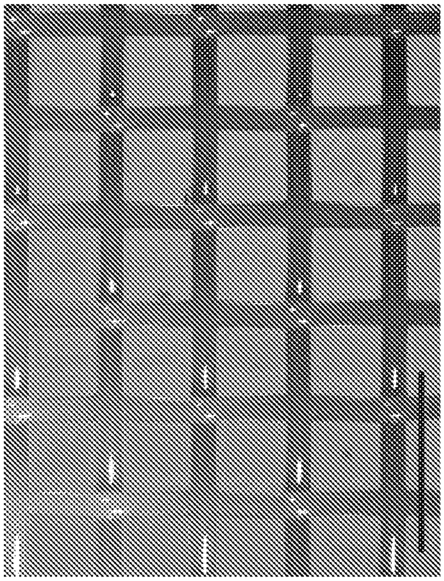
FIG. 2A is a photograph of an example cell culture substrate with a first geometry, according to some embodiments.
Figure 2B:
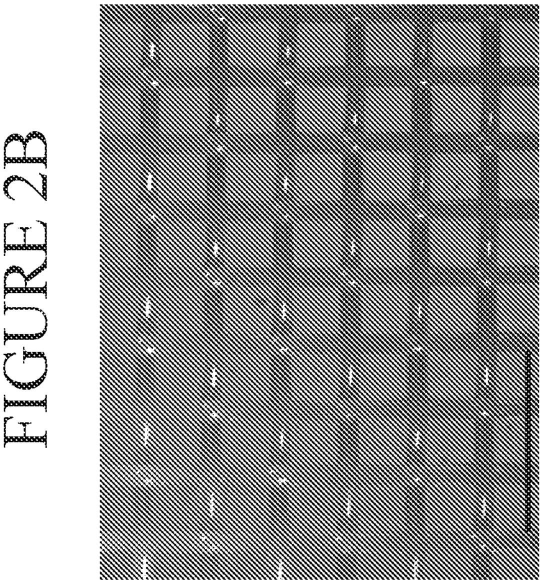
FIG. 2B is a photograph of an example cell culture substrate with a second geometry, according to some embodiments.
Figure 2C:
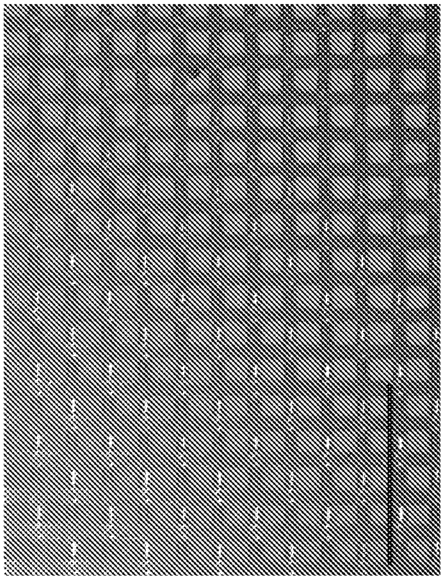
FIG. 2C is a photograph of an example cell culture substrate with a third geometry, according to some embodiments.

The surface chemistry of the mesh filaments may need to be modified to provide desired cell adhesion properties. Such modifications can be made through the chemical treatment of the polymer material of mesh or grafting cell adhesion molecules to the filament surface. Alternatively, meshes can be coated with thin layer of biocompatible hydrogels that demonstrate cell adherence properties, including, for example, collagen or Matrigel®. Alternatively, surfaces of filament fibers of the mesh can be rendered with cell adhesive properties through the treatment processes with various types of plasmas, process gases, and/or chemicals known in the industry FIGS. 2A-2C show different examples of woven mesh according to some contemplated embodiments of this disclosure. The fiber diameter and opening size of these meshes are summarized in Table 1 below, as well as the approximate magnitude of increase in cell culture surface area provided by a single layer of the respective meshes relative to a comparable 2D surface. In Table 1, Mesh A refers to the mesh of FIG. 2A, Mesh B to the mesh of FIG. 2B, and Mesh C to the mesh of FIG. 2C. The three mesh geometries of Table 1 are examples only, and embodiments of this disclosure are not limited to these specific examples. Because Mesh C offers the highest surface area, it may be advantageous in achieving a high density in cell adhesion and proliferation, and thus provide the most efficient substrate for cell culturing. However, in some embodiments, it may be advantageous for the cell culture matrix to include a mesh with lower surface area, such as Mesh A or Mesh B, or a combination of meshes of different surface areas, to achieve a desired cell distribution or flow characteristics within the culture chamber, for example.

TABLE 1

Comparison of meshes in FIGS. 2A-2C, and the resulting increase in cell culture surface area as compared to a 2D surface.

| | Mesh A | Mesh B | Mesh C |
|---|---|---|---|
| Fiber diameter | 273 ± 3 μm | 218 ± 3 μm | 158 ± 3 μm |
| Mesh opening | 790 × 790 μm | 523 × 523 μm | 244 × 244 μm |
| Surface area increase of one layer of mesh compared to 2D surface | ×1.6 | ×1.8 | ×2.5 |

As shown by the above table, the three-dimensional quality of the meshes provides increased surface area for cell attachment and proliferation compared to a planar 2D surface of comparable size. This increased surface area aids in scalability of the embodiments of this disclosure. For process development and process validation studies, small scale bioreactors are often required to save on reagents cost and increase experimental throughput. Embodiments of this disclosure are applicable to such small-scale studies, but can be scaled-up to industrial scale, as well. For example, if 100 layers of Mesh C in the form of 2.2 cm diameter circles are packed into a cylindrical packed bed with a 2.2 cm internal diameter, the total surface area available for cells to attach and proliferate is equal to about 935 $cm^2$. To scale such bioreactor ten times, one could use a similar setup of a cylindrical packed bed with 7 cm internal diameter and 100 layers of the same mesh. In such a case, the total surface area would be equal 9,350 $cm^2$. In some embodiments, the available surface area is about 99,000 $cm^2/L$ or more. In some embodiments, the bioreactor vessels can have a cell culture matrix with over 100 layers, including for example 100-1000 layers or more, or about 300 layers of cell culture substrate. In some examples, a 300-layer cell culture matrix can have a surface area of about $3\times10^9$ to $5\times10^9$ $cm^2$. In some embodiments, the packed-bed bioreactors have an equivalent surface area of 1 to 10 $m^2$, including for example 1 $m^2$, 2 $m^2$, 2.5 $m^2$, 3 $m^2$, 4 $m^2$, 5 $m^2$, and 10 $m^2$, as well as ranges in between. Because of the plug-type perfusion flow in a packed bed, the same flow rate expressed in $ml/min/cm^2$ of cross-sectioned packed bed surface area can be used in smaller-scale and larger-scale versions of the bioreactor.

By using a structurally defined culture matrix of sufficient rigidity, high-flow-resistance uniformity across the matrix or packed bed is achieved. According to various embodiments, the matrix can be deployed in monolayer or multilayer formats. This flexibility eliminates diffusional limitations and provides uniform delivery of nutrients and oxygen to cells attached to the matrix. In addition, the matrix lacks any cell entrapment regions in a packed bed configuration, allowing for complete cell harvest with high viability at the end of culturing. The matrix also delivers packaging uniformity for the packed bed, and enables direct scalability from process development units to large-scale industrial bioprocessing unit. The ability to directly harvest cells from the packed bed eliminates the need of resuspending a matrix in a stirred or mechanically shaken vessel. Further, the high packing density of the cell culture matrix yields high bioprocess productivity in volumes manageable at the industrial scale.

Figure 3B:
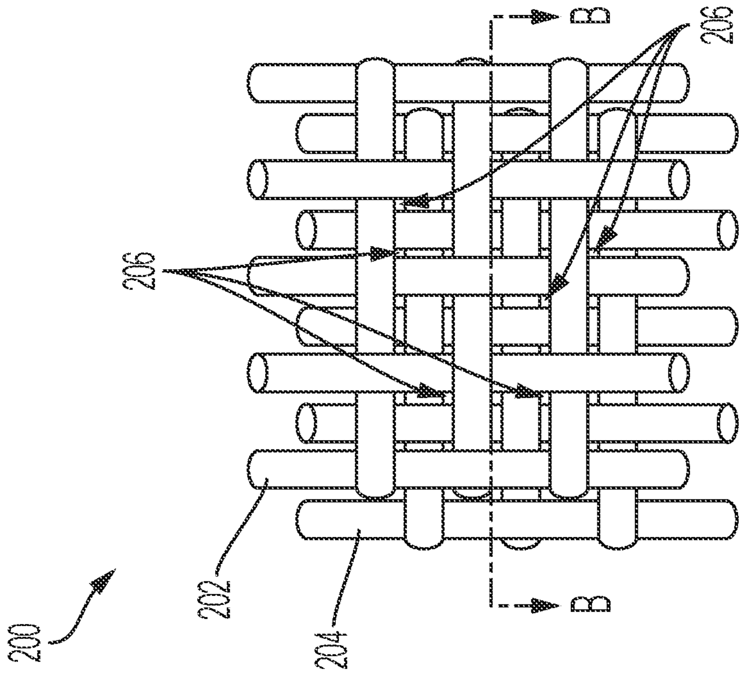
FIG. 3B is a plan view of the multilayer cell culture substrate of FIG. 3A.
Figure 3A:
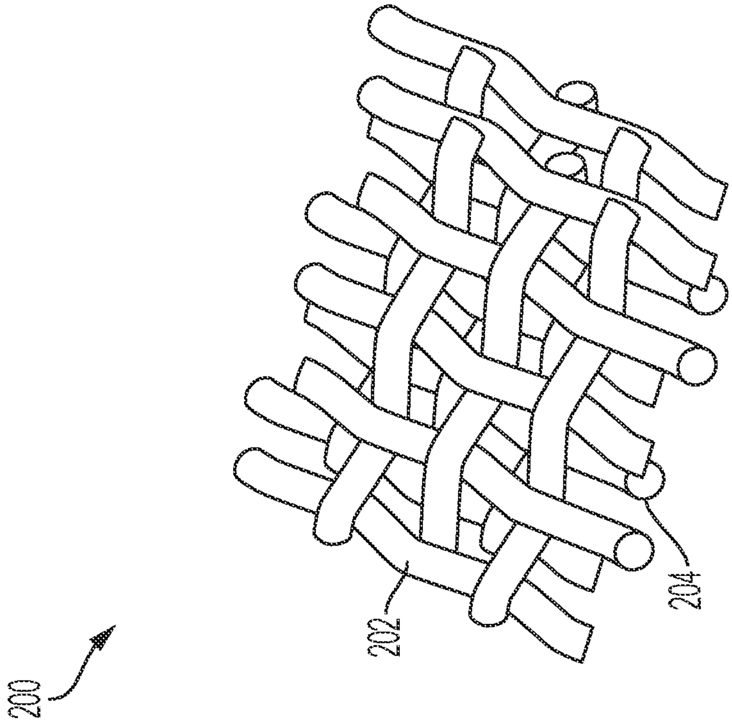
FIG. 3A is a perspective view of a multilayer cell culture substrate, according to one or more embodiments.

FIG. 3A shows an embodiment of the matrix with a multilayer substrate 200, and FIG. 3B is a plan view of the same multilayer substrate 200. The multilayer substrate 200 includes a first mesh substrate layer 202 and a second mesh substrate layer 204. Despite the overlapping of the first and second substrate layers 202 and 204, the mesh geometries (e.g., ratio of opening diameters to fiber diameters) is such that the openings of the first and second substrate layers 202 and 204 overlap and provide paths for fluid to flow through the total thickness of the multilayer substrate 200, as shown by the filament-free openings 206 in FIG. 3B. While FIGS. 3A and 3B show just two layers of substrate, it should be understood that embodiments of this disclosure include cell culture matrices that include many layers of cell culture substrate arranged, for example, in a stacked arrangement as shown in FIGS. 3A and 3B. While FIG. 3B shows that the substrate layers 202 and 204 are not perfectly aligned, the layers can also be aligned so that the openings 206 are in alignment.

Figure 4:
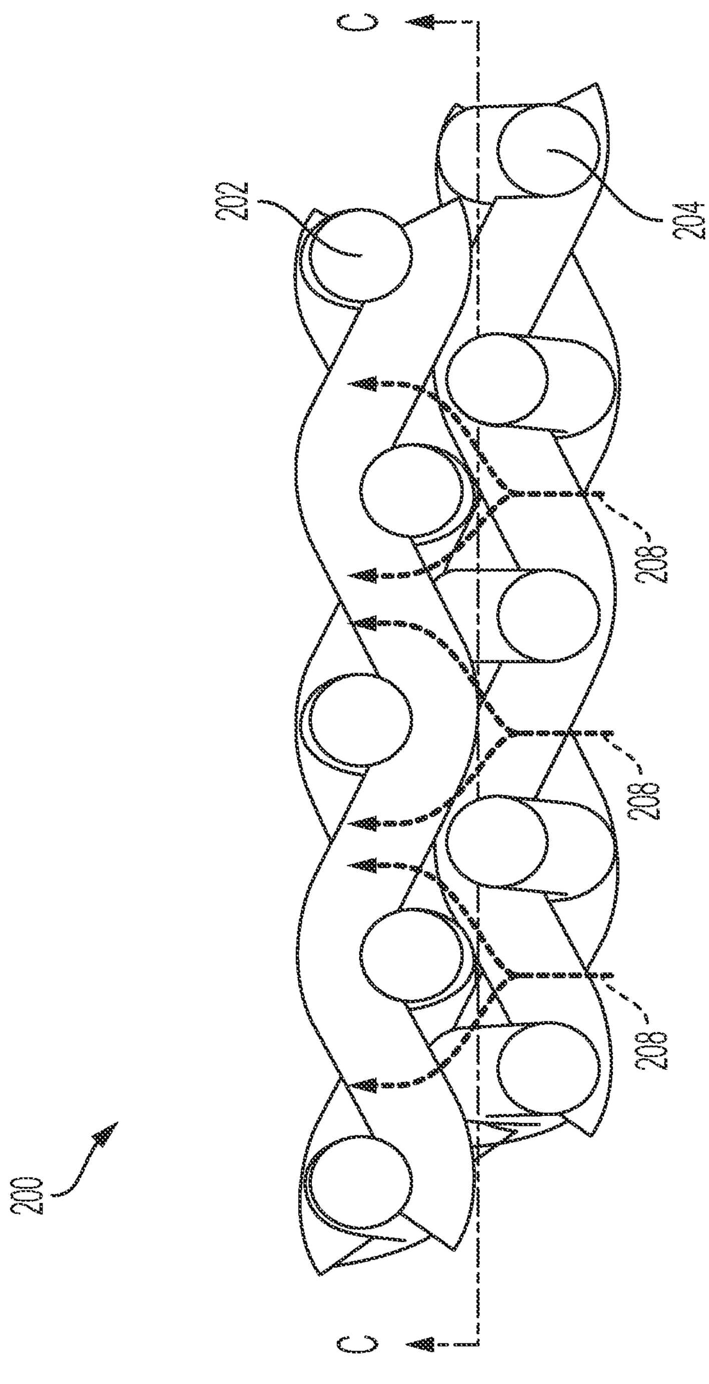
FIG. 4 is a cross-section view along line B-B of the multilayer cell culture substrate of FIG. 3B, according to one or more embodiments.
Figure 5:
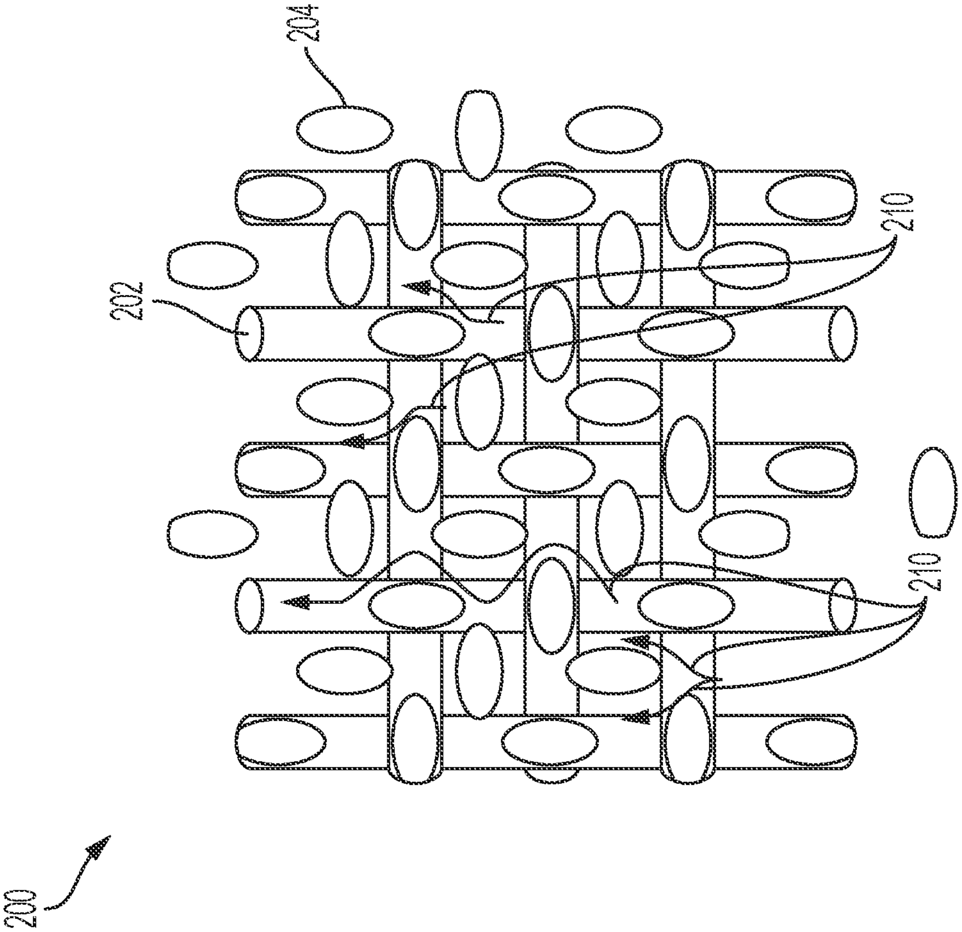
FIG. 5 is a cross-section view along line C-C of the multilayer cell culture substrate of FIG. 4, according to one or more embodiments.

FIG. 4 shows a cross section view of the multilayer substrate 200 at line B-B in FIG. 3B. The arrows 208 show possible fluid flow paths through openings in the second substrate layer 204 and then around filaments in the first substrate layer 202. The geometry of the mesh substrate layers is designed to allow efficient and roughly uniform flow through one or multiple substrate layers. The structure of the matrix 200 can accommodate fluid flow through the matrix in multiple orientations. For example, as shown in FIG. 4, the direction of bulk fluid flow (as shown by arrows 208) is perpendicular to the major side surfaces of the first and second substrate layers 202 and 204. However, the matrix can also be oriented with respect to the flow such that the sides of the substrate layers are parallel to the bulk flow direction. For example, as FIG. 5 shows a cross section view of the multilayer substrate 200 along line C-C in FIG. 4, the structure of matrix 200 allows for fluid flow (arrows 210) through fluid pathways in the multilayer substrate 200. In addition to fluid flow being perpendicular or parallel to the first and second sides of the mesh layers, the matrix can be arranged with multiple pieces of substrate at intermediate angles, or even in random arrangements with respect to fluid flow. This flexibility of the matrix allows for its use in various applications and bioreactor or container designs.

As discussed herein, the cell culture substrate can be used within a bioreactor vessel, according to one or more embodiments. For example, the substrate can be used in a packed bed bioreactor configuration, or in other configurations within a three-dimensional culture chamber. However, embodiments are not limited to a three-dimensional culture space, and it is contemplated that the substrate can be used in what may be considered a two-dimensional culture surface configuration, where the one or more layers of the substrate lay flat, such as within a flat-bottomed culture dish, to provide a culture substrate for cells. Due to contamination concerns, the vessel can be a single-use vessel that can be disposed of after use.

Figure 6:
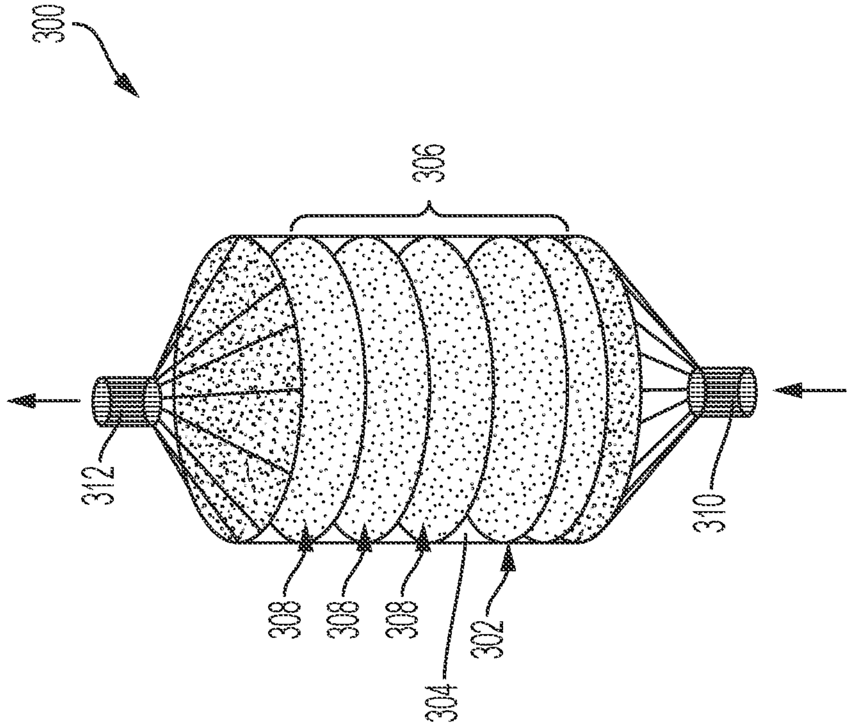
FIG. 6 is a schematic view of a packed-bed cell culture system with a multi-layered cell culture matrix, according to one or more embodiments.

A packed-bed bioreactor system for culturing cells is provided, according to one or more embodiments, in which the cell culture matrix is used within a culture chamber of a bioreactor vessel. FIG. 6 shows an example of a cell culture system 300 that includes a bioreactor vessel 302 having a cell culture chamber 304 in the interior cavity of the bioreactor vessel 302. Within the cell culture chamber 304 is a cell culture matrix 306 that is made from multiple substrate layers 308. The multiple substrate layers 308 can include a plurality of separable and distinct substrate layers that are arranged in a stack, but can also include an integral cell culture matrix in which multiple layers are affixed together. The substrate layers 308 are stacked with the first or second side of a substrate layer facing a first or second side of an adjacent substrate layer. The bioreactor vessel 300 has an inlet 310 at one end for the input of media, cells, and/or nutrients into the culture chamber 304, and an outlet 312 at the opposite end for removing media, cells, or cell products from the culture chamber 304. By allowing stacking of substrate layers in this way, the system can be easily scaled up without negative impacts on cell attachment and proliferation, due to the defined structure and efficient fluid flow through the stacked substrates.

In one or more embodiments, flow resistance and volumetric density of the packed bed can be controlled by interleaving substrate layers of different geometries. In particular, mesh size and geometry (e.g., fiber diameter, opening diameter, and/or opening geometry) define the fluid flow resistance in packed bed format. By interlaying meshes of different sizes and geometries, one can control fluidic resistance in specific portion of bioreactor. This will enable better uniformity of liquid perfusion in packed bed bioreactor. For example, 10 layers of Mesh A (Table 1) followed by 10 layers of Mesh B (Table 1) and followed by 10 layers of Mesh C (Table 1) can be stacked to achieve a desired packed bed characteristic. As another example, the packed bed may start with 10 layers of Mesh B, followed by 50 layers of Mesh C, followed by 10 layers of Mesh B. Such repetition pattern may continue until the full bioreactor is packed with mesh. These are examples only, and used for illustrative purposes without intending to be limiting on the possible combinations. Indeed, various combinations of meshes of different sizes are possible to obtain different profiles of volumetric density of cells growth surface and flow resistance. For example, a packed bed column with zones of varying volumetric cells densities (e.g., a series of zones creating a pattern of low/high/low/high, etc. densities) can be assembled by interleaving meshes of different sizes.

In FIG. 6, the bulk flow direction is in a direction from the inlet 310 to the outlet 312 (as indicating by the direction of the arrows shown), and, in this example, the first and second major sides of the substrate layers 308 are perpendicular to the bulk flow direction. However, embodiments are not limited to this configuration. For example, the substrate can be arranged within the culture space such that the first and second sides are parallel to a bulk flow direction or are at some intermediate angle with respect to the bulk flow direction. Thus, the matrices of embodiments of this disclosure can be employed in either configuration. In any configuration, the substrate can be sized and shaped to appropriately fill the interior space defined by the culture chamber. In addition, the size of individual layers of the substrate or the size of a stack of layers of substrate can be sized to fill the interior space, or either can be sized to fill less than the entirety of the interior space, as desired. For example, in some embodiments, it may be desirable for the stack of substrate layers to occupy less than the full interior space.

As discussed above, embodiments of this disclosure include bioreactor vessels capable of performing cell seeding, culture, transfection, and/or harvesting using a cell culture substrate within the vessels, and capable of operating a different production scales. A bioreactor according to the embodiments of this disclosure enables an end user to run bioprocess experiments on 1× to 10× scale using the same bioreactor unit. The simple scalability model of these embodiments enables bioprocess transfer from research to process development to production scale within one system. Such flexibility in the configuration of the bioreactor capacity will produce savings of cost and time of process optimization and validation in the 1× to 10× scale range. Aspects of some embodiments will also allow end users to seed and harvest cells at the same predefined flow rates without the need for re-optimization during scale-up of the bioreactor.

FIG. 7 shows a perfusion-type bioreactor 320, according to one or more embodiments. The bioreactor 320 includes a media inlet 321 through which media, including fluid, cells, and nutrients, can be fed to an interior cavity 327 of the bioreactor 320. The interior cavity 327 can be thought of as containing a cell culture section 327*a*, in which the cell culture substrate 323 is disposed, and a spacer section 327*b*, in which a spacer 325 is disposed. The media inlet 321 leads to a flow distribution plate 322. The flow distribution plate 322 disperses and/or distributes the incoming media across the width of the interior space where the cell culture substrate 323 is held. Although not shown, a similar flow distribution plate can be disposed just before the outlet 326. The outlet distribution plate can help funnel media or components from across the width of the interior cavity 327 to the outlet. As will be explained further below, the bioreactor 320 can also be operated in a mode where fluid is put into the interior cavity 327 through the outlet 326, in which case the outlet distribution plate can help distribute the fluid even across the width of the interior cavity 327. In this reversed flow mode, the inlet 321 can be used to remove fluid or components from the interior cavity 327.

The cell culture substrate 323 can correspond to the embodiments disclosed herein, including, for example, a porous polymer substrate. The substrate 323 has a height h extending from a flow-distribution-plate side of the substrate 323 to an opposite side or top of the substrate 323. Optionally, at a top of the substrate 323 opposite to the flow distribution plate 322 is a packed-bed retainer 324. The packed-bed retainer 324 is designed to provide structural support to the substrate 323 against the flow of media coming from the media inlet 321. As such, the packed-bed retainer 324 can help hold a position and/or shape of the packed bed substrate 323. The packed-bed retention layer 324 can have many configurations according to different embodiments, but generally has a structure sufficient to hold the substrate 323 in place while allowing media, including cells, to pass through the packed-bed retention layer 324. Atop the packed-bed retention layer 324 is a spacer 325. The spacer 325 is sized to substantially fill the spacer section 327*b*, or the interior space above the substrate 323 and/or packed-bed retention layer 324 and before a media outlet 326 at the top of the interior cavity 327. By filling this space, the spacer 325 is braced against a top of the interior space or some support feature within the interior space, and thus keeps the packed-bed retention layer 324 and substrate 323 in place.

The spacer 325 also creates a head space in the spacer section 327*b* above the cell culture section 327*a*. This head space can have the effect of enhancing the uniformity of flow in the substrate 323, especially near the top of the substrate 323. For example, if the top of the substrate 323 is near the top of the interior cavity 327, flow restrictions at the top of the interior cavity 327 may create areas of increased pressure and effect flow uniformity in the packed bed. As will be discussed below, this head space also provides a space for pressurized fluid to start to fill the interior cavity 327 during a harvesting operation.

Figure 7A:
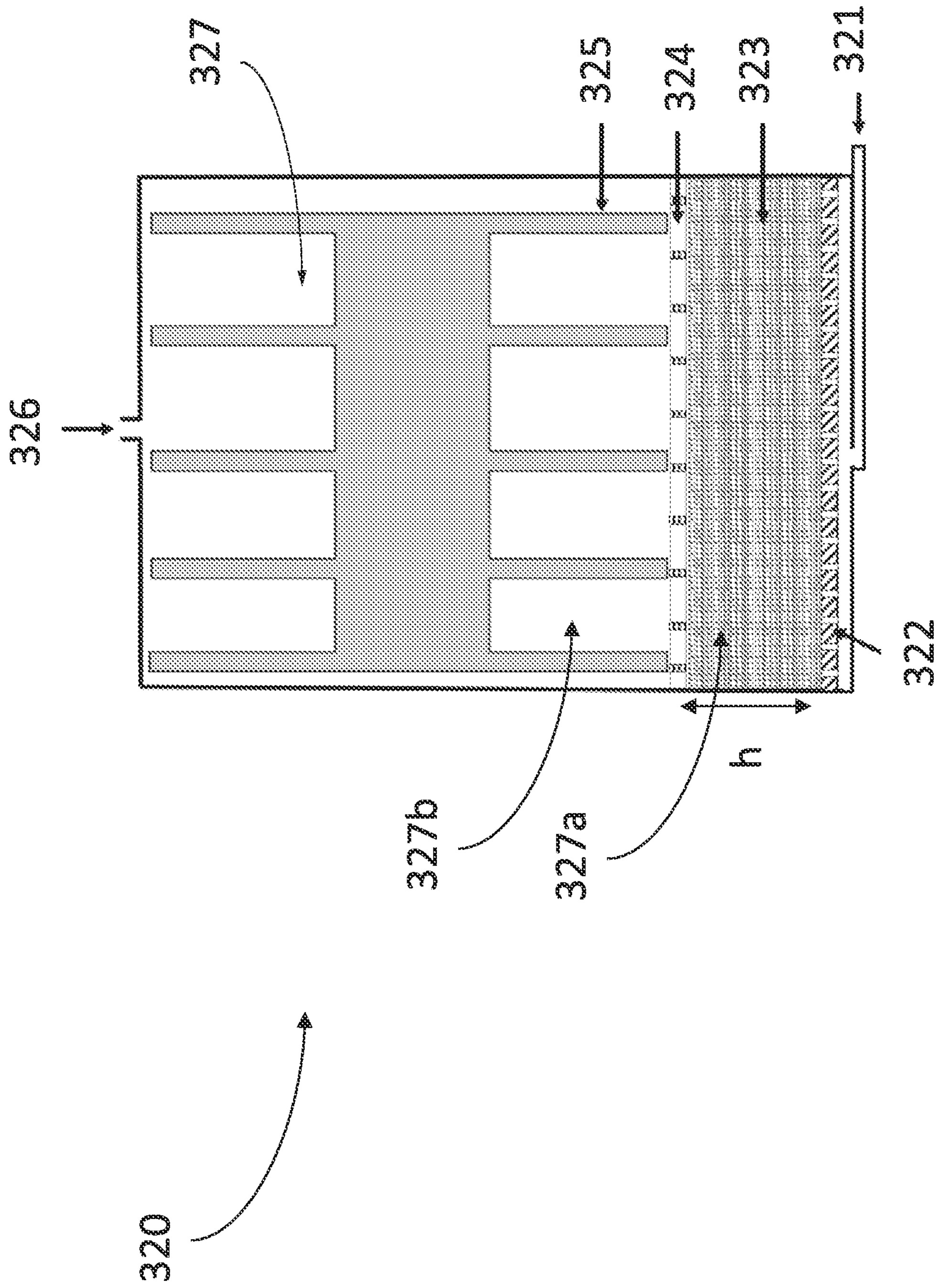
FIG. 7A is cross-section view of a packed-bed cell culture system, according to one or more embodiments.
Figure 7B:
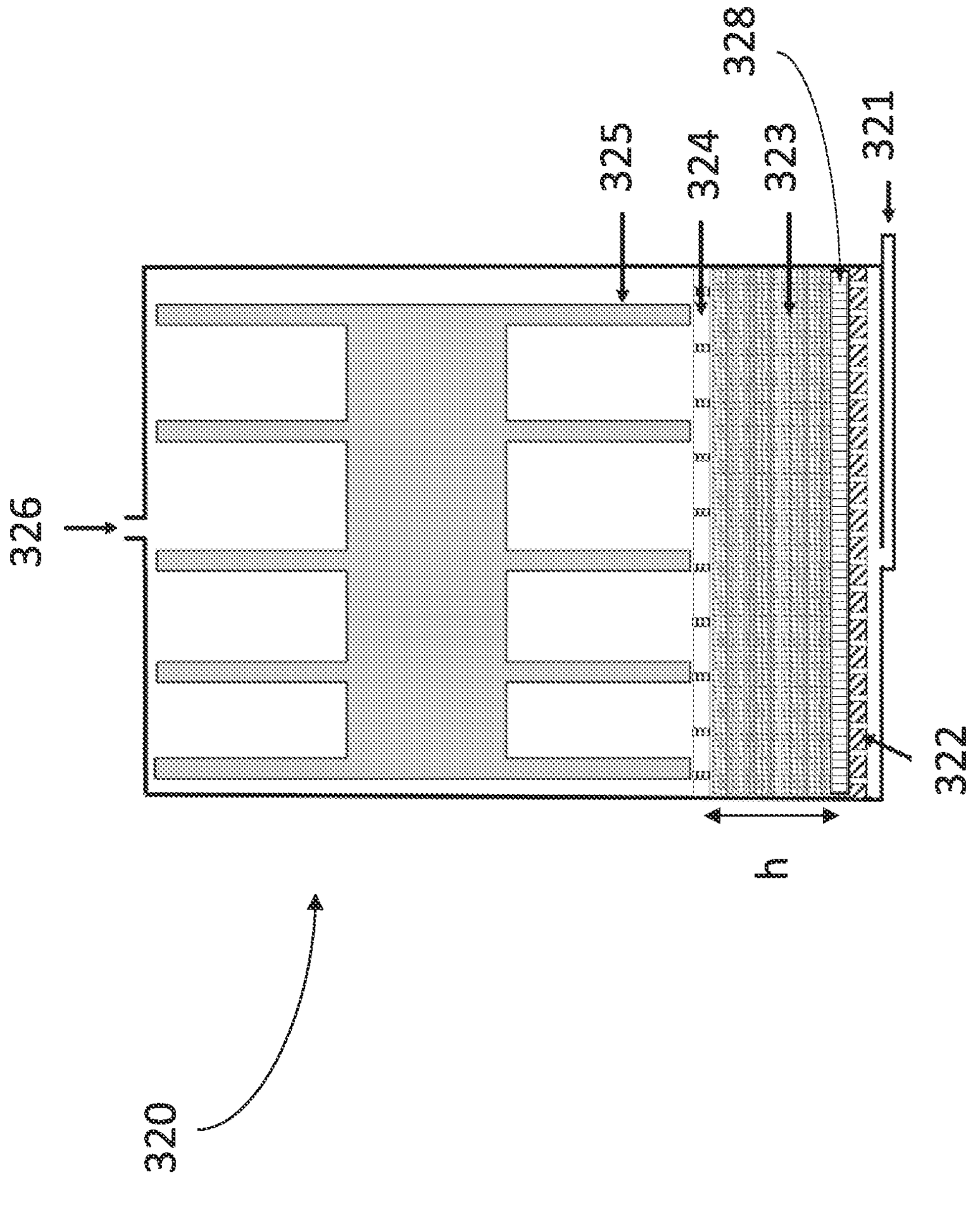
FIG. 7B is cross-section view of a packed-bed cell culture system, according to one or more further embodiments.

FIG. 7B shows a variation on the embodiment of FIG. 7A. In FIG. 7B, at least one porous spacer disk 328 is disposed between the cell culture substrate 323 and the media inlet 321. The porous spacer disk 328 can take different forms, but generally extends across the width of the interior cavity 327 or the width of the substrate 323, and is porous to allow fluid to flow through the porous spacer disk 328. According to embodiments, the porous spacer disk 328 has a spacer disk pore diameter that is greater than a pore diameter of the openings or pores in the substrate. In some embodiments, multiple porous spacer disks 328 can be stacked between the substrate 323 and the inlet 321. These multiple porous spacer disks 328 can each have the same construction (e.g., thickness and spacer disk pore size) or different constructions (e.g., different thicknesses and spacer disk pore sizes). It is contemplated that the porous spacer disk 328 can help further even out and distribute fluid flowing from the inlet 321 or distributor plate 322 before that fluid reaches the cell culture substrate 323.

The substrate 323 in FIGS. 7A and 7B can be non-woven or woven, such as a woven PET substrate. However, the substrate can be non-woven in some embodiments. The substrate can include multiple layers of substrate material in a stacked arrangement, or a roll or spiral of substrate material.

Figure 8:
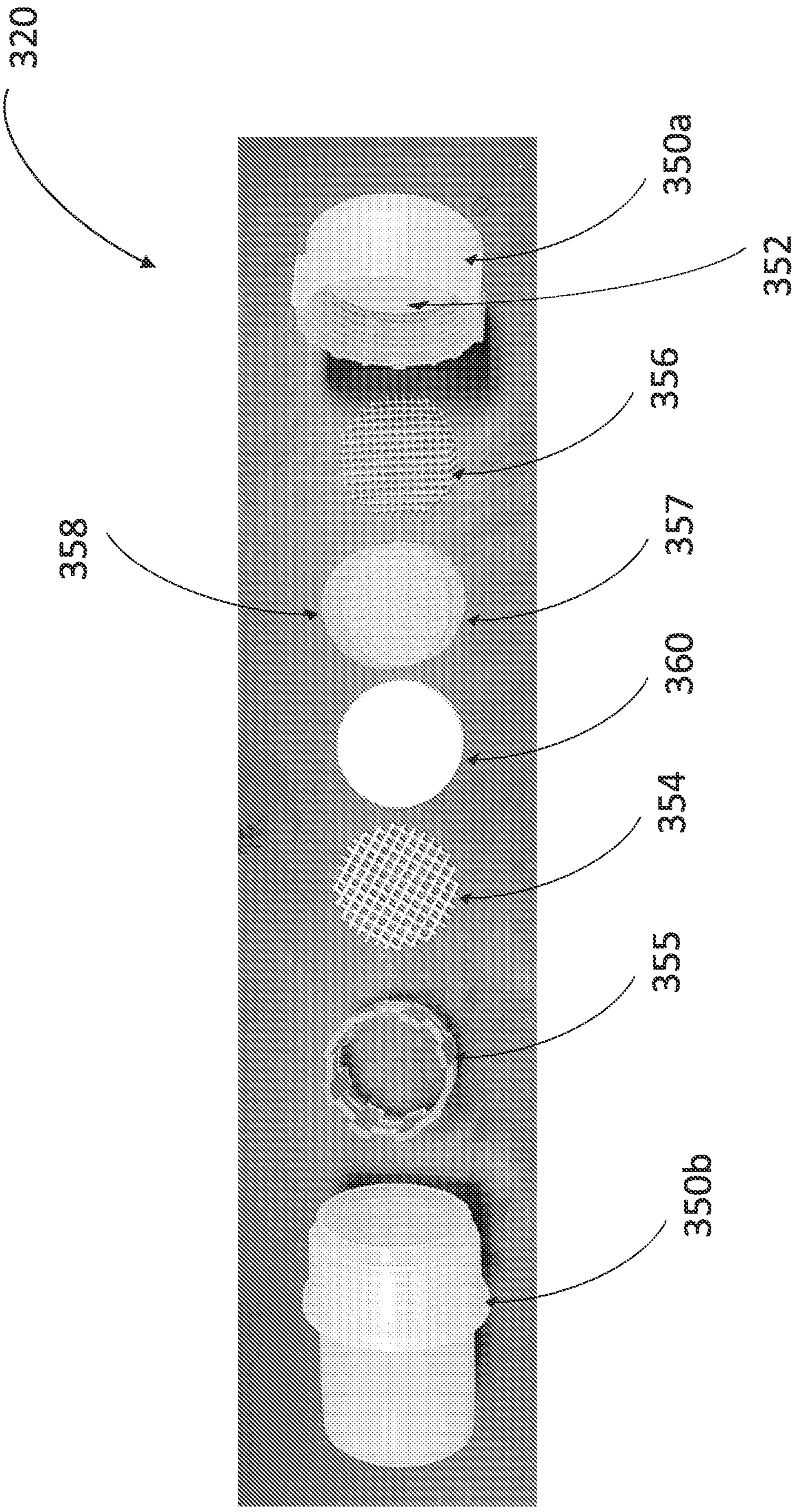
FIG. 8 is a photograph of example components of a bioreactor vessel according to one or more embodiments.

FIG. 8 is a photograph of components of an example of the bioreactor 320 of FIGS. 7A and 7B. As shown, the bioreactor 320 can include two or more separable housing components 350*a* and 350*b*. In the lower housing component 350*a*, a flow distribution plate 352 is shown, which sits above a media inlet (not shown in FIG. 8). An example of a packed-bed retainer 354 is shown. The packed-bed retainer 354 is generally grid-shaped and has a defined thickness. The grid of the packed-bed retainer 354 allows flow of media and other components through the grid, but provides support to any substrate layers within the bioreactor. An example of a spacer 355 is also shown. The shape and size of the housing components 350*a*, 350*b*, distribution plate 352, packed-bed retainer 354, and spacer 355 are shown for example only, and embodiments of this disclosure are not limited to the configuration shown. A first porous spacer disk 356, second porous spacer disk 357, and third porous spacer disk 358 are also shown near the inlet. The second and third porous spacer disk 357, 358 have an identical construction in this example, both being made from a mesh or net material having a spacer disk pore diameter that is greater than a pore or opening diameter of the cell culture substrate 360. The first porous spacer disk 356 is also made from a mesh, net, or grid material, but has a larger spacer disk pore diameter than that of the second and third porous spacer disks 357, 358.

Figure 9A:
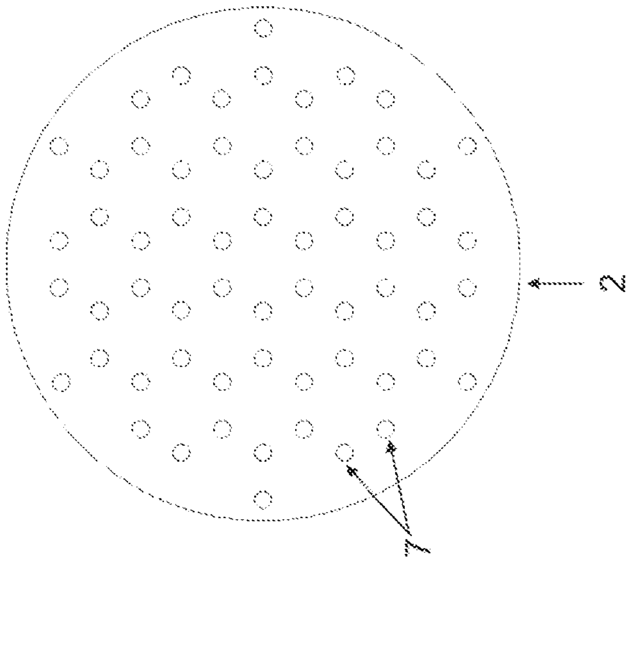
FIG. 9A is a plan view of a flow-distribution plate of the cell culture system of FIGS. 7A-8, according to one or more embodiments.
Figure 9B:
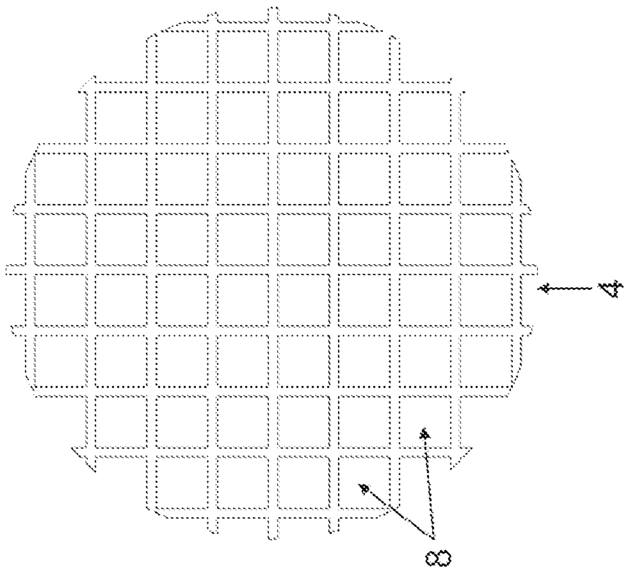
FIG. 9B is a plan view of a packed bed retainer grid of the cell culture system of FIGS. 7A-8, according to one or more embodiments.

FIG. 9A shows a plan view of the distribution plate 2, similar to the distribution plate 352 of FIG. 8. Holes 7 in the distribution plate 2 are arranged to distribute flow evenly across the width of the distribution plate and the interior space of the bioreactor. FIG. 9B shows a plan view of a packed-bed retainer 4, according to some embodiments, which has a grid shape defining a number of large openings 8 to minimize flow resistance, yet effectively retain the cell culture substrate within the packed bed region.

Figure 10:
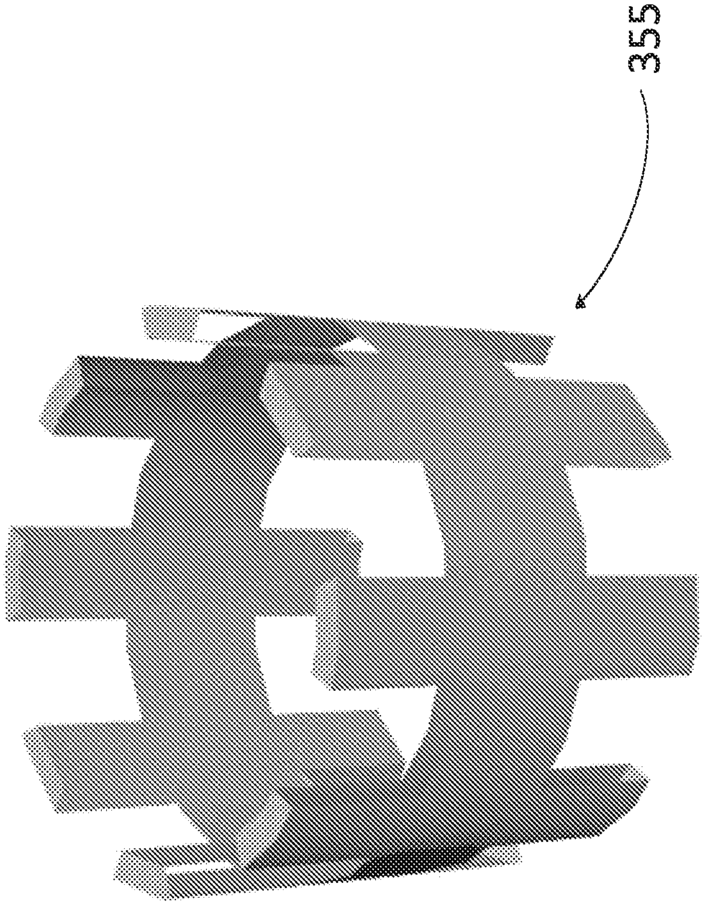
FIG. 10 is a perspective view of a spacer of the cell culture system of FIGS. 7A-8, according to one or more embodiments.

FIG. 10 shows a three-dimensional model of the spacer 355 of FIG. 8. The spacer can compress and/or retain the substrate in the packed bed region, while simultaneously creating a spacer section 327*b* in the interior cavity 327 of the bioreactor (see FIG. 7A) to define the head space over the packed-bed cell culture matrix. Removable spacers 355 of different heights can allow users to perform cell cultures in the bioreactor with different volumes of cell culture substrate, and allow for the unrestricted flow of media from the packed bed to the media outlet port. That is, a spacer 355 with a greater height can correspondingly reduce the height of the packed bed, while a spacer 355 with a lesser height can correspondingly allow more room for a taller packed bed. In some embodiments, the bioreactor system can include a spacer that has an adjustable height, rather than using separate spacers of different heights.

Figure 11A:
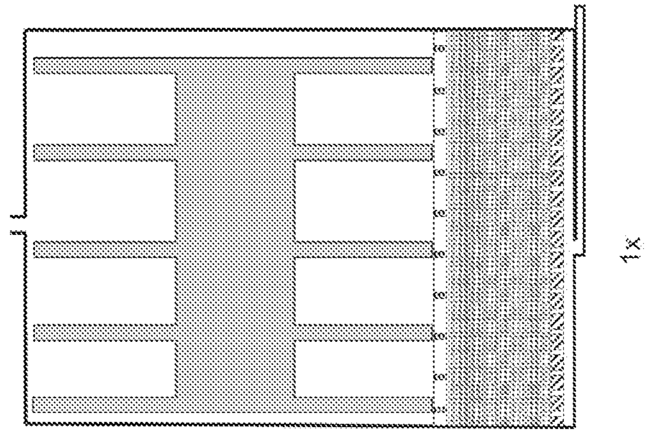
FIG. 11A is a cross-section view of the cell culture system with a spacer having a first height and cell culture matrix of a first height or thickness, according to one or more embodiments.
Figure 11B:
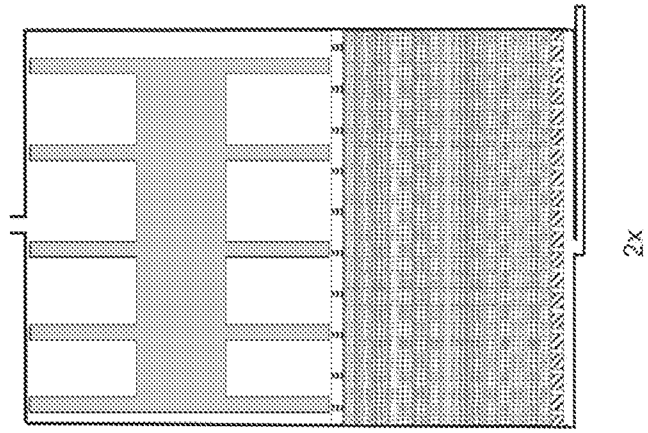
FIG. 11B is a cross-section view of the cell culture system with a spacer having a second height and cell culture matrix of a second height or thickness, according to one or more embodiments.
Figure 11C:
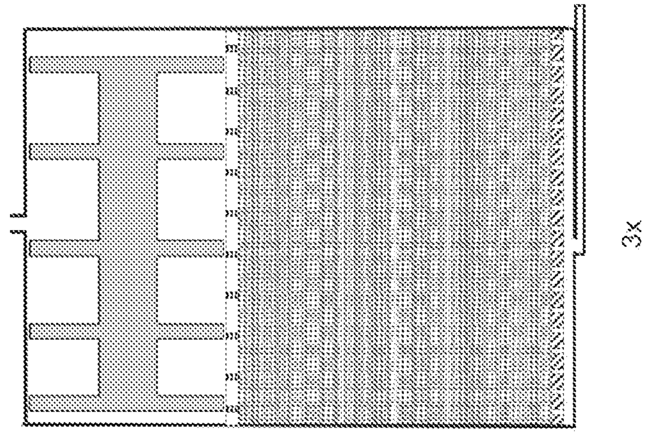
FIG. 11C is a cross-section view of the cell culture system with a spacer having a third height and cell culture matrix of a third height or thickness, according to one or more embodiments.

FIG. 11 shows examples of assembled packed-bed bioreactors with spacer inserts of different height, and correspondingly different heights for the packed bed substrate. From left to right, the same bioreactor can be configured to scale productivity 3× in this example. However, it is contemplated that embodiments of this disclosure will allow for even greater ranges of scaling up the productivity of a given bioreactor by adjusting the sizes of the components accordingly.

Figure 12:
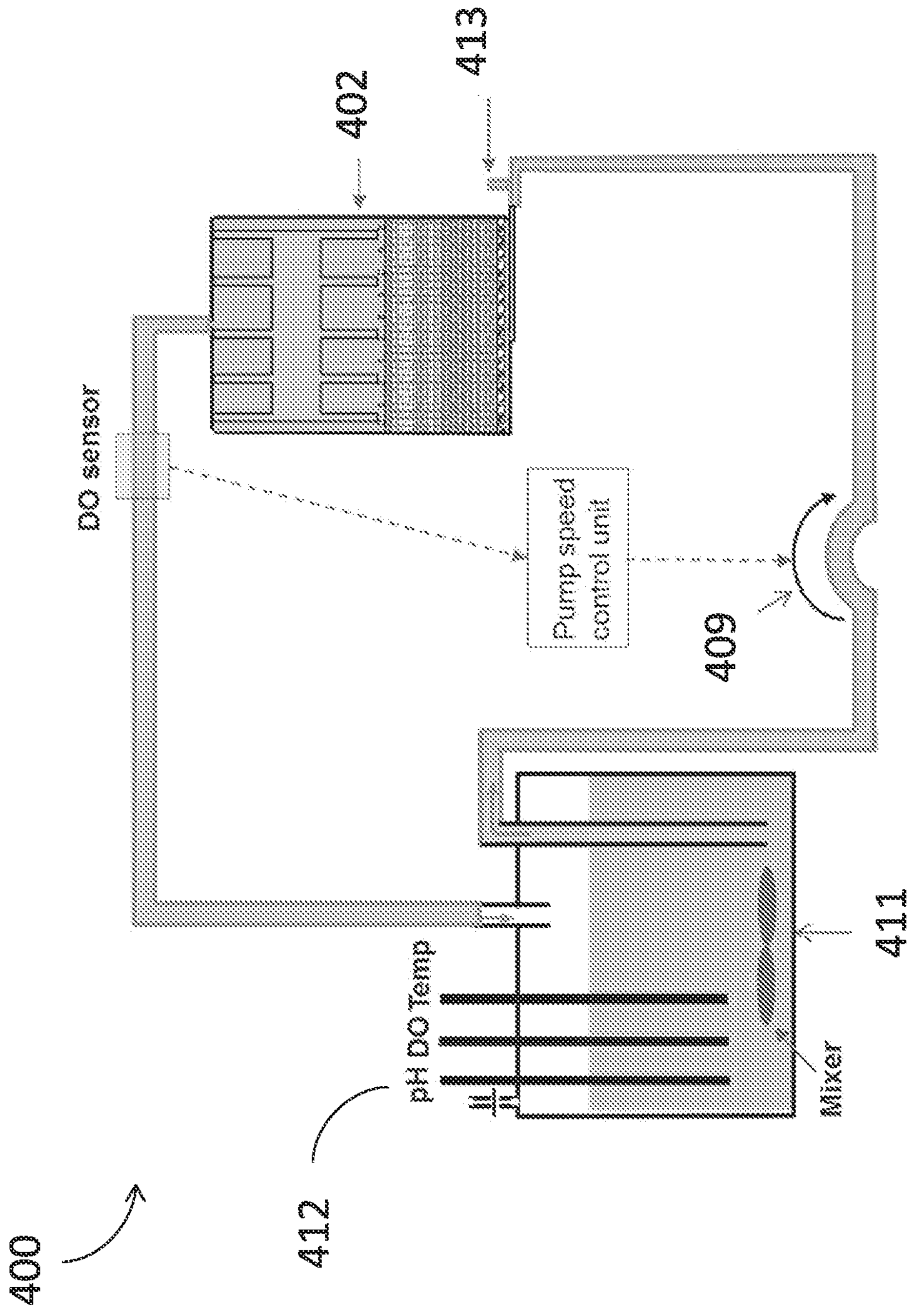
FIG. 12 is a schematic of a bioprocessing system incorporating a packed-bed cell culture system according to one or more embodiments.

FIG. 12 shows a bioreactor 402 incorporated into a bioprocessing system 400, according to one or more embodiments. The system 400 includes a media conditioning vessel 411 for proper maintenance of cell culture media parameters such as pH, temperature, and oxygenation level, for example. Automatically controlled pump 409 is used to perfuse media through the bioreactor 402. Bioreactor inlet 413 is equipped with additional 3-way port to facilitate cell inoculation or collection of harvested cells. The system 400 may include in-line sensors, as well as the sensors 412 in the media conditioning vessel 411.

Figure 13:
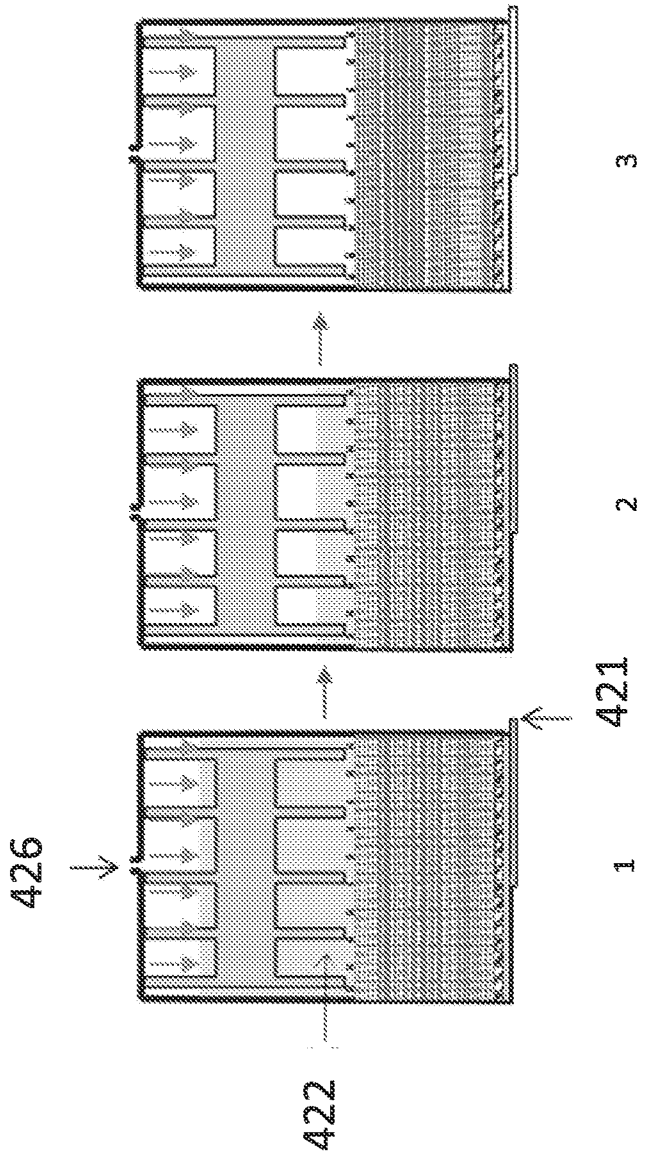
FIG. 13 shows cross-section views of a packed-bed cell culture system at three phases of a cell harvesting process, according to one or more embodiments.

FIG. 13 shows a bioreactor according to the above embodiments in multiple stages during a process of harvesting cells from the bioreactor. The cell harvesting process involves prefilling the bioreactor with a cell dissociation solution 422 and incubating the packed bed for a predetermined amount of time to detach cells from the substrate. The resulting suspension of cells is retrieved from the media inlet 421 by reversed flow of media/cells out through the inlet 421 with the application of pressurized fluid (e.g., air) in through the media outlet 426, as shown in the left to right progression of stages in FIG. 13.

Table 3 shows the results AAV production runs in 60 mm bioreactor in accordance with the embodiments of FIGS. 7-13. The 60 mm bioreactor corresponds to a total substrate surface area 6780 $cm^2$. Transfected cells yield, transfection efficiency and viral genome per $cm^2$ yield are shown.

Embodiments of the above scalable vessel of the present disclosure are targeting packed-bed bioreactor systems for anchorage dependent cells allowing process optimization or production at several different scales using the same platform and same bioreactor vessel. In one embodiment, for example, a bioreactor vessel 320 holds a packed bed 323 for adherent cells to attach, proliferate, transfect and produce products. Cell culture media can be continuously perfused through the packed bed and bioreactor vessel to supplement cells with oxygen and nutrients and to remove harmful metabolites. Media is introduced through the vessel inlet 321 at a calculated flow rate and leaves the bioreactor through the outlet 326. In order to achieve the uniform flow distribution across the packed substrate material, flow distribution plate 322 is positioned in front of the packed bed region. This flow distribution plate may have bifurcating or radially interconnected design allow the even distribution of flow across the packed bed in its entirety.

In another embodiment, layers of packed bed are retained in tightly packed state by a ridged retention grid 4. This retention grid has a large openings minimizing flow resistance during bioreactor perfusion, yet it is structurally stiff enough to uniformly exert pressure on a surface of packed bed to keep layers of PET mesh in tight packed. The volume of packed bed in the disclosed bioreactor can vary by utilizing spacers 5 of different dimensions to fix retention grid 4 in place. The size of bioreactor vessel and diameter of packed bed can vary from ~1 cm (laboratory scale) to ~10 cm (process development scale), to 50 cm (pilot scale) to 200 cm (manufacturing scale).

FIG. 8 shows parts of a bioreactor that was tested in bioproduction of viral particle by adherent HEK293T cells. The inner diameter of bioreactor packed bed region is 60 mm and the assembled state packed bed of bioreactor may consist of 10 to 300 layers of rigid PET substrate. This corresponds to 678-20300 $cm^2$ surface area available for adherent cells to attach, grow and produce compound of interest. FIG. 12 demonstrates schematics of bioreactor vessel 402 in assembled state that is connected to main external components comprised of a media conditioning vessel, a pump allowing the flow of media into the bioreactor and external dissolved oxygen sensor that support required process conditions for successful bioprocess. Cell culture media is conditioned in media conditioning vessel 411, where proper pH, temperature and dissolved oxygen levels are maintained. Subsequently media is perfused through the bioreactor by pump 409. Flow rate of pump 409 is integrated into a feedback loop which is automatically adjusts to maintain minimal predefined level of dissolved oxygen in media exiting the bioreactor. All transfection reagents, nutrients and additional media supplements required by given bioprocess can be introduced into bulk media and spent media can removed via the media conditioning vessel 411. At the end of the process, media can be drained from bioreactor and refilled with cells harvesting solution 422 (FIG. 13). After incubating the packed bed in harvesting solution for predefined time that is sufficient for cells to detach from the substrate cells are harvested by reverse flow through applying air pressure at bioreactor outlet 6 to achieve flow rate in a range of 70 ml/$cm^2$ (cross sectional packed bed area)/min. Cells are harvested at the bioreactor 3-way port 413. Cells can also be lysed directly in the bioreactor and lysate solution containing AVV particles can be collected through 3-way port 413.

The media conditioning vessel 404 can include sensors and control components found in typical bioreactor used in the bioprocessing industry for a suspension batch, fed-batch or perfusion culture. These include but are not limited to DO oxygen sensors, pH sensors, oxygenator/gas sparging unit, temperature probes, and nutrient addition and base addition ports. A gas mixture supplied to sparging unit can be controlled by a gas flow controller for $N_2$, $O_2$, and $CO_2$ gasses. The media conditioning vessel 404 also contains an impeller for media mixing. All media parameters measured by sensors listed above can be controlled by a media conditioning control unit 418 in communication with the media conditioning vessel 404, and capable of measuring and/or adjusting the conditions of the cell culture media 406 to the desired levels.

The media from the media 406 conditioning vessel 404 is delivered to the bioreactor 402 via an inlet, which may also include an injection port for cell inoculum to seed and begin culturing of cells. The bioreactor vessel 402 may also include on or more outlets through which the cell culture media exits the vessel 402. In addition, cells or cell products may be output through the outlet. To analyze the contents of the outflow from the bioreactor 402, one or more sensors 412 may be provided in the line. In some embodiments, the system 400 includes a flow control unit for controlling the flow into the bioreactor 402. For example, the flow control unit may receive a signal from the one or more sensors 412 and, based on the signal, adjust the flow into the bioreactor 402 by sending a signal to a pump (e.g., peristaltic pump) upstream of the inlet 408 to the bioreactor 402. Thus, based on one or a combination of factors measured by the sensors 412, the pump can control the flow into the bioreactor 402 to obtain the desired cell culturing conditions.

The media perfusion rate is controlled by the signal processing unit that collects and compares sensors signals from media conditioning vessel 404 and sensors located at the packed bed bioreactor outlet. Because of the pack flow nature of media perfusion through the packed bed bioreactor 402, nutrients, pH and oxygen gradients are developed along the packed bed. The perfusion flow rate of the bioreactor can be automatically controlled by the flow control unit operably connected to the peristaltic pump, according to the flow chart in FIG. 14B.

One or more embodiments of this disclosure offer a cell inoculation step that is different from conventional methods. In conventional methods, a pack bed with a conventional matrix is filled with culture media and concentrated inoculum is injected into the media circulation loop. The cell suspension is pumped through the bioreactor at increased flow rate to reduce nonuniformity of cell seeding via capture on the conventional packed bed matrix. In such conventional methods, the pumping of cells in the circulation loop at an elevated flow rate continues for perhaps several hours until the majority of the cells are captured in packed bed bioreactor. However, because of the nonuniform deep bed filtration nature of conventional packed bed bioreactors, cells are distributed nonuniformly inside the packed bed with the higher cell density at the inlet region of the bioreactor and lower cell density at the outlet region of the bioreactor.

In contrast, according to embodiments of the present disclosure, cell inoculum of equal volume to the void volume of the culture chamber in the bioreactor is directly injected into the packed bed through a cell inoculum injection port at the inlet of the bioreactor 402 (FIG. 12). The cell suspension is then uniformly distributed inside the packed bed because of uniform and continuous fluidic passages present in the cell culture matrix described herein. To prevent cells sedimentation due to gravity forces at the initial seeding stage, media perfusion can be started immediately after the inoculum injection. The perfusion flow rate is maintained below a preprogrammed threshold to balance the force of gravity and to avoid cells being washed from the packed bed bioreactor. Thus, at the initial cell attachment stage, cells are gently tumbled inside the packed bed and uniform cells distribution and attachment on available substrate surface is achieved.

Figure 14A:
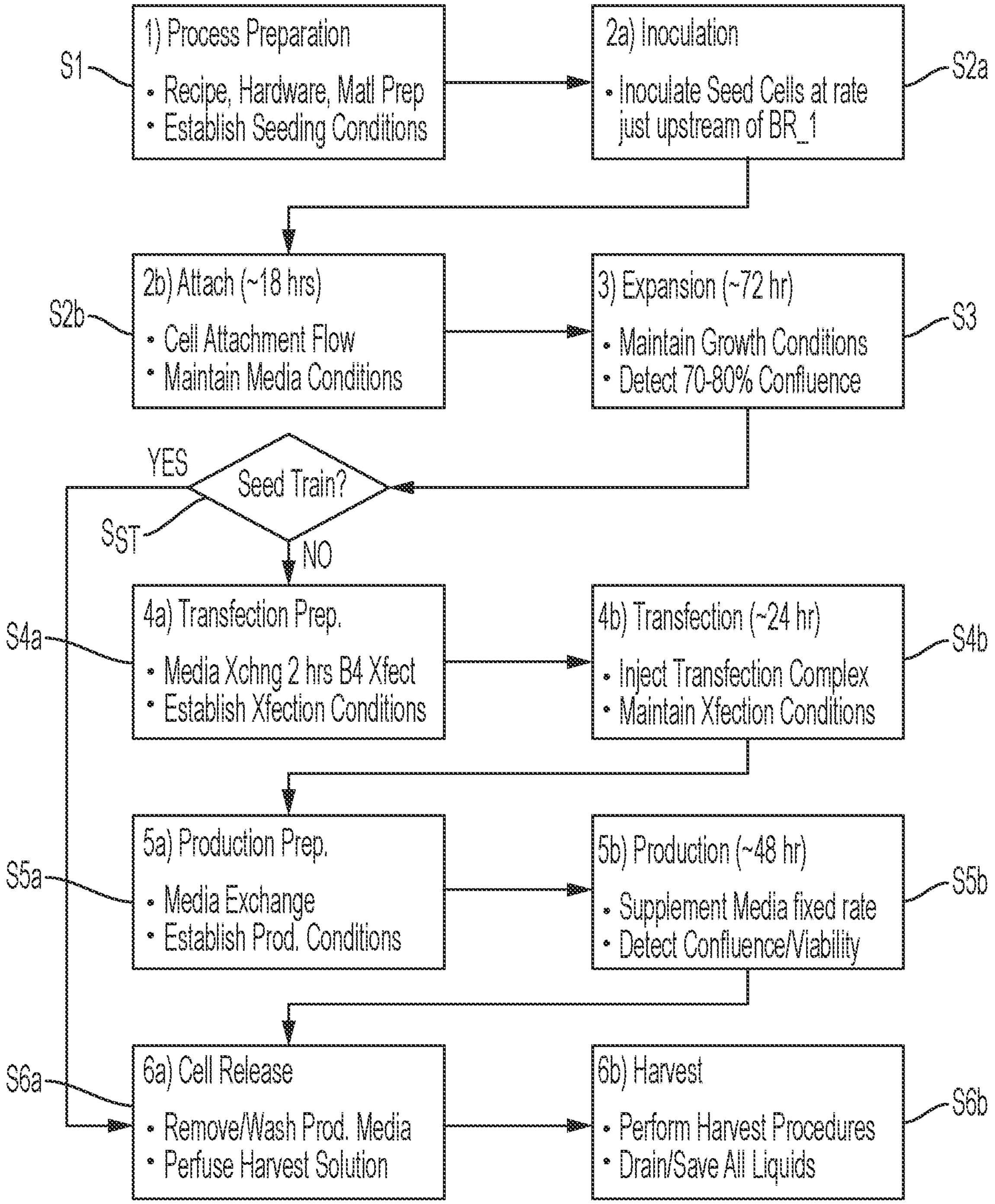
FIG. 14A is a process flow chart for culturing cells on a cell culture system, according to one or more embodiments.

FIG. 14A shows process steps used with a cell culture system as disclosed herein, according to some embodiments. As shown in FIG. 14A, these process steps can include process preparation (S1), seeding and attaching cells (S2*a*, S2*b*), cell expansion (S3), transfection (S4*a*, S4*b*), production of viral vector (S5*a*, S5*b*), and harvesting (S6*a*, S6*b*).

Figure 14B:
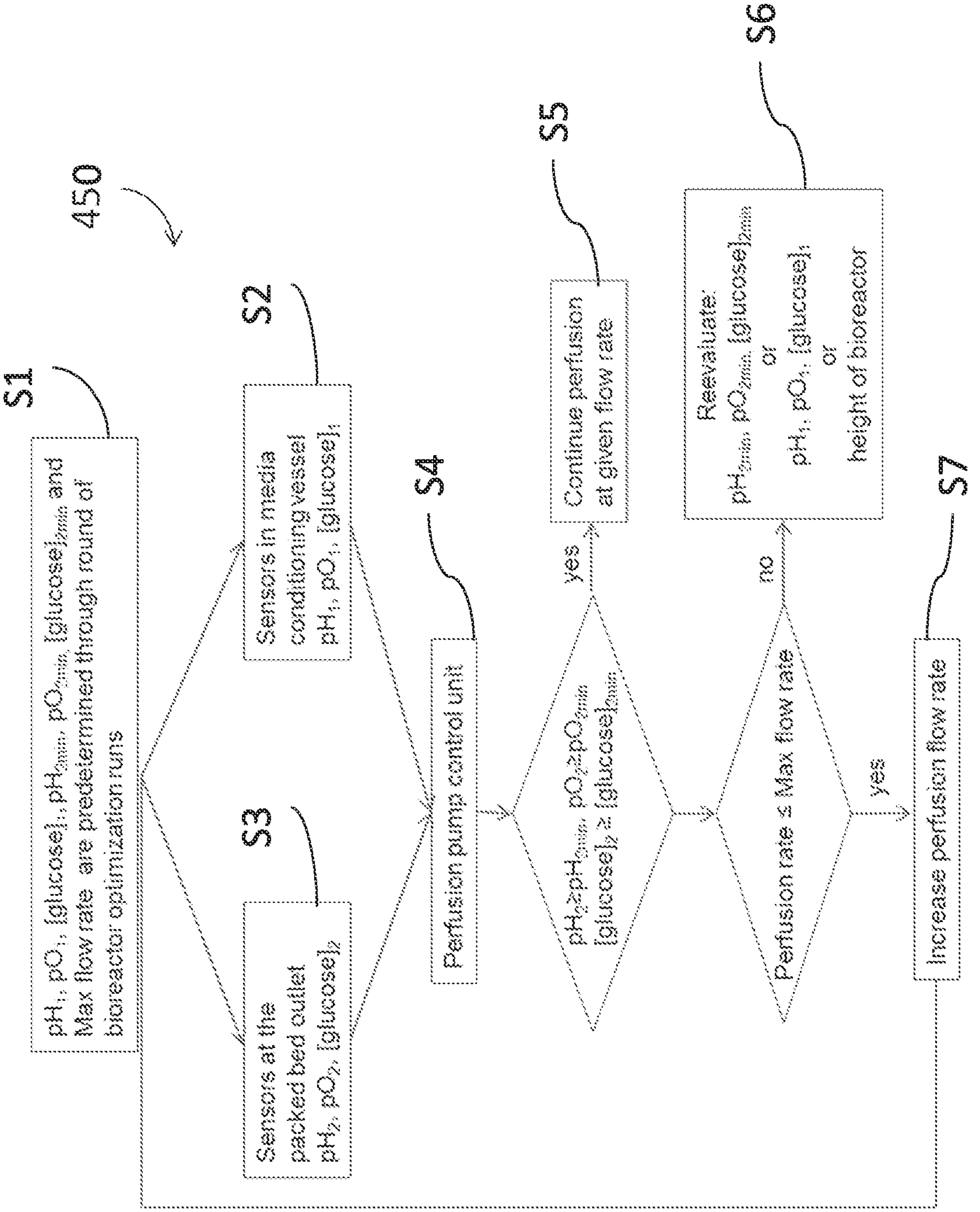
FIG. 14B is a flow chart for an operation for controlling a perfusion flow rate of a cell culture system, according to one or more embodiments.

FIG. 14B shows an example of a method 450 for controlling the flow of a perfusion bioreactor system, such as the system 400 of FIG. 12. According to the method 450, certain parameters of the system 400 are predetermined at step S1 through bioreactor optimization runs. From these optimization runs, the values of $pH_1$, $pO_1$, $[glucose]_1$, $pH_2$, $pO_2$, $[glucose]_2$, and maximum flow rate can be determined. The values for $pH_1$, $pO_1$, and $[glucose]_1$ are measured within the cell culture chamber of the bioreactor 402 at step S2, and $pH_2$, $pO_2$, and $[glucose]_2$ are measured by sensors 412 in the media conditioning vessel 404 at step S3. Based on these values at S2 and S3, a perfusion pump control unit makes determinations at S4 to maintain or adjust the perfusion flow rate. For example, a perfusion flow rate of the cell culture media to the cell culture chamber may be continued at a present rate if at least one of $pH_2 \geq pH_{2min}$, $pO_2 \geq pO_{2min}$, and $[glucose]_2 \geq [glucose]_{2min}$ (S5). If the current flow rate is less than or equal to a predetermined max flow rate of the cell culture system, the perfusion flow rate is increased (S7). Further, if the current flow rate is not less than or equal to the predetermined max flow rate of the cell culture system, a controller of the cell culture system can reevaluate at least one of: (1) $pH_{2min}$, $pO_{2min}$, and $[glucose]_{2min}$; (2) $pH_1$, $pO_1$, and [glucose]1; and (3) a height of the bioreactor vessel (S6).

The cell culture matrix can be arranged in multiple configurations within the culture chamber depending on the desired system. For example, in one or more embodiments, the system includes one or more layers of the substrate with a width extending across the width of a defined cell culture space in the culture chamber. Multiple layers of the substrate may be stacked in this way to a predetermined height. The substrate layers may be arranged such that the first and second sides of one or more layers are perpendicular to a bulk flow direction of culture media through the defined culture space within the culture chamber. In some embodiments, the first and second side of one or more layers may be parallel to the bulk flow direction. In one or more embodiments, the cell culture matrix includes one or more substrate layers at a first orientation with respect to the bulk flow, and one or more other layers at a second orientation that is different from the first orientation. For example, various layers may have first and second sides that are parallel or perpendicular to the bulk flow direction, or at some angle in between.

In one or more embodiments, the cell culture system includes a plurality of discrete pieces of the cell culture substrate in a packed bed configuration, where the length and or width of the pieces of substrate are small relative to the culture chamber. As used herein, the pieces of substrate are considered to have a length and/or width that is small relative to the culture chamber when the length and/or width of the piece of substrate is about 50% or less of the length and/or width of the culture space. Thus, the cell culture system may include a plurality of pieces of substrate packed into the culture space in a desired arrangement. The arrangement of substrate pieces may be random or semi-random, or may have a predetermined order or alignment, such as the pieces being oriented in a substantially similar orientation (e.g., horizontal, vertical, or at an angle between 0° and 90° relative to the bulk flow direction).

The "defined culture space," as used herein, refers to a space within the culture chamber occupied by the cell culture matrix and in which cell seeding and/or culturing is to occur. The defined culture space can fill approximately the entirety of the culture chamber, or may occupy a portion of the space within the culture chamber. As used herein, the "bulk flow direction" is defined as a direction of bulk mass flow of fluid or culture media through or over the cell culture matrix during the culturing of cells, and/or during the inflow or outflow of culture media to the culture chamber.

In one or more embodiments, the cell culture matrix is secured within the culture chamber by a fixing mechanism. The fixing mechanism may secure a portion of the cell culture matrix to a wall of the culture chamber that surrounds the matrix, or to a chamber wall at one end of the culture chamber. In some embodiments, the fixing mechanism adheres a portion of the cell culture matrix to a member running through the culture chamber, such as member running parallel to the longitudinal axis of the culture chamber, or to a member running perpendicular to the longitudinal axis. However, in one or more other embodiments, the cell culture matrix may be contained within the culture chamber without being fixedly attached to the wall of the chamber or bioreactor vessel. For example, the matrix may be contained by the boundaries of the culture chamber or other structural members within the chamber such that the matrix is held within a predetermined area of the bioreactor vessel without the matrix being fixedly secured to those boundaries or structural members.

One aspect of some embodiments provides a bioreactor vessel in a roller bottle configuration. The culture chamber is capable of containing a cell culture matrix and substrate according to one or more of the embodiments described in this disclosure.

In the roller bottle configuration, the bioreactor vessel may be operably attached to a means for moving the bioreactor vessel about a central longitudinal axis of the vessel. For example, the bioreactor vessel may be rotated about the central longitudinal axis. The rotation may be continuous (e.g., continuing in one direction) or discontinuous (e.g., an intermittent rotation in a single direction or alternating directions, or oscillating in back and forth rotational directions). In operation, the rotation of the bioreactor vessel causes movement of cells and/or fluid within the chamber. This movement can be considered relative with respect to the walls of the chamber. For example, as the bioreactor vessel rotates about its central longitudinal axis, gravity may cause the fluid, culture media, and/or unadhered cells to remain toward a lower portion of the chamber. However, in one or more embodiments, the cell culture matrix is essentially fixed with respect to the vessel, and thus rotates with the vessel. In one or more other embodiments, the cell culture matrix can be unattached and free to move to a desired degree relative to the vessel as the vessel rotates. The cells may adhere to the cell culture matrix, while the movement of the vessel allows the cells to receive exposure to both the cell culture media or liquid, and to oxygen or other gases within the culture chamber.

By using a cell culture matrix according to embodiments of this disclosure, such as a matrix including a woven or mesh substrate, the roller bottle vessel is provided with an increased surface area available for adherent cells to attach, proliferate, and function. In particular, using a substrate of a woven mesh of monofilament polymer material within the roller bottle, the surface area may increase by of about 2.4 to about 4.8 times, or to about 10 times that of a standard roller bottle. As discussed herein, each monofilament strand of the mesh substrate is capable of presenting itself as 2D surface for adherent cells to attach. In addition, multiple layers of mesh can we arranged in roller bottle, resulting in increases of total available surface area ranging from about 2 to 20 times that of a standard roller bottle. Thus, existing roller bottle facilities and processing, including cell seeding, media exchange, and cell harvesting, can be modified by the addition of the improved cell culture matrix disclosed herein, with minimal impact on existing operation infrastructure and processing steps.

The bioreactor vessel optionally includes one or more outlets capable of being attached to inlet and/or outlet means. Through the one or more outlets, liquid, media, or cells can be supplied to or removed from the chamber. A single port in the vessel may act as both the inlet and outlet, or multiple ports may be provided for dedicated inlets and outlets.

Embodiments are not limited to the vessel rotation about a central longitudinal axis. For example, the vessel may rotate about an axis that is not centrally located with respect to the vessel. In addition, the axis of rotation may be a horizontal or vertical axis.

Examples

To demonstrate the efficacy of the cell culture matrix, cell culture systems, and related methods of this disclosure, studies were conducted on the seeding and culturing of cells, according to the following examples.

Figure 15A:
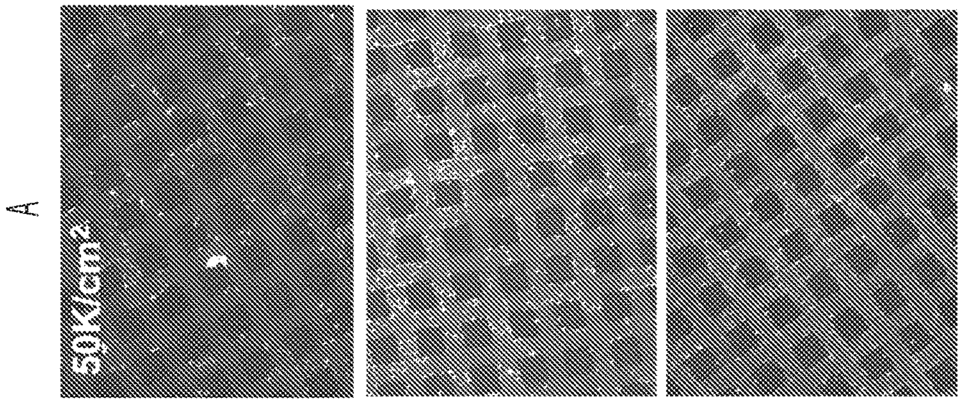
FIG. 15A is a micrograph of stained HEK293T cells on a cell culture substrate, where the cells were seeded at a first cell seeding density, according to one or more embodiments.
Figure 15B:
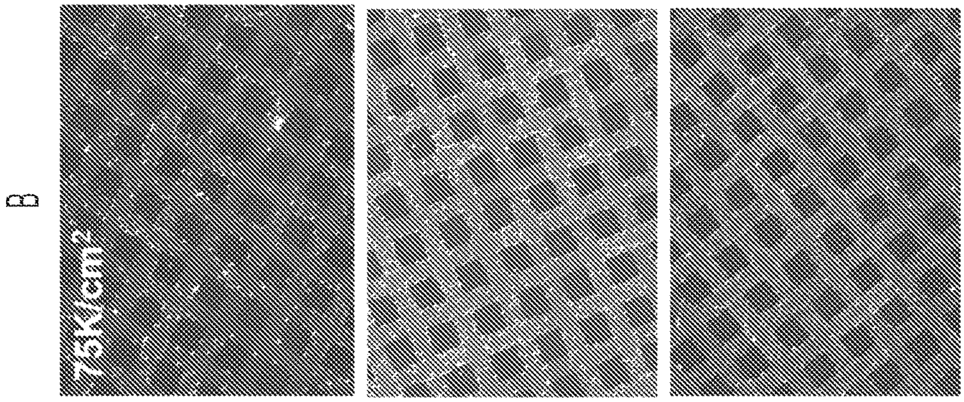
FIG. 15B is a micrograph of stained HEK293T cells on a cell culture substrate, where the cells were seeded at a second cell seeding density, according to one or more embodiments.
Figure 15C:
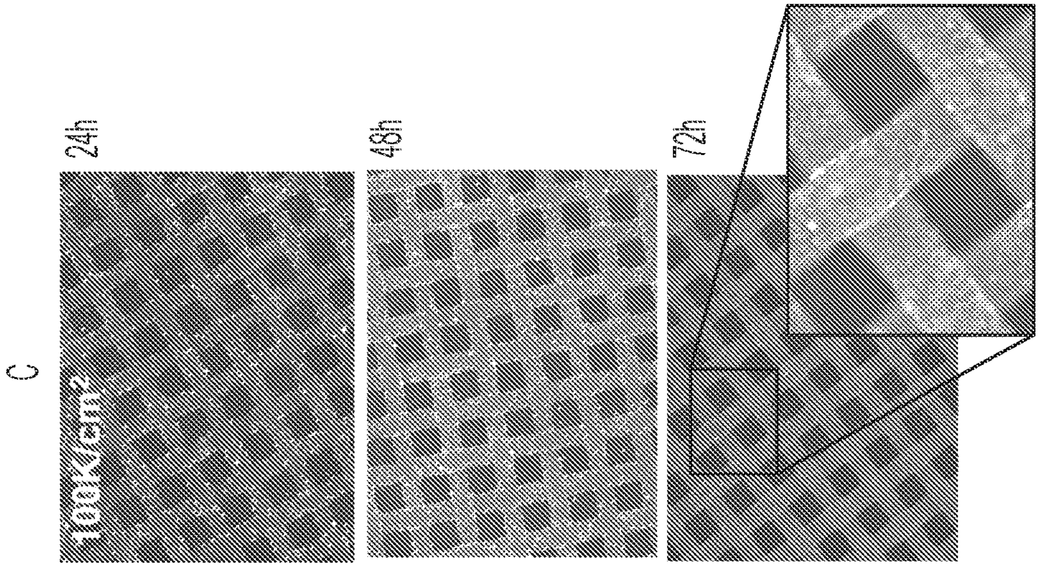
FIG. 15C is a micrograph of stained HEK293T cells on a cell culture substrate, where the cells were seeded at a third cell seeding density, according to one or more embodiments.

In Example 1, a cell culture matrix having a polyethylene terephthalate (PET) woven mesh substrate (see FIGS. 15A-15C) was tested in static cell culture conditions. The PET mesh was washed in ethanol and plasma treated in oxygen RF plasma. Gelatin was adsorbed on the surface of the mesh filaments to promote cell adhesion. Disc-shaped pieces of the mesh were placed into Corning® ultra-low attachment (ULA) 6-well plates. HEK293T cells were seeded onto the mesh discs at different seeding densities (50K per $cm^2$, 75K per cm 2, 100K per $cm^2$, corresponding to FIGS. 15A, 15B, and 15C, respectively) and cell culturing was performed for three days. Cells on the filament surfaces were stained with fluorescent Green Cell tracker dye. FIGS. 15A-15C show the results of this visualization of cells on the filament surfaces. The size of the mesh filaments relative to the size of the cells allows for the monofilament fibers to effectively act as a two-dimensional surface for cell attachment and proliferation. Cell proliferation was measured by harvesting cells from the mesh and counting on a Vi-Cell® cell counter from Beckman Coulter. The results showed good cell attachment and proliferation on the cell culture matrix under static cell culture conditions.

In Example 2, cells were cultured in a packed bed bioreactor system, such as the one shown in FIG. 6, according to an example of an embodiment of this disclosure. The packed bed has a cylindrical shape and is made of a stack of cell culture substrates, each of a circular or disk shape. Specifically, in Example 2, the packed bed had a height of about 25 mm, and included one hundred discs of PET mesh substrate, each having a diameter of about 20 mm. The mesh used corresponds to Mesh C in Table 1. It is estimated that the total two-dimensional surface area available for cell attachment was about 760 $cm^2$. To inoculate the bioreactor, 8 ml of an HEK293T cell suspension (2 million cells/ml) was injected directly into packed bed. Media perfusion started immediately after introduction of the cell suspension, with a perfusion flow rate set to 3 ml/min. Perfusion at this flow rate continued for 24 hours and then the flow rate was reduced to 1 ml/min. After this, the perfusion flow rate was adjusted to maintain $pO_2 \geq 50\%$ saturation, and pH≥7 at the outlet of the bioreactor. After two to three days, bioreactor run cells were stained with crystal violet and the bioreactor was disassembled to verify uniformity of cells attachment within the matrix. According to preferred embodiments, a bioreactor can be seeded by a seeding method in which cells are continuously tumbled inside the packed bed during the initial attachment stage. As a result, uniform cells distribution is achieved in all parts of packed bed after two days of cell culture. This indicates uniform cells distribution was achieved when the bioreactor was continuously perfused at the cell seeding stage.

In Example 3, cells were cultured in a packed bed bioreactor system, and transfection of HEK293T cells was performed for adeno-associated virus (AAV) production in the bioreactor. The same bioreactor setup as Example 2 was used in Example 3 (see, e.g., FIG. 6). The packed bed contained 100 disks of PET mesh (Mesh C of Table 1). A diameter of each disk was about 20 mm, and the bed height was about 25 mm, with a total of about 760 $cm^2$ of two-dimensional surface area available for cell attachment and proliferation. To inoculate the bioreactor, 8 ml of an HEK293T cell suspension (2 million cells/ml) was injected directly into packed bed. A media storage vessel containing about 50 ml of media attached to the bioreactor vessel. For 72 hours, cells were cultured in Dulbecco's Modified Eagle's Medium (DMEM) ATCC® media, with +10% FBS and +6 mM L-Glutamine. Media was replaced with a fresh media supply when the pH of the media in a storage vessel dropped below 7. Perfusion flow rate was adjusted accordingly to maintain $pO_2 \geq 50\%$ saturation, and pH ≥7 at the outlet of the bioreactor. After 72 hours, culture medium was changed with 50 ml of Corning® DMEM (15-018) with +10% FBS, +6 mM L-Glutamine, and transfection reagents were added to a final concentration of 2 ug/ml of AAV2 and PEIpro® at a 1:2 ratio. During the next 72 hours, culture medium was changed to a fresh supply if pH in a storage bottle dropped below 7. Perfusion flow rate was adjusted accordingly to maintain $pO_2 \geq 50\%$ saturation and pH ≥7 at the outlet of the bioreactor. Cells were harvested by using 5× TrypLE™. Transfection efficiency was analyzed by fluorescent flow cytometer, viral particle and viral genome titer were analyzed by ELISA and PCR assays. Cell culture results are presented in Table 2, where "VP" stands for viral protein, and "GC" stands for genome copies.

TABLE 2

Transfection of HEK 293T cells and AAV production in packed bed bioreactor results.

| Sample No. | Total harvested cell/$cm^2$ (viability %) | Transfection efficiency (%) | VP/ cell | VP/ cm2 | GC/ cell | GC/ cm2 |
|---|---|---|---|---|---|---|
| 1 | 188913 (92%) | 90.5 | 2.1e4 | 4.03e9 | 1.6e4 | 3e9 |
| 2 | 331104 (95%) | 88.2 | 2.3e4 | 7.6e9 | 1.5e4 | 4.8e9 |

The embodiments disclosed herein have advantages over the existing platforms for cell culture and viral vector production. It is noted that the embodiments of this disclosure can be used for the production of a number of types of cells and cell byproducts, including, for example, adherent or semi-adherent cells, Human embryonic kidney (HEK) cells (such as HEK23), including transfected cells, viral vectors, such as Lentivirus (stem cells, CAR-T) and Adeno-associated virus (AAV). These are examples of some common applications for a bioreactor or cell culture substrate as disclosed herein, but are not intended to be limiting on the use or applications of the disclosed embodiments, as a person of ordinary skill in the art would understand the applicability of the embodiments to other uses.

Figure 16A:
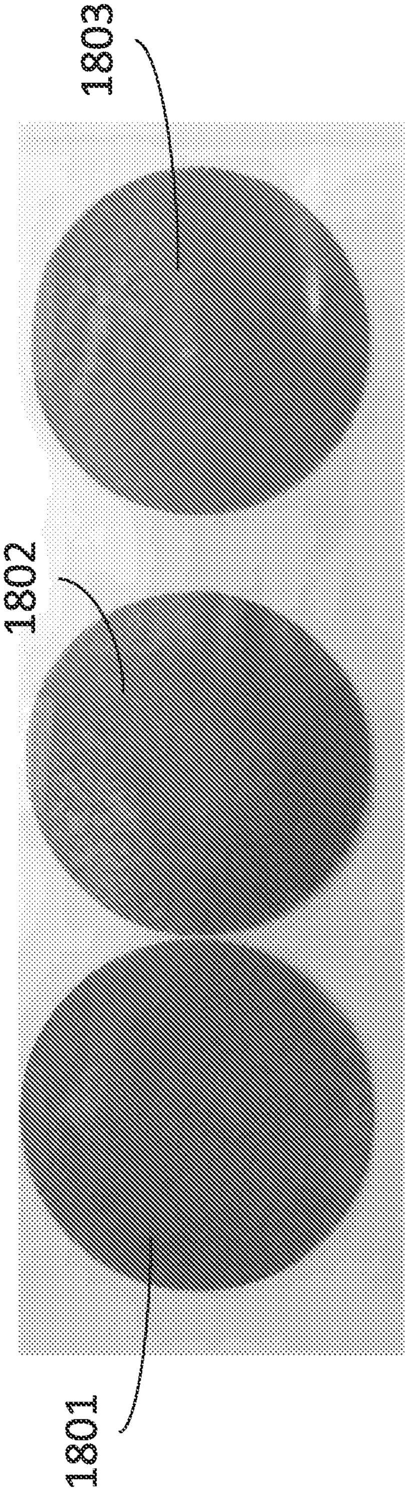
FIG. 16A is a photograph of disks of a cell culture matrix with stained cells after cell culture in a packed-bed bioreactor but perform a cell harvesting operation is performed on the cell culture substrate, according to one or more embodiments.

As discussed above, one advantage of embodiments of this disclosure is the flow uniformity through the cell culture substrate. Without wishing to be bound by theory, it is believed that the regular or uniform structure of the cell culture substrate provides a consistent and uniform body through which media can flow. In contrast, existing platform predominately rely on irregular or random substrates, such as felt-like or non-woven fibrous materials. The uniform properties of the substrate of this disclosure can be illustrated by examining the uniform and consistent cell seeding that is achieved on the substrate. FIG. 16A, for example, shows three disks (1801, 1802, 1803) of substrate material according to some embodiments of this disclosure. The disks in FIG. 16A are a woven PET mesh material as described herein, and each have a diameter of about 60 mm. The surface area for a bioreactor packed with 10 to 300 layers of similar disks would be about 678 to 20,300 $cm^2$. In this example, cell culture was performed using a stack of 100 disks. The first disk 1801 was the top disk in a stack of such disks within a bioreactor, the second disk 1802 was the middle disk of the stack, and the third disk 1803 was the bottom disk of the stack.

Figure 16B:
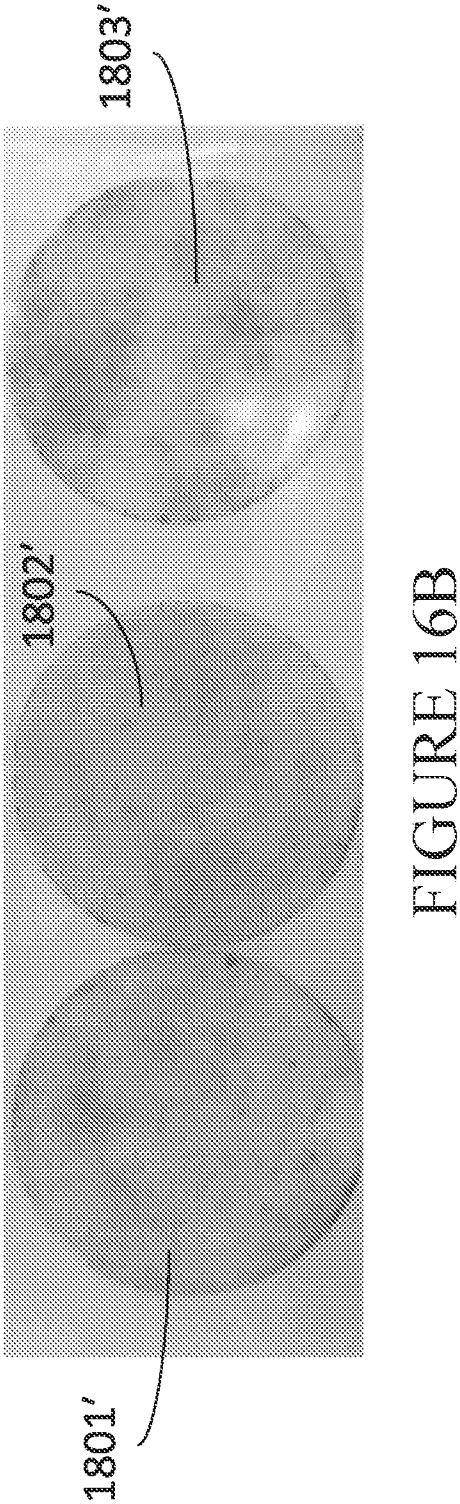
FIG. 16B is a photograph of disks of a cell culture matrix with stained cells after cell culture in a packed-bed bioreactor and after performing a cell harvesting operation on the cell culture substrate, according to one or more embodiments.

FIG. 16A demonstrates uniformity of cells distribution inside the bioreactor 72 h post inoculation. Substrate layers from three different regions of packed bed were retrieved from bioreactor and crystal violet stained to visualize attached HEK 293T cells. Stain uniformity of top, middle and bottom layers cells demonstrated that cells were uniformly distributed throughout the packed bed during seeding and attachment steps. Packed bed substrate samples also were stained post-harvest to confirm the efficiency of cells harvested from disclosed bioreactor (see FIG. 16B). FIG. 16B demonstrates stained substrate layer retrieved from three different zones of packed bed after harvest step. As can be seen from FIG. 16B harvesting process delivered more than 95% cells recovery from the bioreactor. Cell culture results are presented in Table 3.

In the experiment that produced the images in FIGS. 16A and 16B, the bioreactor was prefilled with cell culture media and system was preconditioned overnight to achieve a steady state of pH 7.2, DO. 100%, and 37° C. 400 ml of ATCC DMEM media+10% FBS+6 mM L-Glutamine was used to fill the entire bioreactor system. 30 ml of HEK293T cells in suspension (5 million cells/mL) was injected directly into the packed bed though 3-way port to form inoculation. The bioreactor was perfused with preconditioned media at rate of 30 mL/min for the first 48 h to allow uniform cell distribution, attachment and initial growth in the packed bed. After 48 h of culture 200 ml of fresh complete ATCC DMEM media was added into the system to maintain glucose level above 1 g/L. Perfusion flow rate was adjusted automatically to maintain DOexternal≥45% of media saturation at the bioreactor outlet. 72 hours post inoculation, the culture medium was exchanged with 500 ml of Corning DMEM (15-018)+10% FBS+6 mM L-Glutamine and allowed to perfuse for 2 hours. A transfection mix (complexes of plasmid DNA and PEI at 1:2 ratio; 0.8 ug of total DNA/million cells) was added to a final concentration of 2 μg total DNA/ml of medium 24 hours post-transfection, and culture medium was exchanged with 500 ml of fresh complete Corning DMEM (15-018) medium to replenish spent nutrients. The perfusion flow rate was adjusted automatically to maintain $DO_{external}$≥45% saturation at the outlet of the bioreactor. Glucose level was monitored during subsequent 48 hours of culture and supplemented through media addition or exchange as needed to maintain levels above 0.3 g/L. At 72 hours post-transfection, cells were washed with DPBS and harvested by using 1× Accutase solution. Transfection efficiency was analyzed by fluorescent flow cytometry, and viral particle and viral genome titer were analyzed by ELISA and qPCR assays.

Crystal violet staining was used to highlight the uniform growth of cells over the entire surface of the disks in FIG. 16A. Despite the first disk 1801, second disk 1802, and third disk 1803 being spread throughout the stack of the cell culture matrix, the cell growth is consistent across all three disks. The image in FIG. 16A was taken after a 72-hour culture and before the cells were harvested from the substrate. FIG. 16B shows the same three disks after the cells have been harvested (1801', 1802', and 1803'). As shown by the relative absence of crystal staining in FIG. 16B, the cells have been harvested uniformly across the surface of each disk and across the three disks of the cell culture matrix stack. Based on analysis, more than 95% of cells were recovered from the bioreactor. The cell culture results of the AAV production in these 60 mm diameter substrate stacks/vessels with a total surface area of 6780 $cm^2$ are shown below in Table 3, which shows the transfected cell yield, transfection efficiency, and viral genome per $cm^2$ yield. Again, the uniform structure of the substrate and the uniform flow characteristics are believed to contribute to this efficient and uniform growth and harvest capability.

TABLE 3

Transfected cell yield, transfection efficiency, and viral genome per $cm^2$ yield from 60 mm bioreactor.

| | Cells/$cm^2$ at harvest | % GFP+ cells | Bulk AAV VG/$cm^2$ |
|---|---|---|---|
| Reactor 1 | 432,153 | 94 | $3.19 \times 10^{10}$ |
| Reactor 2 | 479,351 | 87 | $2.98 \times 10^{10}$ |
| Reactor 3 | 395,062 | 88.5 | TBD |

Table 4 below shows the above results in the context of multiple experiments including bioreactor vessels of different diameters (29 mm and 60 mm). The data shows good scalability between smaller (e.g., 29 mm diameter, 1600 $cm^2$ surface area) and larger (e.g., 60 mm diameter, 6780 $cm^2$ surface area) vessels and/or packed bed matrices.

TABLE 4

Consistent results across bioreactor size.

| Vessel diameter (SA in $cm^2$) | Cells/$cm^2$ at harvest | % GFP+ cells | Bulk AAV VG/$cm^2$ |
|---|---|---|---|
| 29 mm (1600 $cm^2$) | 407,500 | 89.9 | 1.74E+10 |
| 29 mm (1600 $cm^2$) | 373,125 | 93.4 | 3.00E+10 |
| 29 mm (1600 $cm^2$) | 376,250 | 89.3 | 2.16E+10 |
| 60 mm (5425 $cm^2$) | 405,529 | 87.8 | 1.97E+10 |
| 60 mm (6780 $cm^2$) | 357,832 | 92.3 | N/A |
| 60 mm (6780 $cm^2$) | 432,153 | 94 | 3.19E+10 |
| | 479,351 | 87 | 2.98E+10 |
| 60 mm (6780 $cm^2$) | 395,062 | 88.5 | TBD |

Example. AAV production by HEK 293T cells in 60 mm bioreactor unit and AAV production in packed bed bioreactor.

Packed bed bioreactor was assembled in alpha unit as presented in FIG. 7. Actual bioreactor parts are shown in FIG. 8. A 60 mm diameter packed bed contained 100 layers of structured and treated PET substrate was placed in the bioreactor. The packed bed height was 26 mm, and total 2D surface area available for cell attachment and proliferation was calculated to be 6780 $cm^2$. The bioreactor was prefilled with cell culture media and system was preconditioned overnight to achieve a steady state of pH 7.2, D.O. 100%, and 37° C. 400 ml of ATCC DMEM media+10% FBS+6 mM L-Glutamine was used to fill the entire bioreactor system (FIG. 12). 30 ml of HEK293T cells in suspension (5 Million cells/mL) was injected directly into the packed bed though 3-way port 413 to for inoculation.

The bioreactor was perfused with preconditioned media at rate of 30 mL/min for the first 48 hours to allow uniform cell distribution, attachment and initial growth in the packed bed. After 48 hours of culture 200 ml of fresh complete ATCC DMEM media was added into the system to maintain glucose level above 1 g/L. Perfusion flow rate was adjusted automatically to maintain $DO_{external}$≥45% of media saturation at the bioreactor outlet.

72 hours post inoculation, the culture medium was exchanged with 500 ml of Corning DMEM (15-018)+10% FBS+6 mM L-Glutamine and allowed to perfuse for 2 hours. Transfection mix (complexes of plasmid DNA and PEI at 1:2 ratio; 0.8 ug of total DNA/million cells) was added then to final concentration 2 ug total DNA/ml of medium 24 hour post transfection, culture medium was exchanged with 500 ml of fresh complete Corning DMEM (15-018) medium to replenish spent nutrients. The perfusion flow rate was adjusted automatically to maintain $DO_{external}$≥45% saturation at the outlet of the bioreactor.

Glucose level was monitored during subsequent 48 hours of culture and supplemented through media addition or exchange as needed to maintain levels above 0.3 g/L. At 72 h post transfection, cells were washed with DPBS and harvested by using 1× Accutase solution. Transfection efficiency was analyzed by fluorescent flow cytometry, viral particle and viral genome titer were analyzed by ELISA and qPCR assays. FIG. 16A demonstrates uniformity of cells distribution inside the bioreactor 72 h post inoculation. As can be seen from FIG. 16B, harvesting process delivered more than 95% cells recovery from the bioreactor. Cell culture results are presented in Table 3.

Figure 17A:
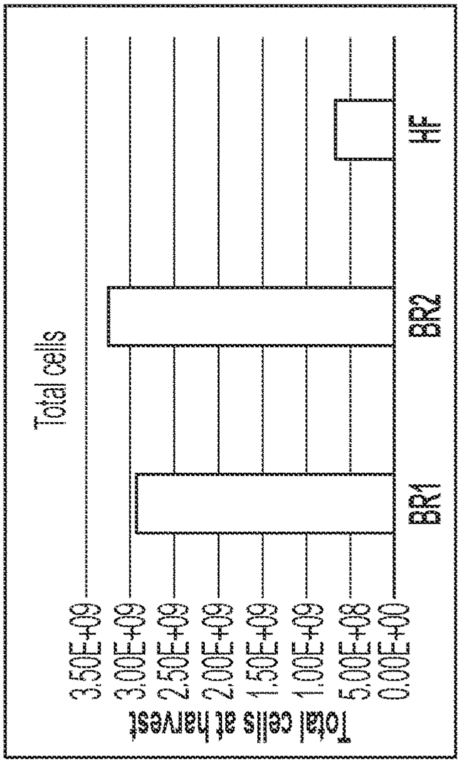
FIG. 17A is a bar graph showing experimental results of total cells harvested for two examples according to embodiments of this disclosure, as compared to cells cultured using a HYPERFlask®.
Figure 17B:
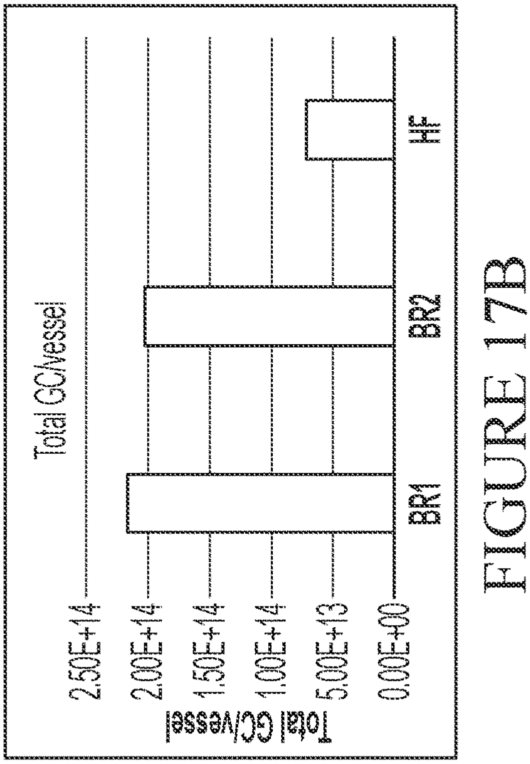
FIG. 17B is a bar graph showing experimental results of total genome copies per vessel for two examples according to embodiments of this disclosure, as compared to cells cultured using a HYPERFlask®.
Figure 17C:
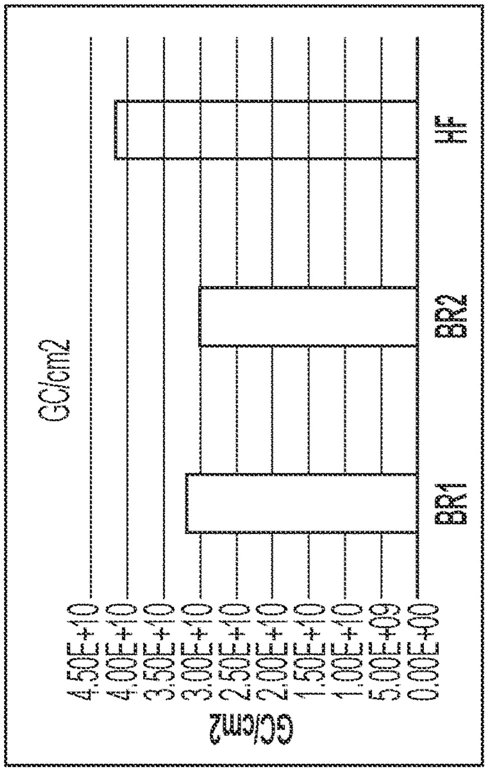
FIG. 17C is a bar graph showing experimental results of genome copies per surface area for two examples according to embodiments of this disclosure, as compared to cells cultured using a HYPERFlask®.

As discussed above, embodiments of this disclosure can provide a packed bed cell culture matrix and/or bioreactor capable of culturing a high density of cells in a relatively small and practical footprint. For example, the 60 mm cell culture matrix in the examples in Tables 3 and 4 above has a surface area of about 6870 $cm^2$. For reference, the Corning HYPERFlask® has a surface area of about 1720 $cm^2$. The 60-mm diameter cell culture matrix of Tables 3 and 4 can be housed in a bioreactor that is smaller than the HYPER-Flask®, but can nonetheless results in a higher cell count at harvest, higher number of total genome copies (GC, or viral genomes (VG) per vessel. FIGS. 17A, 17B, and 17C show data resulting from cell cultures in two bioreactor vessels according to this disclosure with 60-mm diameter substrates from Tables 3 and 4 compared to data from a cell culture on a 2D surface of the HYPERFlask®, including the GC per $cm^2$ (FIG. 17C), which, though lower than the HYPER-Flask® in this example, makes up for it with a higher surface area.

Figure 26:
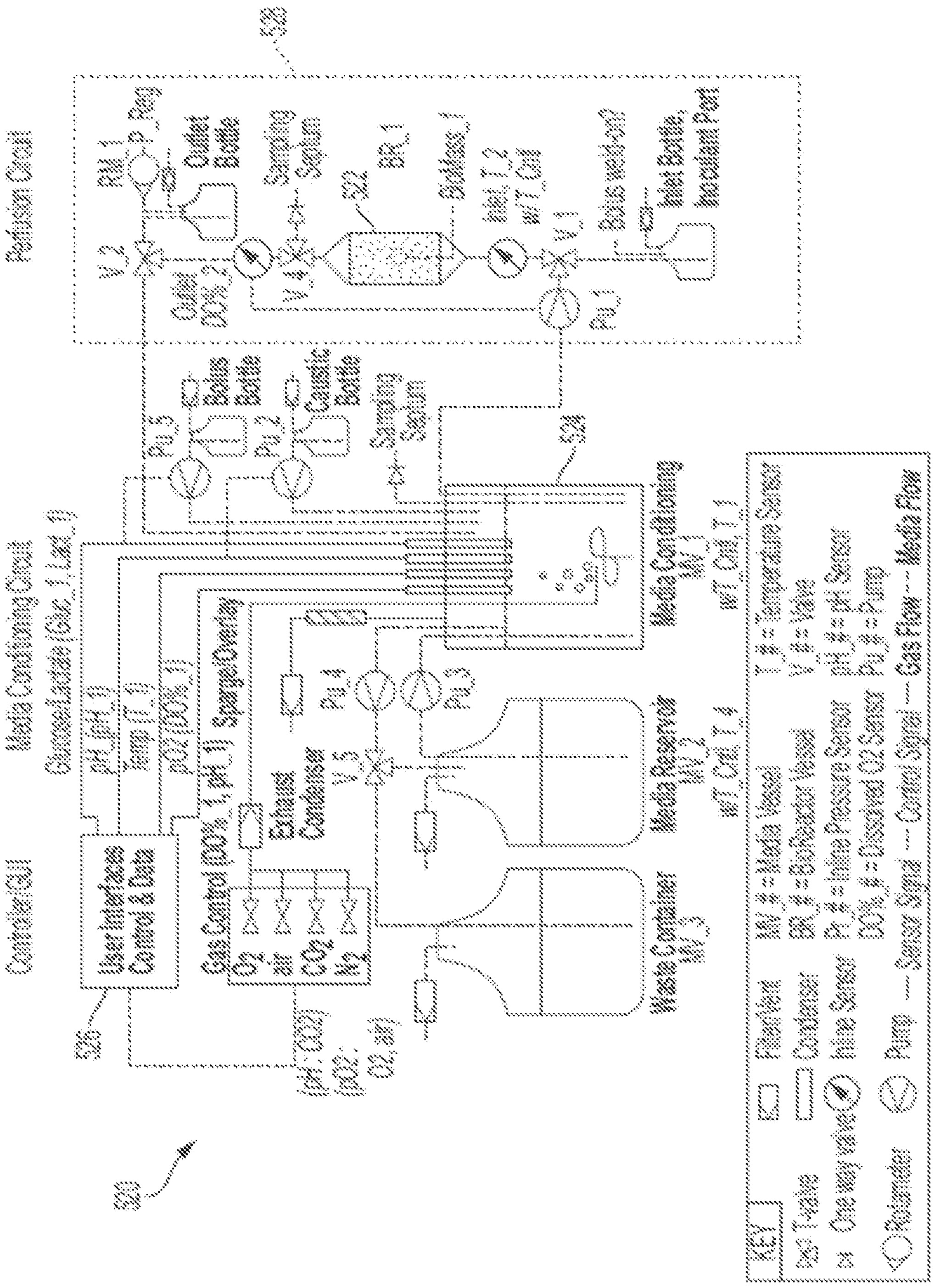
FIG. 26 is a detailed schematic of a cell culture system, according to one or more embodiments.

FIG. 26 shows a more detailed schematic of a cell culture system 520 according to one or more embodiments. The basic construction of the system 520 is similar to the system 400 in FIG. 12, with a packed bed bioreactor 522 having a vessel containing a packed bed of cell culture material, such as a PET woven mesh, and a separate media conditioning vessel 524. In contrast to system 400, however, system 520 shows the details of the system, including sensors, user interface and controls, and various inlet and outlets for media and cells. According to some embodiments, the media conditioning vessel 524 is controlled by the controller 526 to provide the proper temperature, pH, $O_2$, and nutrients. While in some embodiments, the bioreactor 522 can also be controlled by the controller 526, in other embodiments the bioreactor 522 is provided in a separate perfusion circuit 528, where a pump is used to control the flow rate of media through the perfusion circuit 528 based on the detection of O2 at or near the outlet of the bioreactor 522.

Illustrative Implementations

The following is a description of various aspects of implementations of the disclosed subject matter. Each aspect may include one or more of the various features, characteristics, or advantages of the disclosed subject matter. The implementations are intended to illustrate a few aspects of the disclosed subject matter and should not be considered a comprehensive or exhaustive description of all possible implementations.

Aspect 1 pertains to a cell culture system comprising: a bioreactor vessel; and a cell culture matrix disposed in the bioreactor vessel and configured to culture cells; wherein the cell culture matrix comprises a substrate comprising a first side, a second side opposite the first side, a thickness separating the first and second sides, and a plurality of openings formed in the substrate and passing through the thickness of the substrate, and wherein the plurality of openings is configured to allow flow of at least one of cell culture media, cells, or cell products through the thickness of the substrate.

Aspect 2 pertains to the cell culture system of Aspect 1, wherein the substrate comprises at least one of polystyrene, polyethylene terephthalate, polycarbonate, polyvinylpyrrolidone, polybutadiene, polyvinylchloride, polyethylene oxide, polypyrroles, and polypropylene oxide.

Aspect 3 pertains to the cell culture system of Aspect 1 or Aspect 2, wherein the substrate comprises at least one of a molded polymer lattice sheet, a 3D-printed lattice sheet, and a woven mesh sheet.

Aspect 4 pertains to the cell culture system of Aspect 3, wherein the substrate comprises the woven mesh comprising one or more fibers.

Aspect 5 pertains to the cell culture system of Aspect 4, wherein the one or more fibers comprise a cross-section shape that is at least one of flat, round, rectangular, or polygonal.

Aspect 6 pertains to the cell culture system of Aspect 4 or Aspect 5, wherein the one or more fibers comprises at least one of a monofilament fiber and a multifilament fiber.

Aspect 7 pertains to the cell culture system of any one of Aspects 4-6, wherein the one or more fibers comprises a first fiber with a first fiber diameter from about 50 μm to about 1000 μm, from about 50 μm to about 600 μm, from about 50 μm to about 400 μm, from about 100 μm to about 325 μm, or from about 150 μm to about 275 μm.

Aspect 8 pertains to the cell culture system of Aspect 7, wherein the one or more fibers further comprises a second fiber with a second fiber diameter from about 50 μm to about 1000 μm, from about 50 μm to about 600 μm, from about 50 μm to about 400 μm, from about 100 μm to about 325 μm, or from about 150 μm to about 275 μm.

Aspect 9 pertains to the cell culture system of Aspect 8, wherein the second fiber diameter is different than the first fiber diameter.

Aspect 10 pertains to the cell culture system of any one of Aspects 1-7, wherein the plurality of openings comprises an opening diameter of from about 100 μm to about 1000 μm, from about 200 μm to about 900 μm, or from about 225 μm to about 800 μm.

Aspect 11 pertains to the cell culture system of Aspect 10, wherein the fiber diameter is from about 250 μm to about 300 μm, and the opening diameter is from about 750 μm to about 800 μm, or wherein the fiber diameter is from about 270 μm to about 276 μm, and the opening diameter is from about 785 μm to about 795 μm.

Aspect 12 pertains to the cell culture system of Aspect 10, wherein the fiber diameter is from about 200 μm to about 230 μm, and the opening diameter is from about 500 μm to about 550 μm, or wherein the fiber diameter is from about 215 μm to about 225 μm, and the opening diameter is from about 515 μm to about 530 μm.

Aspect 13 pertains to the cell culture system of Aspect 10, wherein the fiber diameter is from about 125 μm to about 175 μm, and the opening diameter is from about 225 μm to about 275 μm, or wherein the fiber diameter is from about 150 μm to about 165 μm, and the opening diameter is from about 235 μm to about 255 μm.

Aspect 14 pertains to the cell culture system of any one of Aspects 10-13, wherein a ratio of the opening diameter to the fiber diameter is from about 1.0 to about 3.5, from about 1.25 to about 3.25, from about 1.4 to about 3.0, from about 1.5 to about 2.9, from about 1.5 to about 2.4, or from about 2.4 to about 2.9.

Aspect 15 pertains to the cell culture system of any one of Aspects 1-14, wherein the plurality of openings comprises openings with a shape that is square, rectangular, rhombus, rhomboid, circular, or oval.

Aspect 16 pertains to the cell culture system of any one of Aspects 1-15, wherein the plurality of openings is arrayed in a regular pattern.

Aspect 17 pertains to the cell culture system of any one Aspects 1-16, wherein the cell culture matrix comprises a monolayer substrate.

Aspect 18 pertains to the cell culture system of any one of Aspects 1-17, wherein the cell culture matrix comprises a multilayer substrate, the multilayer substrate comprising at least a first substrate layer and a second substrate layer, wherein the first substrate layer comprises a first side and a second side opposite to the first side, and the second substrate layer comprises a third side and a fourth side opposite to the third side, the second side facing the third side.

Aspect 19 pertains to the cell culture system of Aspect 18, wherein the multilayer substrate is configured so that the first substrate layer has a predetermined alignment with respect to the second substrate layer.

Aspect 20 pertains to the cell culture system of Aspect 19, wherein the multilayer substrate is configured so that an intersection of fibers on the first substrate layer faces an opening in the second substrate layer.

Aspect 21 pertains to the cell culture system of Aspect 19 or Aspect 20, wherein openings in the first substrate layer are at least partially overlapping with the openings in the second substrate layer.

Aspect 22 pertains to the cell culture system of Aspect 21, wherein the openings in the first and second substrate layers are aligned.

Aspect 23 pertains to the cell culture system of Aspect 18, wherein the multilayer substrate is configured so that the first substrate layer has a random alignment with respect to the second substrate layer.

Aspect 24 pertains to the cell culture system of any one of Aspects 1-23, wherein the cell culture matrix is disposed in the bioreactor vessel such that a bulk flow direction of media through the bioreactor vessel is parallel or perpendicular to the first and second sides.

Aspect 25 pertains to the cell culture system of any one of Aspects 1-24, wherein the cell culture matrix comprises a plurality of substrates randomly packed into the bioreactor vessel.

Aspect 26 pertains to the cell culture system of any one of Aspects 1-25, wherein the bioreactor vessel is a packed bed bioreactor.

Aspect 27 pertains to the cell culture system of any one of Aspects 1-26, wherein the bioreactor vessel comprises: a culture space disposed within the bioreactor vessel and containing the cell culture matrix, one or more openings configured to provide fluid to or remove fluid from the culture space.

Aspect 28 pertains to the cell culture system of Aspect 27, wherein the one or more openings comprise an inlet configured to provide fluid to an interior of the culture space, and an outlet configured to allow fluid to be removed from the culture space of the bioreactor vessel.

Aspect 29 pertains to the cell culture system of Aspect 28, wherein the bioreactor vessel comprises a first end comprising the inlet, a second end opposite the first end and comprising the outlet, the culture space being disposed between the first end and the second end.

Aspect 30 pertains to the cell culture system of Aspect 29, wherein the cell culture matrix has a shape corresponding to a shape of the culture space.

Aspect 31 pertains to the cell culture system of any one of Aspects 1-30, wherein the cell culture matrix comprises the polymer mesh material in a cylindrical roll configuration.

Aspect 32 pertains to the cell culture system of Aspect 31, wherein a central longitudinal axis of the cylindrical roll is parallel to a flow direction of the media.

Aspect 33 pertains to the cell culture system of Aspect 31 or Aspect 32, wherein the cylindrical roll is configured to expand to a shape of the culture space in the bioreactor vessel via an unraveling of the cylindrical roll.

Aspect 34 pertains to the cell culture system of any one of Aspects 31-33, wherein the cylindrical roll is configured to be inserted into the culture space while the cylindrical role is in a contracted state and to expand within the culture space when disposed within the culture space.

Aspect 35 pertains to the cell culture system of any one of Aspects 31-34, wherein the cylindrical roll and the culture space are configured such that frictional forces between the polymer mesh material and a wall of the culture space hold the polymer mesh material in place within the culture space.

Aspect 36 pertains to the cell culture system of Aspect 34, wherein the cylindrical roll is configured to be inserted into the culture space through an opening in the bioreactor vessel.

Aspect 37 pertains to the cell culture system of Aspect 36, wherein the opening is one of the inlet and the outlet of the bioreactor vessel.

Aspect 38 pertains to the cell culture system of any one of Aspects 31-37, wherein the bioreactor vessel comprises a substrate support within the culture space, the substrate support being configured to guide, align, or secure the cell culture matrix within the culture space.

Aspect 39 pertains to the cell culture system of Aspect 38, wherein the substrate support comprises a support member extending from one of the first or second end towards the other of the first or second end, wherein the cylindrical roll is configured to surround the support member such that the support member is parallel to the central longitudinal axis of the cylindrical roll.

Aspect 40 pertains to the cell culture system of any one of Aspects 1-39, wherein the bioreactor vessel is configured to rotate about a central longitudinal axis of the bioreactor vessel during cell culture.

Aspect 41 pertains to the cell culture system of Aspect 40, wherein the central longitudinal axis is perpendicular to the direction of gravity during cell culture.

Aspect 42 pertains to the cell culture system of Aspect 40 or Aspect 41, wherein the cell culture system is configured such that the substrate is moved through the cell culture fluid during the rotation of the bioreactor vessel.

Aspect 43 pertains to the cell culture system of any one of Aspects 40-42, wherein the cell culture system further comprises a rotation means operably coupled to the bioreactor vessel and configured to rotate the bioreactor vessel about the central longitudinal axis.

Aspect 44 pertains to the cell culture system of anyone of Aspects 1-43, wherein the cell culture matrix comprises a plurality of substrates that comprises woven meshes of differing geometries, wherein the differing geometries are different in at least one of fiber diameter, opening diameter, or opening geometry.

Aspect 45 pertains to the cell culture system of Aspect 44, wherein the woven meshes of differing geometries are disposed in the bioreactor vessel in a predetermined arrangement based on desired flow characteristics within the bioreactor vessel.

Aspect 46 pertains to the cell culture system of Aspect 45, wherein the desired flow characteristics comprise at least one of uniform perfusion of liquid media across the cell culture matrix, and distribution of cell growth across the cell culture matrix.

Aspect 47 pertains to the cell culture system of Aspect 45 or Aspect 46, wherein the woven meshes of differing geometries comprises a first mesh with a first geometry and a second mesh with a second geometry, and wherein the predetermined arrangement comprises the first mesh being upstream of the second mesh with respect to the bulk flow direction.

Aspect 48 pertains to the cell culture system of Aspect 47, wherein the predetermined arrangement comprises a stack of the first mesh disposed upstream of a stack of the second mesh.

Aspect 49 pertains to the cell culture system of Aspect 47 or Aspect 48, wherein the predetermined arrangement comprises stacks of the first mesh and stacks of the second mesh in an alternating arrangement along the bulk flow direction.

Aspect 50 pertains to the cell culture system of anyone of Aspects 1-49, further comprising means for harvesting the adherent cells or cell byproducts.

Aspect 51 pertains to the cell culture system of Aspect 50, wherein the cell byproducts comprise at least one of proteins, antibodies, viruses, viral vectors, virus-like particles (VLPs), macrovesicles, exosomes, and polysaccharides.

Aspect 52 pertains to the cell culture system of any one of Aspects 1-51, wherein the substrate comprises a functionalized surface, the functionalized surface being physically or chemically modified for improved adhesion of the adherent cells to the polymer mesh material.

Aspect 53 pertains to the cell culture system of any one of the preceding Aspects, wherein the cell culture matrix comprises a surface configured for adsorption or absorption of components in the culture media onto the surface of the mesh.

Aspect 54 pertains to the cell culture system of any one of Aspects 1-53, wherein the cell culture matrix comprises a coating on a surface of the polymer mesh material, the coating being configured to promote adherence of the adherent cells.

Aspect 55 pertains to the cell culture system of Aspect 54, wherein the cells adhere to the coating.

Aspect 56 pertains to the cell culture system of Aspect 54 or Aspect 55, wherein the coating is a biological or synthetic bioactive molecule configured to promote cell attachment to the cell culture matrix.

Aspect 57 pertains to the cell culture system of any one of Aspects 54-56, wherein the coating is at least one of a hydrogel, collagen, Matrigel®, a bioactive molecule or peptide, and a biological protein.

Aspect 58 pertains to the cell culture system of any one of Aspects 53-56, wherein the functionalized surface is plasma treated.

Aspect 59 pertains to the cell culture system of any one of the preceding Aspect, wherein the cells comprise at least one of adherent cells, suspension cells, and loosely adherent cells that adhere to the woven mesh.

Aspect 60 pertains to the cell culture system of any one of the preceding Aspect, further comprising a media conditioning vessel configured to supply media to the inlet of the bioreactor vessel.

Aspect 61 pertains to a cell culture matrix comprising: a substrate comprising a first side, a second side opposite the first side, a thickness separating the first side and the second side, and a plurality of openings formed in the substrate and passing through the thickness of the substrate, wherein the plurality of openings is configured to allow flow of at least one of cell culture media, cells, or cell products through the thickness of the substrate.

Aspect 62 pertains to the cell culture matrix of Aspect 61, wherein the substrate comprises at least one of polystyrene, polyethylene terephthalate, polycarbonate, polyvinylpyrrolidone, polybutadiene, polyvinylchloride, polyethylene oxide, polypyrroles, and polypropylene oxide.

Aspect 63 pertains to the cell culture matrix of Aspect 61 or Aspect 62, wherein the substrate comprises at least one of a molded polymer lattice sheet, a 3D-printed lattice sheet, and a woven mesh sheet.

Aspect 64 pertains to the cell culture matrix of Aspect 63, wherein the substrate comprises the woven mesh comprising one or more fibers.

Aspect 65 pertains to the cell culture matrix of Aspect 64, wherein the one or more fibers comprise a cross-section shape that is at least one of flat, round, rectangular, or polygonal.

Aspect 66 pertains to the cell culture matrix of Aspect 64 or Aspect 65, wherein the one or more fibers comprises at least one of a monofilament fiber and a multifilament fiber.

Aspect 67 pertains to the cell culture matrix of any one of Aspects 64-66, wherein the one or more fibers comprises a first fiber with a first fiber diameter from about 50 μm to about 1000 μm, from about 50 μm to about 600 μm, from about 50 μm to about 400 μm, from about 100 μm to about 325 μm, or from about 150 μm to about 275 μm.

Aspect 68 pertains to the cell culture matrix of Aspect 67, wherein the one or more fibers further comprises a second fiber with a second fiber diameter from about 50 μm to about 1000 μm, from about 50 μm to about 600 μm, from about 50 μm to about 400 μm, from about 100 μm to about 325 μm, or from about 150 μm to about 275 μm.

Aspect 69 pertains to the cell culture matrix of Aspect 68, wherein the second fiber diameter is different than the first fiber diameter.

Aspect 70 pertains to the cell culture matrix of any one of Aspects 61-69, wherein the plurality of openings comprises an opening diameter of from about 100 μm to about 1000 μm, from about 200 μm to about 900 μm, or from about 225 μm to about 800 μm.

Aspect 71 pertains to the cell culture matrix of Aspect 70, wherein the fiber diameter is from about 250 μm to about 300 μm, and the opening diameter is from about 750 μm to about 800 μm, or wherein the fiber diameter is from about 270 μm to about 276 μm, and the opening diameter is from about 785 μm to about 795 μm.

Aspect 72 pertains to the cell culture matrix of Aspect 70, wherein the fiber diameter is from about 200 μm to about 230 μm, and the opening diameter is from about 500 μm to about 550 μm, or wherein the fiber diameter is from about 215 μm to about 225 μm, and the opening diameter is from about 515 μm to about 530 μm.

Aspect 73 pertains to the cell culture matrix of Aspect 70, wherein the fiber diameter is from about 125 μm to about 175 μm, and the opening diameter is from about 225 μm to about 275 μm, or wherein the fiber diameter is from about 150 μm to about 165 μm, and the opening diameter is from about 235 μm to about 255 μm.

Aspect 74 pertains to the cell culture matrix of any one of Aspects 70-73, wherein a ratio of the opening diameter to the fiber diameter is from about 1.0 to about 3.5, from about 1.25 to about 3.25, from about 1.4 to about 3.0, from about 1.5 to about 2.9, from about 1.5 to about 2.4, or from about 2.4 to about 2.9.

Aspect 75 pertains to the cell culture matrix of any one of Aspects 1-74, wherein the plurality of openings comprises openings with a shape that is square, rectangular, rhombus, rhomboid, circular, or oval.

Aspect 76 pertains to the cell culture matrix of any one of Aspects 1-75, wherein the plurality of openings is arrayed in a regular pattern.

Aspect 77 pertains to the cell culture matrix of any one of Aspects 1-76, wherein the cell culture matrix comprises a monolayer substrate.

Aspect 78 pertains to the cell culture matrix of any one of Aspects 1-77, wherein the cell culture matrix comprises a multilayer substrate comprising at least a first substrate layer and a second substrate layer, wherein the first substrate layer comprises a first side and a second side opposite to the first side, and the second substrate layer comprises a third side and a fourth side opposite to the third side, the second side facing the third side.

Aspect 79 pertains to the cell culture matrix of Aspect 78, wherein the multilayer substrate is configured so that the first substrate layer has a predetermined alignment with respect to the second substrate layer.

Aspect 80 pertains to the cell culture matrix of Aspect 79, wherein the multilayer substrate is configured so that an intersection of fibers on the first substrate layer faces an opening in the second substrate layer.

Aspect 81 pertains to the cell culture matrix of Aspect 79 or Aspect 80, wherein openings in the first substrate layer are at least partially overlapping with the openings in the second substrate layer.

Aspect 82 pertains to the cell culture matrix of Aspect 81, wherein the openings in the first and second substrate layers are aligned.

Aspect 83 pertains to the cell culture matrix of Aspect 78, wherein the multilayer substrate is configured so that the first substrate layer has a random alignment with respect to the second substrate layer.

Aspect 84 pertains to the cell culture matrix of any one of Aspects 61-83, wherein the cell culture matrix comprises a plurality of substrates, each of the plurality of substrates in a random orientation with respect to others of the plurality of substrates.

Aspect 85 pertains to the cell culture matrix of any one of Aspects 61-83, wherein the cell culture matrix comprises a plurality of substrates in a stacked arrangement.

Aspect 86 pertains to the cell culture matrix of Aspect 85, wherein the first and second sides of one of the plurality of substrates is substantially parallel to the first and second sides of other substrates in the stacked arrangement.

Aspect 87 pertains to the cell culture matrix of any one of Aspects 61-83, wherein the substrate is in a cylindrical roll configuration.

Aspect 88 pertains to the cell culture matrix of Aspect 87, wherein the cylindrical roll is configured to expand to a shape of a culture chamber within the bioreactor vessel via a partial unraveling of the cylindrical roll when disposed within the culture chamber.

Aspect 89 pertains to the cell culture matrix of Aspect 88, wherein the cylindrical roll is configured to be inserted into the culture space while the cylindrical role is in a contracted state and to expand within the culture space when disposed within the culture space.

Aspect 90 pertains to the cell culture matrix of any one of Aspects 61-89, wherein the cell culture matrix comprises a plurality of substrates that comprises woven meshes of differing geometries, wherein the differing geometries are different in at least one of fiber diameter, opening diameter, or opening geometry.

Aspect 91 pertains to the cell culture matrix of Aspect 90, wherein the woven meshes of differing geometries are ordered in a predetermined arrangement based on desired flow characteristics within the bioreactor vessel.

Aspect 92 pertains to the cell culture matrix of Aspect 91, wherein the desired flow characteristics comprise at least one of uniform perfusion of liquid media across the cell culture matrix, and distribution of cell growth across the cell culture matrix.

Aspect 93 pertains to the cell culture matrix of Aspect 91 or Aspect 92, wherein the woven meshes of differing geometries comprises a first mesh with a first geometry and a second mesh with a second geometry, and wherein the predetermined arrangement comprises the first mesh being upstream of the second mesh with respect to a desired bulk flow direction of cell culture media through the cell culture matrix.

Aspect 94 pertains to the cell culture matrix of Aspect 93, wherein the predetermined arrangement comprises a stack of the first mesh disposed upstream of a stack of the second mesh.

Aspect 95 pertains to the cell culture matrix of Aspect 93 or Aspect 94, wherein the predetermined arrangement comprises stacks of the first mesh and stacks of the second mesh in an alternating arrangement along the bulk flow direction.

Aspect 96 pertains to the cell culture matrix of any one of Aspects 61-95, wherein the cell culture matrix is configured for culturing and/or harvesting at least one of cells, proteins, antibodies, viruses, viral vectors, virus-like particles (VLPs), macrovesicles, exosomes, and polysaccharides.

Aspect 97 pertains to the cell culture matrix of any one of Aspects 61-96, wherein the substrate comprises a functionalized surface, the functionalized surface being physically or chemically modified for improved adhesion of the adherent cells to the polymer mesh material.

Aspect 98 pertains to the cell culture matrix of any one of Aspects 61-97, wherein the cell culture matrix comprises a surface configured for adsorption or absorption of components in the culture media onto the surface of the mesh.

Aspect 99 pertains to the cell culture matrix of any one of Aspects 61-98, wherein the cell culture matrix comprises a coating on a surface of the polymer mesh material, the coating being configured to promote adherence of the adherent cells.

Aspect 100 pertains to the cell culture matrix of Aspect 99, wherein the cells adhere to the coating.

Aspect 101 pertains to the cell culture matrix of Aspect 99 or Aspect 100, wherein the coating is a biological or synthetic bioactive molecule configured to promote cell attachment to the cell culture matrix.

Aspect 102 pertains to the cell culture matrix of any one of Aspects 99-101, wherein the coating is at least one of a hydrogel, collagen, Matrigel®, a bioactive molecule or peptide, and a biological protein.

Aspect 103 pertains to the cell culture matrix of any one of Aspects 99-102, wherein the functionalized surface is plasma treated.

Aspect 104 pertains to the cell culture matrix of any one of Aspects 61-103, wherein the cells comprise at least one of adherent cells, suspension cells, and loosely adherent cells that adhere to the woven mesh.

Aspect 105 pertains to a method of culturing cells in a bioreactor, the method comprising: providing a bioreactor vessel, the bioreactor vessel comprising: a cell culture chamber within the bioreactor vessel, and a cell culture matrix disposed in the cell culture chamber and configured to culture cells thereon, the cell culture matrix comprising a substrate comprising a first side, a second side opposite the first side, a thickness separating the first side and the second side, and a plurality of openings formed in the substrate and passing through the thickness of the substrate; seeding cells on the cell culture matrix; culturing the cells on the cell culture matrix; and harvesting a product of the culturing of the cells, wherein the plurality of openings in the substrate is configured to allow flow of at least one of cell culture media, cells, or cell products through the thickness of the substrate.

Aspect 106 pertains to the method of Aspect 105, wherein the substrate comprises at least one of a molded polymer lattice sheet, a 3D-printed lattice sheet, and a woven mesh sheet.

Aspect 107 pertains to the method of Aspect 105 or Aspect 106, wherein the substrate comprises a polymer material.

Aspect 108 pertains to the method of Aspect 107, wherein the polymer material is at least one of polystyrene, polyethylene terephthalate, polycarbonate, polyvinylpyrrolidone, polybutadiene, polyvinylchloride, polyethylene oxide, polypyrroles, and polypropylene oxide.

Aspect 109 pertains to the method of any one of Aspects 105-108, wherein the seeding comprises attaching the cells to the substrate.

Aspect 110 pertains to the method of any one of Aspects 105-109, wherein the seeding comprises injecting a cell inoculum directly into the cell culture matrix.

Aspect 111 pertains to the method of Aspect 110, wherein the cell inoculum is injected through a cell inoculum injection port in the bioreactor vessel.

Aspect 112 pertains to the method of Aspect 110 or Aspect 111, wherein a volume of the cell inoculum is about equal to a void volume of the cell culture chamber.

Aspect 113 pertains to the method of any one of Aspects 110-112, further comprising perfusing cell media through the culture chamber after injecting the cell inoculum.

Aspect 114 pertains to the method of any one of Aspects 105-113, further comprising supplying at least one of cell culture media and oxygen to the cells during culturing.

Aspect 115 pertains to the method of Aspect 114, wherein the supplying of the cell culture media comprises flowing the cell culture media through the cell culture chamber and across the substrate.

Aspect 116 pertains to the method of Aspect 114 or Aspect 115, wherein the supplying the cell culture media comprises providing a media conditional vessel fluidly connected to the bioreactor vessel and supplying the cell culture media from the media conditioning vessel to the bioreactor vessel.

Aspect 117 pertains to the method of Aspect 116, wherein, during or after culturing, at least a portion of the media is recovered from the bioreactor vessel and returned to the media conditioning vessel.

Aspect 118 pertains to the method of any one of Aspects 105-117, further comprising controlling the flow of cell culture media to the cell culture chamber, wherein the cell culture media comprises at least one of cells, cell culture nutrients, or oxygen.

Aspect 119 pertains to the method of any one of Aspects 105-118, further comprising analyzing the cell culture media, the cells, and/or the cell products within the bioreactor vessel or output from the bioreactor vessel.

Aspect 120 pertains to the method of Aspect 119, wherein the analyzing comprises measuring at least one of $pH_1$, $pO_1$, $[glucose]_1$, $pH_2$, $pO_2$, $[glucose]_2$, and flow rate, wherein $pH_1$, $pO_1$, and $[glucose]_1$ are measured within the cell culture chamber, and wherein $pH_2$, $pO_2$, and $[glucose]_2$ are measured at an outlet of the cell culture chamber or the bioreactor vessel.

Aspect 121 pertains to the method of Aspect 119 or Aspect 120, wherein the flow of cell culture media to the cell culture chamber is controlled based on at least in part the results of the analyzing the cell culture media, the cells, and/or the cell products.

Aspect 122 pertains to the method of any one of Aspects 120-121, wherein a perfusion flow rate of the cell culture media to the cell culture chamber is continued at a present rate if at least one of $pH_2 \geq pH_{2min}$, $pO_2 \geq pO_{2min}$, and $[glucose]_2 \geq [glucose]_{2min}$, wherein $pH_{2min}$, $pO_{2min}$, and $[glucose]_{2min}$ are predetermined based on the cell culture system design.

Aspect 123 pertains to the method of any one of Aspects 120-122, wherein if the current flow rate is less than or equal to a predetermined max flow rate of the cell culture system, the perfusion flow rate is increased.

Aspect 124 pertains to the method of any one of Aspects 120-123, wherein if the current flow rate is not less than or equal to the predetermined max flow rate of the cell culture system, a controller of the cell culture system reevaluates at least one of: $pH_{2min}$, $pO_{2min}$, and $[glucose]_{2min}$, $pH_1$, $pO_1$, and $[glucose]_1$, and a height of the bioreactor vessel.

Aspect 125 pertains to the method of any one of Aspect 105-124, wherein the cells have a viability of over about 90% or over about 95% after culturing for at least about 24 hours, at least about 48 hours, or at least about 72 hours.

Aspect 126 pertains to the method of any one of Aspects 105-125, wherein the cells comprise at least one of adherent cells, suspension cells, and loosely adherent cells that adhere to the cell culture matrix.

Aspect 127 pertains to the method of any one of Aspects 105-126, wherein the product of the culturing of the cells comprises at least one of cells, proteins, antibodies, viruses, viral vectors, virus-like particles (VLPs), macrovesicles, exosomes, and polysaccharides.

Aspect 128 pertains to the method of Aspect 127, wherein the product of the culturing of the cells comprises cells that are at least 80% viable, at least 85% viable, at least 90% viable, at least 91% viable, at least 92% viable, at least 93% viable, at least 94% viable, at least 95% viable, at least 96% viable, at least 97% viable, at least 98% viable, or at least 99% viable.

Aspect 129 pertains to a bioreactor system comprising: a cell culture vessel comprising at least one reservoir; and a cell culture matrix disposed in the at least one reservoir, the cell culture matrix comprising a woven substrate having a plurality of interwoven fibers with surfaces configured for adhering cells thereto.

Aspect 130 pertains to the system of Aspect 129, wherein the woven substrate comprises a uniform arrangement of the plurality of interwoven fibers.

Aspect 131 pertains to the system of Aspect 129 or Aspect 130, wherein the woven substrate comprises a plurality of openings disposed between the plurality of fibers.

Aspect 132 pertains to the system of any one of Aspect 129-131, wherein the plurality of fibers comprises polymer fibers.

Aspect 133 pertains to the system of Aspect 132, wherein the polymer fibers comprise at least one of polystyrene, polyethylene terephthalate, polycarbonate, polyvinylpyrrolidone, polybutadiene, polyvinylchloride, polyethylene oxide, polypyrroles, and polypropylene oxide.

Aspect 134 pertains to the system of any one of Aspects 129-133, wherein the cell culture matrix comprises a plurality of woven substrates.

Aspect 135 pertains to the system of Aspect 134, wherein each substrate of the plurality of substrates comprises a first side, a second side opposite the first side, a thickness separating the first and second sides, wherein the plurality of openings pass through the thickness of the substrate.

Aspect 136 pertains to the system of Aspect 134 or Aspect 135, wherein the substrates of the plurality of substrates are arranged adjacent to each other such that one of the first and second side of a substrate is adjacent to other of the first or second side of an adjacent substrate.

Aspect 137 pertains to the system of any one of Aspects 134-136, wherein at least a portion of the plurality of substrates are not separated by a spacer material or barrier.

Aspect 138 pertains to the system of any one of Aspects 134-137, wherein at least a portion of the plurality of substrates are in physical contact with each other.

Aspect 139 pertains to the system of any one of Aspects 129-138, wherein the cell culture vessel comprises at least one port configured for supplying material to or removing material from the at least one reservoir through the at least one port.

Aspect 140 pertains to the system of Aspect 139, wherein the at least one port comprises at least one inlet for supplying material to the at least one reservoir, and at least one outlet for removing material from the at least one reservoir.

Aspect 141 pertains to the system of Aspect 140, wherein the material comprises at least one of media, cells, or cell products.

Aspect 142 pertains to a bioreactor system comprising: a cell culture vessel comprising a first end, a second end, and at least one reservoir between the first and second ends; and a cell culture matrix disposed in the at least one reservoir, the cell culture matrix comprising a plurality of woven substrates each comprising a plurality of interwoven fibers with surfaces configured for adhering cells thereto, wherein the bioreactor system is configured to flow material through the at least one reservoir in a flow direction from the first end to the second end, wherein the substrates of the plurality of woven substrates are stacked such that each woven substrate is substantially parallel to each of the other woven substrates and is substantially perpendicular to the flow direction.

Aspect 143 pertains to the system of Aspect 142, wherein each of the substrates comprises a first side, a second side opposite the first side, a thickness separating the first and second sides, wherein the plurality of openings pass through the thickness of the substrate.

Aspect 144 pertains to a bioreactor system comprising: a cell culture vessel comprising a first end, a second end, and at least one reservoir between the first and second ends; and a cell culture matrix disposed in the at least one reservoir, the cell culture matrix comprising a plurality of woven substrates each comprising a plurality of interwoven fibers with surfaces configured for adhering cells thereto, wherein the bioreactor system is configured to flow material through the at least one reservoir in a flow direction from the first end to the second end, wherein the substrates of the plurality of woven substrates are stacked such that each woven substrate is substantially parallel to each of the other woven substrates and is substantially parallel to the flow direction.

Aspect 145 pertains to the system of Aspect 144, wherein each of the substrates comprises a first side, a second side opposite the first side, a thickness separating the first and second sides, wherein the plurality of openings pass through the thickness of the substrate.

Aspect 146 pertains to a bioreactor system comprising: a cell culture vessel comprising a first end, a second end, and at least one reservoir between the first and second ends; and a cell culture matrix disposed in the at least one reservoir, the cell culture matrix comprising a woven substrate comprising a plurality of interwoven fibers with surfaces configured for adhering cells thereto, and wherein at least one of the at least one reservoir and the cell culture matrix is configured to rotate about a central longitudinal axis of the bioreactor vessel during cell culture.

Aspect 147 pertains to the system of Aspect 146, wherein the woven substrate is disposed within the at least one reservoir as a cylindrical substrate at least partially surrounding the central longitudinal axis of the bioreactor vessel.

Aspect 148 pertains to the system of Aspect 146 or Aspect 147, wherein the bioreactor system is configured to flow material through the at least one reservoir in a flow direction from the first end to the second end, Aspect 149 pertains to the system of Aspect 148, wherein a central longitudinal axis of the cylindrical substrate is parallel to a flow direction of the media.

Aspect 150 pertains to the system of any one of Aspects 146-149, wherein the cylindrical substrate comprises a rolled woven substrate that is configured to expand to be in contact with a wall of the at least one reservoir via an un-rolling of the rolled woven substrate.

Aspect 151 pertains to the system of any one of Aspects 146-150, wherein the rolled woven substrate is configured to expand to a shape of the interior of the at least one reservoir in the cell culture vessel.

Aspect 152 pertains to the system of Aspect 151, wherein the rolled woven substrate is configured to be inserted into the culture space while the rolled woven substrate is in a contracted rolled state and to expand within the reservoir when disposed within the reservoir.

Aspect 153 pertains to the system of Aspect 151 or Aspect 152, wherein the rolled woven substrate and the reservoir are configured such that frictional forces between the woven substrate and the wall of the reservoir hold the woven substrate substantially in place within the reservoir.

Aspect 154 pertains to the system of any one of Aspects 151-153, wherein the rolled woven substrate is configured to be inserted into the reservoir through an opening in the cell culture vessel.

Aspect 155 pertains to the system of Aspect 154, wherein the opening is one of the inlet and the outlet of the cell culture vessel.

Aspect 156 pertains to the system of any one of Aspects 146-155, wherein the cell culture vessel comprises a substrate support within the reservoir, the substrate support being configured to guide, align, or secure the woven substrate within the culture space.

Aspect 157 pertains to the system of Aspect 156, wherein the substrate support comprises a support member extending from one of the first or second end towards the other of the first or second end, wherein the rolled woven substrate is configured to surround at least a portion of a circumference of the support member such that the support member is parallel to the central longitudinal axis of the rolled woven substrate.

Aspect 158 pertains to the system of any one of Aspects 146-157, wherein the central longitudinal axis is perpendicular to the direction of gravity during cell culture.

Aspect 159 pertains to the system of any one of Aspects 146-158, wherein the bioreactor system is configured such that the substrate is moved through the cell culture fluid during the rotation of the cell culture vessel.

Aspect 160 pertains to the system of any one of Aspects 146-159, wherein the bioreactor system further comprises a rotation means operably coupled to the cell culture vessel and configured to rotate the cell culture vessel about the central longitudinal axis.

Aspect 161 pertains to a cell culture matrix comprising: a woven substrate comprising a plurality of fibers that are interwoven and a plurality of openings disposed between the plurality of fibers, wherein the fibers each comprise a surface configured for adhering cells thereto.

Aspect 162 pertains to the matrix of Aspect 161, wherein the surface of the fibers is configured for releasably adhering cells thereto.

Aspect 163 pertains to the matrix of Aspect 161 or Aspect 162, wherein the plurality of fibers comprises polymer fibers.

Aspect 164 pertains to the matrix of Aspect 163, wherein the polymer fibers comprise at least one of polystyrene, polyethylene terephthalate, polycarbonate, polyvinylpyrrolidone, polybutadiene, polyvinylchloride, polyethylene oxide, polypyrroles, and polypropylene oxide.

Aspect 165 pertains to the matrix of any one of Aspects 161-164, the cell culture matrix further comprising a plurality of woven substrates.

Aspect 166 pertains to the matrix of Aspect 165, wherein each substrate of the plurality of substrates comprises a first side, a second side opposite the first side, a thickness separating the first and second sides, wherein the plurality of openings pass through the thickness of the substrate.

Aspect 167 pertains to the matrix of Aspect 165 or Aspect 166, wherein the substrates of the plurality of substrates are arranged adjacent to each other such that one of the first and second side of a substrate is adjacent to other of the first or second side of an adjacent substrate.

Aspect 168 pertains to the matrix of any one of Aspect 165-167, wherein at least a portion of the plurality of substrates are not separated by a spacer material or barrier.

Aspect 169 pertains to the matrix of any one of Aspects 165-168, wherein at least a portion of the plurality of substrates are in physical contact with each other.

Aspect 170 pertains to a bioreactor system comprising: a vessel comprising a media inlet, a media outlet, and a cell culture space, the cell culture space being disposed in an interior of the vessel and in fluid communication with and between the media inlet and media outlet; wherein the cell culture space comprises a cell culture substrate section and a spacer section disposed between the cell culture substrate section and the media outlet, and wherein the cell culture space is configured to contain a cell culture substrate in a packed-bed configuration.

Aspect 171 pertains to the bioreactor system of Aspect 170, wherein the cell culture substrate comprises the cell culture matrix of any one of Aspects 61-104.

Aspect 172 pertains to the bioreactor system of Aspect 170 or Aspect 171, further comprising a flow distribution plate disposed between the media inlet and the cell culture space.

Aspect 173 pertains to the bioreactor system of any one of Aspects 170-172, further comprising a packed-bed retention layer disposed between the cell culture space and the spacer section.

Aspect 174 pertains to the bioreactor system of any one of Aspects 170-173, further comprising a spacer insert disposed between the media outlet and the cell culture space.

Aspect 175 pertains to the bioreactor system of Aspect 174, wherein the spacer insert is disposed between the media outlet and the packed-bed retention layer.

Definitions

"Wholly synthetic" or "fully synthetic" refers to a cell culture article, such as a microcarrier or surface of a culture vessel, that is composed entirely of synthetic source materials and is devoid of any animal derived or animal sourced materials. The disclosed wholly synthetic cell culture article eliminates the risk of xenogeneic contamination.

"Include," "includes," or like terms means encompassing but not limited to, that is, inclusive and not exclusive.

"Users" refers to those who use the systems, methods, articles, or kits disclosed herein, and include those who are culturing cells for harvesting of cells or cell products, or those who are using cells or cell products cultured and/or harvested according to embodiments herein.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "μm" for gram(s), "mL" for milliliters, and "rt" for room temperature, "nm" for nanometers, and like abbreviations).

Specific and preferred values disclosed for components, ingredients, additives, dimensions, conditions, and like aspects, and ranges thereof, are for illustration only; they do not exclude other defined values or other values within defined ranges. The systems, kits, and methods of the disclosure can include any value or any combination of the values, specific values, more specific values, and preferred values described herein, including explicit or implicit intermediate values and ranges.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that any particular order be inferred.

It will be apparent to those skilled in the art that various modifications and variations can be made without departing from the spirit or scope of the disclosed embodiments. Since modifications, combinations, sub-combinations and variations of the disclosed embodiments incorporating the spirit and substance of the embodiments may occur to persons skilled in the art, the disclosed embodiments should be construed to include everything within the scope of the appended claims and their equivalents.

As discussed above, aspects of one or more embodiments include the media inlet being configured to supply at least one of cells, cell culture media, and other components to the interior cavity of the bioreactor vessel, and the media outlet is configured to withdraw at least one of cells or other biological agents, cell culture media, and cellular or biological by-products from the interior cavity during or after cell culture. In addition, as discussed herein, to perform a harvest procedure of the contents of the bioreactor, the media outlet can be configured to supply pressurized fluid to the spacer section during the harvesting operation, and the media inlet is configured to withdraw at least one of cells, cell culture media, and cell by-products from the interior cavity during the harvesting operation. The bioreactor system is configured to fill the interior cavity with the pressurized fluid via the media outlet to force out at least one of cells, cell culture media, and cell by-products through the media inlet. Accordingly, the spacer section may also be referred to herein as the harvesting volume, meaning it is a space or volume that is pressurized or filled with fluid via some pressurization, in order to perform at least part of the harvest procedure.

Figure 18B:
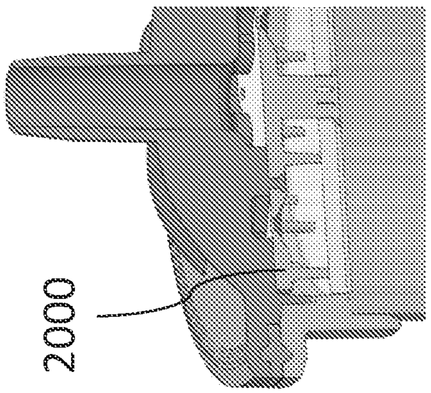
FIG. 18B is a partial cross-section close-up view of a portion of FIG. 18A, according to one or more embodiments.
Figure 18A:
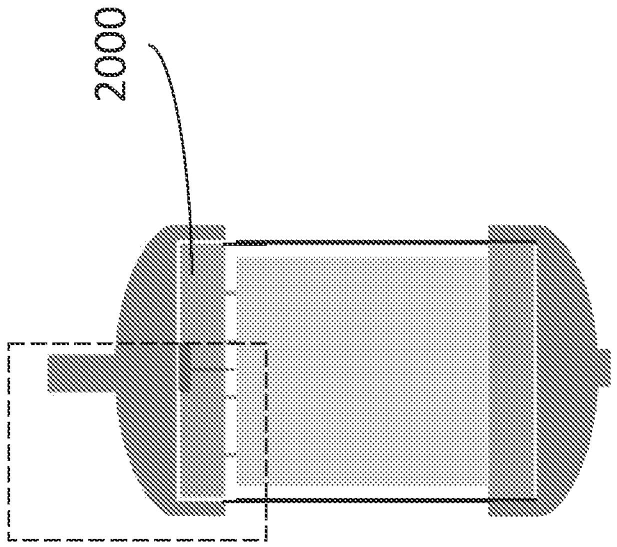
FIG. 18A is a schematic cross-section view of a bioreactor vessel with a pin field, according to one or more embodiments.

Some embodiments disclosed herein present a removable spacer within the spacer section or harvesting volume. In some embodiments, as shown in FIGS. 18A and 18B, a pin field 2000 can be disposed between the media outlet and the cell culture substrate. The pin field 2000 can be characterized as one or more members extending substantially parallel to the longitudinal axis of the bioreactor flow direction, or as extending in a direction that extends from the cell culture substrate to the outlet. FIG. 18B shows a magnified view of a portion of the bioreactor vessel and pin field from FIG. 18A. The pin field can at least partly define the harvesting volume by creating separation between one end of the bioreactor vessel or the media outlet and the cell culture substrate. The pin field may also serve to retain the cell culture substrate in place within the interior cavity of the bioreactor vessel. In some embodiments, as shown in FIGS. 18A and 18B, the pine field can be integral with a fluid outlet plate near the media outlet. In FIG. 18B, the holes in the fluid outlet plate can be seen. In other words, the fluid outlet plate can serve to collect fluid from within the interior cavity and deliver it to the media outlet, while also including the pin field. It should be understood that when flow through the vessel is reversed, such as during the harvesting procedure, the fluid outlet plate can act in reverse as well-acting effectively as a fluid inlet plate for fluid coming into the bioreactor vessel via the media outlet to be distributed across the width of the interior cavity and/or the cell culture substrate for effective harvesting. It is also noted that the harvesting volume in FIGS. 18A and 18B is relatively small in height compared to some of the other embodiments shown and described herein. Only a small space is required in some applications, as long as that space can hold some harvesting solution which is then pressurized and sent through the cell culture substrate during harvesting.

Figure 19B:
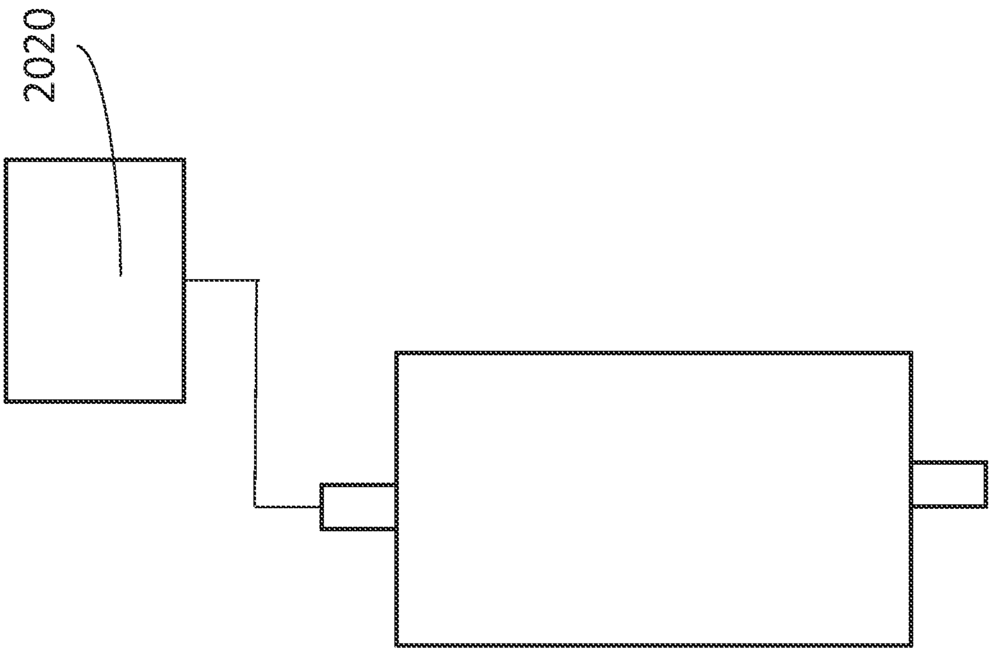
FIG. 19B is a schematic view of a bioreactor vessel with a cell culture section and an external harvesting volume, according to one or more embodiments.
Figure 19A:
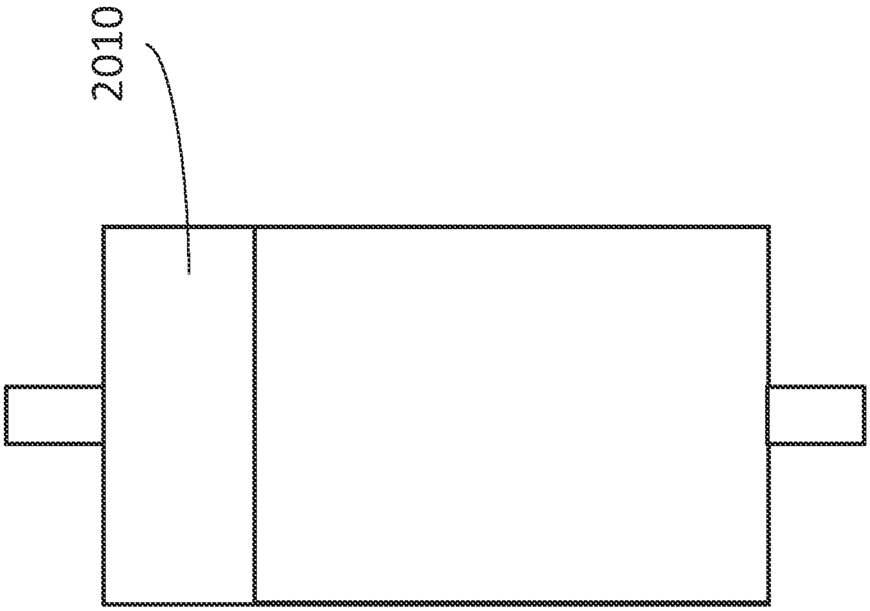
FIG. 19A is a schematic view of a bioreactor vessel with a cell culture section and harvesting volume within the same vessel, according to one or more embodiments.

In some of the foregoing embodiments, the harvesting volume is shown within the bioreactor vessel between the cell culture substrate and the media outlet. This is shown schematically by the harvesting volume 2010 in FIG. 19A. However, embodiments are not limited to this configuration. In FIG. 19B, for example, the harvesting volume 2020 is disposed outside of the interior cavity of the bioreactor vessel that houses the cell culture substrate, but is fluidly connected to the media outlet. Thus, the harvesting solution, which is pressurized in the harvesting volume 2020, can be sent via a fluid connector, such as a hose, to the cell culture substrate through the media inlet for harvesting. It should be appreciated that the harvesting volume 2020 being separated from the cell culture substrate can mean that the harvesting volume is removed entirely from the bioreactor vessel, or that is simply held within a separate compartment from the cell culture substrate within a multi-compartment bioreactor vessel. The separate housing of the harvesting volume can be advantageous in terms of reducing the size and complexity of the bioreactor vessel, which may be a disposable unit and may come pre-loaded with cell culture material. The resulting reduced size and complexity can limit waste generated from the consumable or disposable portions, and can also allow for greater flexibility in arranging the various components of the system. In addition, by housing the harvesting volume in a separate vessel, the harvesting solution can more easily be kept separate from the cell culture mesh until the desire time, the conditions of the harvesting solution can be more easily controlled, and the pressurization of the harvesting solution is easier to achieve without adversely affecting the cell culture substrate, cells, or other components before harvesting occurs. The harvesting volume can still be maintained with the normal fluid recirculation path of the bioreactor system, even with external to the cell culture space.

According to some embodiments, the harvest solution can contain one or more components that help to harvest cells and/or release them from the cell culture substrate. Examples include Accutase® or TrypLE®, but a person of ordinary skill in the art would understand alternative harvesting agents that can be used.

Further Examples

Figure 20:
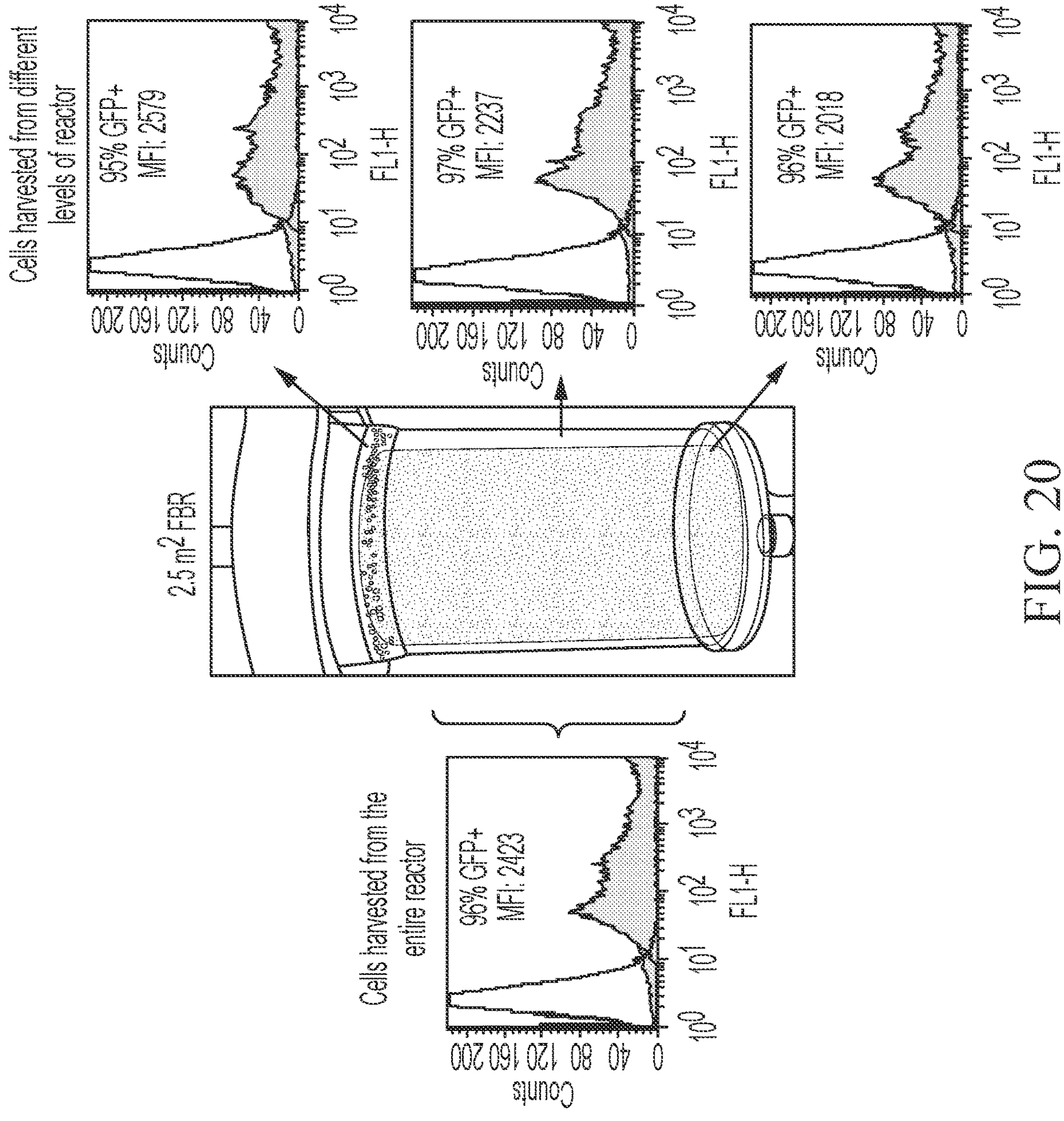
FIG. 20 shows the cells harvested from the top, middle, and bottom of a bioreactor, as well as the average harvest count, according to one or more embodiments.

As discussed herein, embodiments of this disclosure include a bioreactor and methods of using the same that result in uniform fluid flow, cell seeding, cell growth and culture, and cell harvesting. As an example, FIG. 20 shows a bioreactor according to an embodiment of this disclosure. The bioreactor includes a fixed-bed cell culture substrate that includes layers of woven PET mesh arranged in a stack. It is noted that there is no other fluid flow apparatus or other physical structure separating the layers of the cell culture substrate. The resulting fixed-bed is a uniform, consistent bed that enables superior performance and had a surface area of 2.5 $m^2$. Cells were seeded and cultured within the bioreactor of FIG. 20 on the cell culture substrate. Then, following a culture period, layers of substrate were removed from three different regions of the packed bed: top, middle, and bottom. Cells were counted on these removed layers using GFP staining to see representative cell counts in the different regions of the packed bed. As shown in FIG. 20, the cell counts for cells harvested from the top (95% GFP+, MFI: 2579), middle (97% GFP+, MFI: 2237), and bottom (96% GFP+, MFI: 2018) of a bioreactor were remarkably consistent. The resulting average count was 96% GFP+ and MFI of 2423.

FIG. 21 shows the consistent AAV2-GFP vector yield/$cm^2$ across multiple example runs and bioreactor sizes, according to one or more embodiments. Specifically, the three sizes include cell culture substrate surface areas of 0.2 $m^2$, 0.7 $m^2$, and 2.5 $m^2$. Each size resulted in consistent % GFP+ cells and consistent viral vector yields as measured by Bulk VG/$cm^2$.

FIG. 22 shows an example of the AAV2-GFP VG yield/$cm^2$ of an Embodiment A according to this disclosure as compared to other platforms. Like that of FIG. 20, the bioreactor of Embodiment A has a cell culture substrate surface area of 2.5 $m^2$. The other two platforms used for comparison consisted of a 2.65 m2 commercially available fixed-bed reactor, and a T75 flask from Corning® with a 2D cell growth surface. Three experiments were run for each platform. Compared to the 2.65 $m^2$ platform, Embodiment A showed a large increase in AAV2-GFP VG/$cm^2$, resulting in an over twenty-fold increase compared to that other platform.

FIG. 23 shows an example of the AAV2-GFP VG yield/vessel of an Embodiment A according to this disclosure as compared to the other platforms from FIG. 22. Again, Embodiment A shows a more than twenty-fold increase compared to the 2.65 $m^2$ platform, and an over 330-fold increase compared to the T75 flask.

Figure 24B:
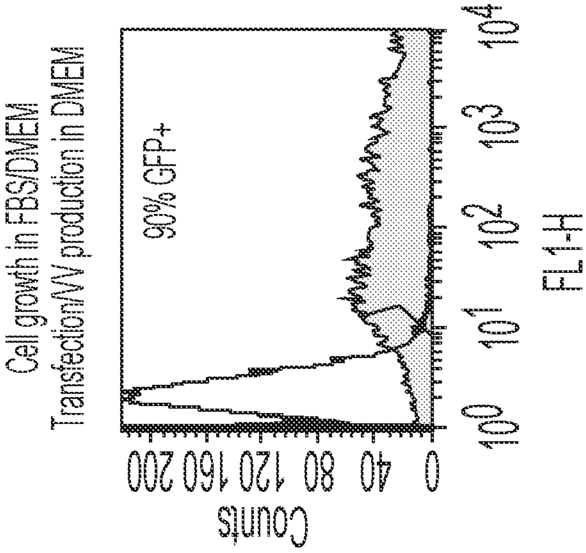
FIG. 24B shows the AAV2-GFP viral vector production in a bioreactor according to an embodiment of this disclosure using FBS/DMEM medium was used for HEK293T growth phase, serum-free DMEM medium was used for transfection and production phases.
Figure 24A:
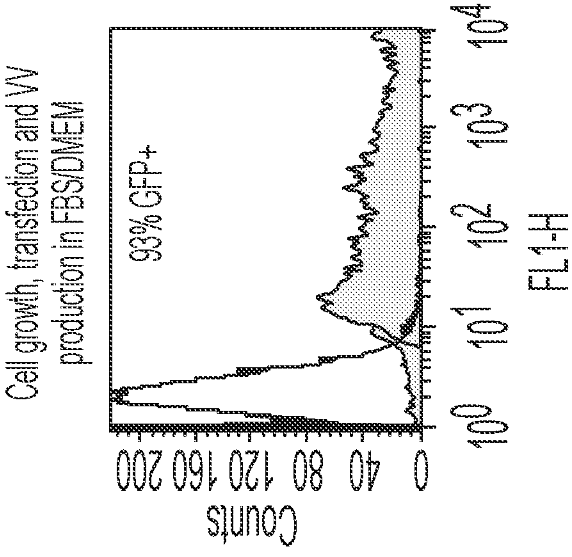
FIG. 24A shows the AAV2-GFP viral vector production in a bioreactor according to an embodiment of this disclosure using FBS/DMEM medium.

FIG. 24*a* shows the AAV2-GFP viral vector production in a bioreactor according to an embodiment of this disclosure using FBS/DMEM medium for the entire protocol, while FIG. 24B shows the AAV2-GFP viral vector production in a bioreactor according to an embodiment of this disclosure using FBS/DMEM medium was used for HEK293T growth phase, with serum-free DMEM medium was used for transfection and production phases.

Figure 25:
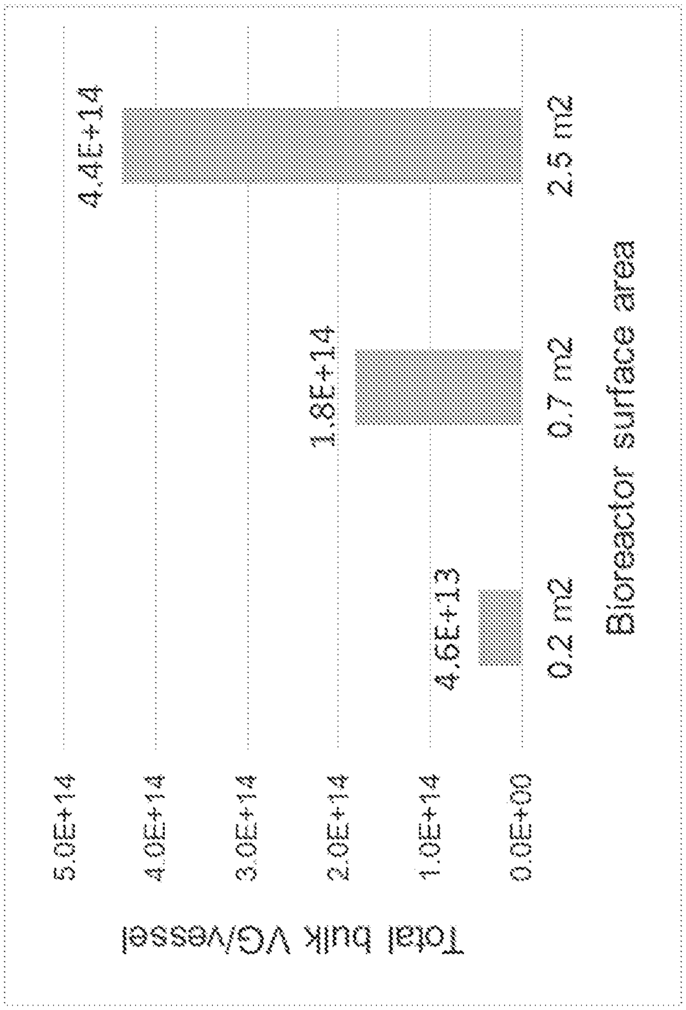
FIG. 25 shows an example of the total bulk VG per vessel for different surface area size of cell culture substrate, according to embodiments of this disclosure.

FIG. 25 shows an example of the total bulk VG per vessel for different surface area size of cell culture substrate, according to embodiments of this disclosure. Flow cytometry for GFP+ cells 72 hrs post-transfection and AAV2-GFP yields are show for both conditions. These figures show the effectiveness of using serum-free media with embodiments of this disclosure.

As demonstrated herein, embodiments of this disclosure provide cell culture bioreactors, systems, and related methods that enable uniform fluid flow through the fixed bed demonstrated. Embodiments have demonstrated homogeneous HEK293 growth and efficient viable cells harvest. Embodiments have demonstrated >90% transfection efficiency and ~2.0E+10 AAV2-GFP vector yield/$cm^2$ was consistently across multiple runs and bioreactor sizes, confirming design scalability. In side-by-side evaluations, embodiments of this disclosure demonstrated a greater than 20-fold higher AAV2-GFP VG yield/$cm^2$ compared to another fixed bed reactor and comparable VG yield/$cm^2$ compared to T75 flask. In addition, embodiments of this disclosure demonstrated feasibility of performing transfection and viral vector production in serum-free DMEM medium without significant impact on viral vector yield.

Further advantages of the embodiments herein are also clear. For example, in some embodiments, the cell culture substrate extends uninterrupted across diameter of the interior cavity of the bioreactor. This is simpler than complex flow channels and pathways employed in alternatives. The flow through the fixed bed is unidirectional, or can be characterized as plug flow, which again simplifies operation and improves performance, including for example, cell seeding and harvesting. As a result, all of the layers of packed bed are being perfused with same efficiency and flow or flux of media across or through the layer.

What is claimed:

1. A fixed-bed bioreactor system comprising:

a vessel comprising a media inlet, a media outlet, and an interior cavity disposed between and in fluid communication with the media inlet and media outlet;

a cell culture substrate disposed in the interior cavity between the media inlet and the media outlet in a packed-bed configuration, the cell culture substrate comprising a plurality of porous disks in a stacked arrangement;

a harvesting volume configured to hold a fluid, the harvesting volume being in fluid communication with the interior cavity; and a spacer disposed in the interior cavity between the cell culture substrate and the media outlet, the spacer being configured to space the cell culture substrate a distance from the media outlet and to confine the cell culture substrate to the cell culture section of the interior cavity, wherein each of the plurality of porous disks comprises a surface configured to culture cells thereon, and wherein the spacer comprises a pin field comprising a plurality of pins extending in a direction parallel to a height of the stacked arrangement of porous disks.

2. The fixed-bed bioreactor system of claim 1, wherein the harvesting volume is disposed within the vessel, between the media outlet and the cell culture substrate.

3. The fixed-bed bioreactor system of claim 1, wherein the harvesting volume is disposed outside of the vessel, and is fluidly connected to the media outlet of the vessel.

4. The fixed-bed bioreactor system of claim 1, wherein each disk of the plurality of porous disks comprises a first side, a second side opposite the first side, a disk thickness separating the first side and the second side, and a plurality of openings formed in the disk and passing through the disk thickness, wherein the plurality of openings is configured to allow flow of at least one of cell culture media, cells, or cell by-products through the cell culture substrate.

5. The fixed-bed bioreactor system of claim 1, further comprising an inlet distribution plate disposed between the media inlet and the cell culture substrate, the inlet distribution plate being configured to distribute fluid entering the interior cavity from the media inlet across an area of the cell culture substrate.

6. The fixed-bed bioreactor system of claim 1, further comprising an outlet distribution plate disposed between the cell culture substrate and the media outlet.

7. The fixed-bed bioreactor system of claim 6, wherein the pin field is integral with the outlet distribution plate.

8. The fixed-bed bioreactor system of claim 7, wherein the harvesting volume is configured to pressurize the fluid within the harvesting volume and direct that pressurized fluid through a fluid pathway to the media outlet to harvest contents from the vessel.

9. The fixed-bed bioreactor system of claim 1, wherein the bioreactor system is configured to achieve greater than about 90% viral transfection efficiency, or greater than about 95% viral transfection efficiency.

10. The fixed-bed bioreactor system of claim 9, wherein the bioreactor system is configured to achieve uniform transfection efficiency throughout the cell culture substrate.

11. The fixed-bed bioreactor system of claim 10, wherein the uniform transfection comprises transfection efficiencies within about ±10%, within about ±8%, within about ±6%, within about ±4%, within about ±2%, or within about ±1% on individual porous disks throughout the cell culture substrate stack configuration.

12. The fixed-bed bioreactor system of claim 1, wherein the plurality of porous disks comprises a plurality of layers of woven mesh.

13. The fixed-bed bioreactor system of claim 12, wherein the each of the plurality of layers of woven mesh has a defined, substantially uniform array of pores.

14. The fixed-bed bioreactor system of claim 12, wherein each layer of the plurality of layers of woven mesh comprises a plurality of interwoven fibers, the plurality of interwoven fibers comprising a first group of fibers running in parallel to each other in a first direction, and a second group of fibers running parallel to each other in a second direction.

15. The fixed-bed bioreactor system of claim 1, wherein the media inlet is configured to supply at least one of cells and cell culture media to the interior cavity before or during cell culture, and the media outlet is configured to withdraw at least one of cells, cell culture media, and cell by-products from the interior cavity during or after cell culture.

16. The fixed-bed bioreactor system of claim 15, wherein the bioreactor system is configured to supply pressurized fluid from the harvesting volume to the cell culture substrate during a harvesting operation, and the media inlet is configured to withdraw at least one of cells, cell culture media, and cell by-products from the interior cavity during the harvesting operation.

17. The fixed-bed bioreactor system of claim 16, wherein the bioreactor system is configured to fill the interior cavity with the pressurized fluid via the media outlet to force out at least one of cells, cell culture media, and cell by-products through the media inlet.

18. The fixed-bed bioreactor system of claim 1, wherein the plurality of porous disks comprises from 50 to 1000 porous disks.

* * * * *